(12) United States Patent
Voelker et al.

(10) Patent No.: US 8,497,102 B2
(45) Date of Patent: Jul. 30, 2013

(54) MUTANT METHYLGLYOXAL SYNTHASE (MGS) FOR THE PRODUCTION OF A BIOCHEMICAL BY FERMENTATION

(75) Inventors: François Voelker, Montrond les Bains (FR); Laurence Dumon-Seignovert, Pont du Chateau (FR); Philippe Soucaille, Deyme (FR)

(73) Assignee: Metabolic Explorer, Saint Beauzire (FR)

( * ) Notice: Subject to any disclaimer, the term of this patent is extended or adjusted under 35 U.S.C. 154(b) by 0 days.

(21) Appl. No.: 13/387,095

(22) PCT Filed: Jul. 30, 2010

(86) PCT No.: PCT/EP2010/061094
§ 371 (c)(1),
(2), (4) Date: Jan. 25, 2012

(87) PCT Pub. No.: WO2011/012693
PCT Pub. Date: Feb. 3, 2011

(65) Prior Publication Data
US 2012/0122166 A1    May 17, 2012

Related U.S. Application Data

(60) Provisional application No. 61/230,076, filed on Jul. 30, 2009.

(30) Foreign Application Priority Data

Jul. 30, 2009 (EP) .................................... 09166815

(51) Int. Cl.
C12P 7/56       (2006.01)
C12P 7/18       (2006.01)
C07H 21/04     (2006.01)
C12N 1/00       (2006.01)
C12N 1/21       (2006.01)
C12N 1/19       (2006.01)
C12N 9/88       (2006.01)
C12P 7/26       (2006.01)

(52) U.S. Cl.
USPC ........... 435/139; 435/148; 435/158; 435/232; 435/243; 435/252.3; 435/252.33; 435/254.21; 536/23.2

(58) Field of Classification Search
None
See application file for complete search history.

(56) References Cited

U.S. PATENT DOCUMENTS
2010/0261239 A1  10/2010  Soucaille et al.

FOREIGN PATENT DOCUMENTS
WO     2008/116848     10/2008

OTHER PUBLICATIONS

European Search Report based on European Application No. EP 09 16 6815 completed Sep. 4, 2009.
International Search Report based on PCT/EP2010/061094 mailed Aug. 30, 2010.
Cooper et al.; "The Formation and Catabolism of Methylglyoxal During Glycolysis in *Escherichia coli*"; FEBS Letters; Dec. 1970; vol. 11; No. 4; pp. 273-276; North-Holland Publishing Company; Amsterdam.
Hopper et al.; "The Regulation of *Escherichia coli* Methylglyoxal Synthase: A New Control Site in Glycolysis"; FEBS Letters; Mar. 1971; vol. 13; No. 4; pp. 213-216; North-Holland Publishing Company; Amsterdam.
Hopper et al.; "The Purification and Properties of *Escherichia coli* Methylglyoxal Synthase"; Biochem. J.; 1972; vol. 128; pp. 321-329.
Saadat et al.; "Identification of Catalytic Bases in the Active Site of *Escherichia coli* Methylglyoxal Synthase: Cloning, Expression, and Functional Characterization of Conserved Aspartic Acid Residues"; Biochemistry; 1998; vol. 37; pp. 10074-10086; American Chemical Society.
Saadat et al.; "The Crystal Structure of Methylglyoxal Synthase From *Escheria coli*"; Structure; Mar. 1999; vol. 7; pp. 309-317; Elsevier Science Ltd.
Saadat et al.; "Mirroring Perfection: The Structure of Methylglyoxal Synthase Complexed With the Competitive Inhibitor 2-Phosphoglycolate"; Biochemistry 2000; vol. 39; pp. 2950-2960; American Chemical Society.
Marks et al.; "Mutagenic Studies on Histidine 98 of Methylglyoxal Synthase: Effects on Mechanism and Conformational Change"; Biochemistry; 2004; vol. 43; pp. 3802-3813; American Chemical Society.
Totemeyer et al.; "From Famine to Feast: The Role of Methylglyoxal Production in *Escherichia coli*"; Molecular Microbiology; 1998; vol. 27; No. 3; pp. 553-562; Blackwell Science Ltd.
Ferguson et al.; "Methylglyoxal Production in Bacteria: Suicide or Survival"; Arch Microbiol; 1998; vol. 170; pp. 209-219; Springer-Verlag.

(Continued)

*Primary Examiner* — Suzanne M Noakes
*Assistant Examiner* — Jae W Lee
(74) *Attorney, Agent, or Firm* — Baker, Donelson, Bearman, Caldwell & Berkowitz, PC

(57) ABSTRACT

The present invention concerns a method for the production of a biochemical selected among lactic acid, acetol and 1,2-propanediol, comprising culturing a microorganism modified for an improved production of the biochemical selected among lactic acid, acetol and 1,2-propanediol in an appropriate culture medium and recovery of the desired biochemical which may be further purified wherein the microorganism expresses a methylglyoxal synthase (MGS) enzyme which activity is not inhibited by orthophosphate.
The present invention concerns a mutant methylglyoxal synthase (MGS) comprising at least one amino acid residue in the protein sequence of the parent enzyme replaced by a different amino acid residue at the same position wherein
   the mutant enzyme has retained more than 50% of the methylglyoxal synthase activity of the parent enzyme and
   the methylglyoxal synthase activity of the mutant MGS is not inhibited by orthophosphate as compared to the parent enzyme.

1 Claim, 4 Drawing Sheets

OTHER PUBLICATIONS

Garvie; "Bacterial Lactate Dehydrogenases"; Microbiological Reviews; Mar. 1980; vol. 44; No. 1; pp. 106-139.

Cooper; "Metabolism of Methylglyoxal in Microorganisms"; Ann. Rev. Microbiol.; 1984; vol. 38; pp. 49-68; Annual Reviews Inc.

Rule et al.; "Overproduction and Nucleotide Sequence of the Respiratory D-Lactate Dehydrogen of *Escherichia coli*"; Journal of Bacteriology; Mar. 1985; vol. 161; No. 3; pp. 1059-1068; American Society for Microbiology.

Dong et al.; "Three Overlapping LCT Genes Involved in L-Lactate Utilization by *Escherichia coli*"; Journal of Bacteriology; Oct. 1993; vol. 175; No. 20; pp. 6671-6678; American Society for Microbiology.

Grabar et al.; "Methylglyoxal Bypass Identified as Source of Chiral Contamination in L(+) and D(−)—Lactate Fermentations by Recombinant *Escherichia coli*"; Biotechnol Lett; 2006; vol. 28; pp. 1527-1535; Springer.

Misra et al.; "Glyoxalase III from *Escherichia coli*: A Single Novel Enzyme for the Conversion of Methylglyoxal Into D-Lactate Without Reduced Glutathione"; Biochem. J.; 1995; vol. 305; pp. 999-1003.

Cameron et al.; "Metabolic Engineering of Propanediol Pathways"; Biotechnol. Prog. 1998; vol. 14; pp. 116-125; American Chemical Society and American Institute of Chemical Engineers.

Altaras et al.; "Enhanced Production of (R)-1,2-Propanediol by Metabolically Engineered *Esherichia coli*"; Biotechnol. Prog. 2000, vol. 16; pp. 940-946; American Chemical Society and American Institute of Chemical Engineers.

Bennett et al.; "Microbial Formation, Biotechnological Production and Applications of 1,2-Propanediol"; Appl. Microbiol Biotechnol; 2001; vol. 55; pp. 1-9; Springer Verlag.

Ko et al.; "Conversion of Methylglyoxal to Acetol by *Escherichia coli* Aldo-Keto Reductases"; Journal of Bacteriology; Aug. 2005; vol. 187; No. 16; pp. 5782-5789; American Society for Microbiology.

Datta et al.; "Lactic Acid: Recent Advances in Products, Processes and Technologies—A Review"; J. Chem. Technol. Biotechnol.; 2006; vol. 81; pp. 1119-1129; Society of Chemical Industry.

Wasewar; "Separation of Lactic Acid: Recent Advances"; Chem. Biochem.; 2005; vol. 19; No. 2; pp. 159-172.

The Uniprot Consortium; 2008; Nucleic Acids Res.; vol. 36; pp. D190-195.

Guldener et al.; "A New Efficient Gene Disruption Cassette for Repeated Use in Budding Yeast"; 1996; vol. 24; No. 13; pp. 2519-2524; Oxford University Press.

Schiestl et al.; "High Efficiency Transformation of Intact Yeast Cells Using Single Stranded Nucleic Acids as a Carrier"; Curr Genet; 1989; vol. 16; pp. 339-346; Springer-Verlag.

Shevchuk et al.; "Construction of Long DNA Molecules Using Long PCR-Based Fusion of Several Fragments Simultaneously"; Nucleic Acids Research; 2004; vol. 32; No. 2; Oxford University Press.

```
            1
MGSA_TRESC  -------MRF KLRIALVAHD NRKADIVDWA LNNAEMLSQH RLFGTGTTGT LVRESPMKRG I-ASDITCMH
MGSA_COXBU  --------MT VKKIALVAHD RMKKELIEWI KHQNLLKHH  ELYATGSTGQ AIEKT----- L-NVTVTKME
MGSA_RALSO  -------MPK RRKIALIAHD HKKDDMIAFA QTHKAFLMRC DLLATGTTGG RLQDE----- V-GLSVQPML
MGSA_BURMA  -------MS  TPRIALIAHD AKKDDIVALA GAYRATLAQC RLVATGTTGG KIAQA----- H-GLDVERKL
MGSA_BRUME  -------MTQ RLPIALIAHD QKKDDMVAFA RAHEQALSPY DIVATGTTGG LIQDA----- CPSLNIHRVK
MGSA_AGRT5  -------MEG QRCIALIAHD EKKDDMADPA RHHQKVLASF RIVATGTTGG RVQEA----- CPGLEVIRLK
MGSA_RHIME  -------MAD RKCIALIAHD QKKDDLLAAFA KANEAVLSKW KIVATGTTGG RVLDV----- CPALDIVRLK
MGSA_SYMTH  ---------- -MRIALIAHD NRKQDMLKFV KDHKSAFEGH QLFATGTTGK LIREH----- T-GLDVHCFL
MGSA_BORBU  ---------M EKKIALIAHD KKKEDLVNPV KQNYLFLSKP KLIATGTTGS RIQQA----- T-DLTIFKYK
MGSA_BORGA  ---------M EKKIALIAHD KKKDDLVNPV KQNYLFLSKP KLIATGTTGS RIQQA----- T-DLTIIKYK
MGSA_CLOPE  ---------- -MKIALIAHD KKKEEMIELA KDFEDKLSKH ILVATGTTGL KIMQN----- T-SLEVKRCK
MGSA_OCEIH  ---------- -MNIALIAHD EKKEDMIQFT TAYTHVLSKH RLFATGTTGM KISNA----- T-GLQIHRFQ
MGSA_THETN  ---------- -MNIALIAHD QKKELMVNFA IAYKHIFEKC NLYATGHTGQ LIKEA----- T-GLDVHCLL
MGSA_CLOTS  --------MV NLNIALIAHD MKKSLMIDFA IAYKDILEKC NIYATGATGQ LVEEA----- T-GIKVNKFL
MGSA_GEOKA  ---------- -MKIALIAHD QKKEEMVAFA TAYAPVLANH ELYATGTTGL RIQEA----- T-GLPVHRFQ
MGSA_BACCR  ---------- -MKIALIAHD KKKNDMVSFA YAYKPIFEQH ELFATGTTGL RIMEA----- T-GLVITRYQ
MGSA_BACSK  ---------- -MKIALIAHD KKKQELVDFC VAYEPILKEH ELYATGTTGT RIMEA----- T-ELVVIRPK
MGSA_BACHD  ---------- -MRIALIAHD KKKDEMVQFT IAYKDVLKDH ELYATGTTGM RIMEA----- A-QLPVKRFK
MGSA_BACSU  ---------- -MKIALIAHD KKKQDMVQFT TAYRDILKNH DLYATGTTGL KIHEA----- T-GLQIERFQ
MGSA_ENTFA  ---------- -MKIALIAHD RKKTLMIKLA TAYKHILEKH ELYATGTTGM KVMEA----- T-GLPVHCFK
MGSA_LISIN  ---------- -MKIALIAHD EKKDLMVGFA TAYKHLLEPH QLYATGTTGL RIIEA----- T-GITVHRFK
MGSA_HAEIN  MQTTTRTLTQ HKRIALVAHD SCKKNLLNWT QKHKEALKPH ILYATGTTGH ILERE----- T-GLSIQSLL
MGSA_PHOPR  MQVTPRTMNK SKHIALVAHD NCKQDLLRWV KEFEDKLEDH TLYATGTTGH LLSKE----- T-GLKINCMI
MGSA_VIBVU  MQKTTRTMPA HKHIALVAHD NYKPELLRWV KENKEKLQSH FLYATGTTGH MLSRE----- T-GLAIKSMI
MGSA_VIBCH  MKKTTRTMAA HKHVALVAHD NCKGELLRWV TENKEKLQRH FLYATGTTGH MLSKE----- T-GLAIKSMI
MGSA_VIBPA  MQKTTRTMPA HKHVALVAHD NCKPELLRWV KENKEKLQRH FLYATGTTGH MLSKE----- T-GLAIKSMI
MGSA_PHOLL  MELTTRTMAT AKNIALIAHD HCKTSLLAWS KKHKSLLKRH HLYATGTTGN LIQNE----- T-GLSVTNML
MGSA_YERPE  MELTTRTIAA RKHIALVSHD HCKKSLLAWV MENRDLLAQH ELYATGTTGN LVQKA----- T-GIDVHCLL
MGSA_ERWCT  MEFTTRTIPA QKHIALVAHD HCKQSLLDWV GTNKQQLTEH TLYATGTTGN LIQSN----- T-GLPVKSML
MGSA_ECOL6  MELTTRTLPS RKHIALVAHD HCKQMLMSWV ERHQPLLEQH VLYATGTTGN LISRA----- T-GMNVNAML
MGSA_SALTI  MELTTRTLPT RKHIALVAHD HCKQMLMNWV ERHQPLLEKH VLYATGTTGN LIQRA----- T-GMDVNAML
MGSA_MANSM  METTFRHVAA QKHIALVAHD HCKEDLINWC QRNVHHLQNH QLYATGTTGH LIEKA----- T-ELKINSLL
MGSA_PASMU  MQSTARTLSV NKHIALVAHD HCKQDLINWC KTHRTLLAQH TLYATGTTGN LIQKE----- A-NLPIKSLL
MGSA_CLOAB  -------MNS KKKIALVAHD NRKKALISWC EANSEVLSNH SLCGTGTTAK LIKEA----- T-GLEVFPYK
MGSA_THEMA  -------MDK KKRIALIAHD RRKRDLLEWV SFNLGTLSKH ELYATGTTGA LLQEK----- L-GLFVHRLK
MGSA_LEPIC  --MKEVSVPA IKRIVLIAHD NRKEDLVNWV KTHREILSKH QLYGTGTTGK LISEE----- T-ELPVYRFL

71
MGSA_TRESC  SGPMGGDAEI AALVVRKEID FAVFFIDDLN PQPHEADIQM LLRQCRIHNI PIACNRYSAD LMITSSLWDD
MGSA_COXBU  SGPLGGDLQL GAKIVNKEID ILIFFWDPLE AQPHDPDVRA LLRIAVVWNL PVACNASTAD YLLT-SPLFD
MGSA_RALSO  SGPWGGDLQI GAQLAEGRVD AVIFLRDPMT PQPHEDDINA LVRACDVHDV PCATNLATAD LVM-------
MGSA_BURMA  SGPLGGDLQI GAELADGRVD IVIFLRDPMT AQPHDPDITA LVRACDVHDV PVATNVATAR VLL-------
MGSA_BRUME  SGPLGGDQQI GAMIAEGTVE VLIFFIDDLS PLPHDVDVKA LTRLGSVYDI PMALNRATAE KIV-------
MGSA_AGRT5  SGPLGGDQQI GAMIATGEVD MLIFFTDPLT AMPHDVDVKA LTRIAIVYDI PMALNRATAE NLI-------
MGSA_RHIME  SGPLGGDQQI GALIATGDVD CLIFFVDPLT AMPHDVDVKA LMRLAIVYDI PMALNRATAE QLI-------
MGSA_SYMTH  SGPLGGDQQI GSRVATGEID MVIFLRDPLT AMPHEPDVQG LLRLCDVRDI PVATNLGSAR MFA-------
MGSA_BORBU  SGPMGGDQQI GAEVAEGNIL AIFFFRDPLT SQPHEPDVSA LIRLCDVHKI PLATNVKTAE ILI-------
MGSA_BORGA  SGPMGGDQQI GAEVAEGNVL AIFFFRDPLT NQPHEPDVSA LIRLCDVHNI PLATNVKTAE ILI-------
MGSA_CLOPE  SGPLQGDQEI GAMVANHDVD MVIFLRDPLT AQPHEPDISA LLRLCDVVKV PLATNTESAK LIM-------
MGSA_OCEIH  SGPLGGDQDI GAMIANGEMD MIIFFRDPLT AQPHEPDVSA LMRLCDVHQI PLVTNIAGAE IFI-------
MGSA_THETN  PGFLGGDQQI GALIAENKID LLRVCDVHSI VQPHEPDILA LLRVCDVHSI PVATNIATAE VLL-------
MGSA_CLOTS  PGPMGGDQQI GAMIAEDKMD LVIFLRDPLT AQPHEPDILA LLRVCDVHSI PLATNLATAE VLI-------
MGSA_GEOKA  SGPYGGDQEI GAMIARNEMD LVIFFRDPLT AQPHEPDISA LMRLCDVYAV PLATNIGTAE LLI-------
MGSA_BACCR  SGPLGGDQQI GAMIAKNDLD MVIFFRDPVNA LLRLCDVVAI PLATNMASAE MLM-------
MGSA_BACSK  SGPLGGDQQI GALVAENQFD LILFMRDPLT AQPHEPDVTA LIRLCDVQSV PLATNMGTAE ILI-------
MGSA_BACHD  SGPLGGDQQI GALVAENKFD LIIFFRDPLT AQPHEPDVTA LVRLCDVQRV PLATNIGTAE ILI-------
MGSA_BACSU  SGPLGGDQQI GALIAANALD LVIFFRDPLT AQPHEPDVSA LIRLCDVYSI PLATNMGTAE ILV-------
MGSA_ENTFA  SGPLGGDQQI GAMISEDNID LVIFLRDPLS AQPHEPDVTA LIRLSDVYEI PLATNIGSAE ILL-------
MGSA_LISIN  SGPLGGDQQI GARISENKMD LVIFLRDPLT AQPHEPDVSA LIRLCDVHEI PLATNIGTAE ILI-------
MGSA_HAEIN  SGPMGGDQQL GGLIAEKKID MMIFFWXPMN AAPHEPDVKA LMRIECVHNI PVAINQSSAD FLLT-SVLFE
MGSA_PHOPR  SGPMGGDQQL GALISESKID MMIFFWDPLN AVPHDPDVKA LLRISAVWNV PVATNRASAD PMIT-SFLLA
MGSA_VIBVU  SGPMGGDQQL GALISEGKID MLIFFWDPLN AVPHDPDVKA LLRIASVWNI PVATNRATAK FLPE-SPLLN
MGSA_VIBCH  SGPMGGDQQL GALISEGKID VLIFFWDPLN AVPHDPDVKA LLRIASVWNI PVATNRASAK FLPS-SSLME
MGSA_VIBPA  SGPMGGDQQL GALISEGKID VLVFFWDPLN AVPHDPDVKA LLRIASVWNI PVATNRATAK FLFD-SPLLE
MGSA_PHOLL  SGPLGGDQQI GSLISEGKID VLIFFWDPLN SVPHDPDVKA LLRLATVWNI PVATNLASAD PIVS-SPLFS
MGSA_YERPE  SGPMGGDQEV GALISEKKID ILIFFWDPLN AVPHDPDVKA LLPLATVWNI PVATNRSTAD PLIG-STLFS
MGSA_ERWCT  SGPLGGDQQV GALISEGKID LMIFFWDPLN AVPHDPDVKA LLRLATVWNI PVATNVSTAD FLIN-SALFK
MGSA_ECOL6  SGPLGGDQQV GALISEGKID VLIFFWDPLN AVPHDPDVKA LLRLATVWNI PVATNVATAD FIIQ-SPHFN
MGSA_SALTI  SGPMGGDQQV GALISEGKID VLIFFWDPLN AVPHDPDVKA LLRLATVWNI PVATNVSTAD PIIQ-SPHPN
MGSA_MANSM  SGPMGGDQQL GALIAENKID VMIFFWDPMN AVPHDPDVKA LLRIAAVWNI PHAMNIASAD LLIN-SPLIN
MGSA_PASMU  SGPMGGDQQL GGLIAEKQID VLIFFWDPMN AVPHDPDVKA LMRIATVWNI PVAMNMATAD FLIT-SPSFA
MGSA_CLOAB  SGPLGGDQQI GAAIVNEDID PMIFFWDPLT AQPHDPDVKA LLRISVLYDI PIAMNESTAB FLIK-SPIMK
MGSA_THEMA  SGPLGGDQQI GAMIAEGKID VLIFFWDPLE PQAHDVDVKA LIRIATVWNI PVAITRSTAD FLIS-SPLMN
MGSA_LEPIC  SGPLGGDQQI GAKIAEGDLD IVIFFWDPLT AQPHDPDVKA LLRIAVLYNV PMACNRSTAD YMIS-SPQFT
```

Fig. 1

```
            141
MGSA_TRESO   AGYVPKDPIY  APFDRKAFEE  SLKVKE----
MGSA_COXBU   SDYHPETPDY  EAYRNRII--  ----------
MGSA_RALSO   IALGLAQPDP  KEIHA-----  ----------
MGSA_BURMA   DDLARRLTAN  A---------  ----------
MGSA_BRUME   RALD------  ----------  ----------
MGSA_AGRT5   --------DF  NSAD------  ----------
MGSA_RHIME   --------DF  RRN-------  ----------
MGSA_SYMTH   DDL----MRL  KDVK------  ----------
MGSA_BORBU   KGLESLIF--  ----------  ----------
MGSA_BORGA   KGFEGLNT--  ----------  ----------
MGSA_CLOPE   ADI-------  ----------  ----------
MGSA_OCEIH   HGLSRGDLKW  REIIKERQEK  EGTP------
MGSA_THETN   KGMEMGLLDW  RQI-------  ----------
MGSA_CLOTS   KGLDAGLLEW  RNAVK-----  ----------
MGSA_GEOKA   RALERGDLAW  RSIVRGQTKG  GEESKTER--
MGSA_BACCR   HALERGDLDY  RKLRK-----  ----------
MGSA_BACSK   KGLERGDFAF  RDIIHEQEKA  NPLKEG----
MGSA_BACHD   KGLARGDFTW  RELVHDEEEP  RV--------
MGSA_BACSU   RTLDEGVFEF  RDLLRGEEPN  V---------
MGSA_ENTFA   RGVEAGFADF  REVIHEGDRR  PLAF------
MGSA_LISIN   RGLGAGFLDW  RDLRRNDE--  ----------
MGSA_HAEIN   QDVEIDVPDY  EGYLKERLA-  ----------
MGSA_PHOPR   EEISIEIPDY  EAYLAERIG-  ----------
MGSA_VIBVU   EEVDVEIPDY  QAYLAGRT--  ----------
MGSA_VIBCH   QEVQIEIPDY  QAYLAERT--  ----------
MGSA_VIBPA   QEVDIEVPDY  EAYLAERM--  ----------
MGSA_PHOLL   ESVDIQVPDY  QHYLNGRLK-  ----------
MGSA_YERPE   SEVTIAIPDY  DRYMQQRLDL  K---------
MGSA_ERWCT   EPVQIAIPDY  QRYLQDRLK-  ----------
MGSA_ECOL6   DAVDILIPDY  QRYLADRLK-  ----------
MGSA_SALTI   DAVDILIPDY  ARYLAERLK-  ----------
MGSA_MANSM   REIELRIPDY  QTYLQKRLK-  ----------
MGSA_PASMU   QETQVRIPDY  DGYLKERLK-  ----------
MGSA_CLOAB   EQHERHIIDY  YQKIRKDNF-  ----------
MGSA_THEMA   DVYEKIQIDY  EEELERRIRK  VVEGEEEET
MGSA_LEPIC   KTYKKILLSY  NTKVKKD---  ----------
```

Fig. 1 (end)

MUTANT METHYLGLYOXAL SYNTHASE (MGS) FOR THE PRODUCTION OF A BIOCHEMICAL BY FERMENTATION

CROSS REFERENCE TO RELATED APPLICATIONS

This application is a §371 National Stage Application of PCT/EP2010/061094, filed Jul. 30, 2010, which claims priority to European Application No. 09166815.2, filed Jul. 30, 2009 and U.S. Provisional Application No. 61/230,076, filed Jul. 30, 2009.

BACKGROUND OF THE INVENTION

1. Field of the Invention

The present invention concerns a method for the production of a biochemical selected among lactic acid, acetol and 1,2-propanediol, comprising culturing a microorganism modified for an improved production of the biochemical selected among lactic acid, acetol and 1,2-propanediol in an appropriate culture medium and recovery of the desired biochemical which may be further purified wherein the microorganism expresses a methylglyoxal synthase (MGS) enzyme which activity is not inhibited by orthophosphate.

The present invention also relates to a mutant methylglyoxal synthase (MGS) comprising at least one amino acid residue in the protein sequence of the parent enzyme replaced by a different amino acid residue at the same position wherein the mutant enzyme has retained more than 50% of the methylglyoxal synthase activity of the parent enzyme and the methylglyoxal synthase activity of the mutant MGS is not inhibited by orthophosphate as compared to the parent enzyme.

2. Description of Related Art

Methylglyoxal synthase (MGS) was discovered and identified as the first enzyme of the methylglyoxal bypass in *E. coli*. MGS was later found in a wide range of organisms including Gram-negative as well as Gram-positive bacteria and yeast (Cooper (1984)). Methylglyoxal bypass can serve as an alternative pathway for the conversion of triosephosphates to pyruvate during the catabolism of glucose (Cooper and Anderson (1970), Cooper (1984)). The Embden-Meyerhoff-Parnas (EMP) pathway or glycolysis involves the conversion of the triosephosphate glyceraldehyde-3-phosphate (G3P) to pyruvate whereas the methylglyoxal bypass starts from the second triosephosphate, dihydroxyacetone phosphate (DHAP), that is converted to pyruvate via the intermediates methylglyoxal (MG) and lactate.

MGS, which was first purified and characterized in *E. coli* (Hopper and Cooper (1971 and 1972)) catalyses the conversion of 1 mole of DHAP to 1 mole of MG and 1 mole of orthophosphate (Pi). MGS is very specific for DHAP, which seems to be the only substrate accepted by the enzyme with a good affinity (Affinity constant Km varied from 0.2 to 0.47 mM). Several inhibitors of the enzyme were identified: phosphoenolpyruvate (PEP), 3-phosphoglycerate, Pi and pyrophosphate (PPi).

The recent identification of the gene coding for MGS in *E. coli* (yccG, then renamed mgsA) allowed easier production and characterization of recombinant MGS after cloning and overexpression of the mgsA gene (Tötemeyer et al (1998)). A refined characterization of the enzyme was proposed (Saadat and Harrison (1998)) and the inhibition by the most potent inhibitor, Pi, was further investigated: Pi acted as an allosteric inhibitor of the enzyme, meaning that in the presence of phosphate, a higher amount of DHAP was necessary for the enzymatic reaction to proceed (See also characterization of native MGS from *E. coli* given in Example 2). Several MGS mutants (on positions D20, D71, D91, D10 and H98), always impairing the catalytic rate of the enzyme were characterized and a catalytic mechanism was proposed (Saadat and Harrison (1998), Marks et al (2004)). The three dimensional structure of MGS from *E. coli* was determined after crystallisation of the enzyme (Saadat and Harrison (1999 and 2000)). MGS is a homohexamer with 6 identical units of 17 kDa. Phosphate can bind to the active site of MGS and a hypothesis for the transmission of allosteric information through the salt bridges between the monomers was proposed, although no clear evidence was given.

Production of several products of interest, lactate, acetol and 1,2-propanediol, can result from the catabolism of different carbon substrates (glucose, fructose, sucrose, glycerol) through the methylglyoxal bypass and especially through MGS.

The routes for catabolism of methylglyoxal have been investigated in bacteria (Ferguson et al, 1998) to understand the detoxification of this compounds but also for purposes of production of 1,2-propanediol. Three pathways that can lead to the production of lactate from methylglyoxal have been identified in *E. coli:*

The first one is the glutathione dependent glyoxalase I-II system (encoded by gloA and gloB genes) which converts methylglyoxal into D-lactate in two steps (Cooper, 1984).

The second is the glutathione independent glyoxalase III enzyme which catalyses the conversion of methylglyoxal into D-lactate in one step (Misra et al, 1995).

The third system is the degradation of methylglyoxal by methylglyoxal reductases, resulting either in acetol or in D- or L-lactaldehyde (Cameron et al, 1998, Bennett and San, 2001). L-lactaldehyde can be further converted to L-lactate by the action of aldehyde dehydrogenases e.g. by the enzymes encoded by the aldA or aldB genes (Grabar et al, 2006).

Lactate produced by one of the three systems can be further transformed into pyruvate by D- or L-lactate dehydrogenases. These enzymes, in contrast to fermentative lactate dehydrogenases, are flavin-linked membrane-bound proteins that are activated only under aerobic conditions (Garvie, 1980). D- and L-lactate dehydrogenases are coded respectively by the dld and lldD (or lctD) genes in *E. coli* (Rule et al, 1985, Dong et al, 1993).

Acetol or lactaldehyde produced by the third system can be converted to 1,2-propanediol by several enzymatic activities, especially glycerol dehydrogenase (encoded by gldA gene) or 1,2-propanediol oxidoreductase (encoded by fucO gene) in *E. coli* (Altaras and Cameron, 2000).

1,2-propanediol or propylene glycol, a C3 dialcohol, is a widely-used chemical. It is a component of unsaturated polyester resins, liquid detergents, coolants, anti-freeze and de-icing fluids for aircraft. Propylene glycol has been increasingly used since 1993-1994 as a replacement for ethylene derivatives, which are recognised as being more toxic than propylene derivatives.

1,2-propanediol is currently produced by chemical means using a propylene oxide hydration process that consumes large amounts of water. Propylene oxide can be produced by either of two processes, one using epichlorhydrin, and the other hydroperoxide. Both routes use highly toxic substances. In addition, the hydroperoxide route generates by-products such as tert-butanol and 1-phenyl ethanol. For the production of propylene to be profitable, a use must be found for these by-products. The chemical route generally produces racemic 1,2-propanediol, whereas each of the two stereoisomers (R)1,2-propanediol and (S)1,2-propanediol are of interest for certain applications (e.g. chiral starting materials for specialty chemicals and pharmaceutical products).

Acetol or hydroxyacetone (1-hydroxy-2-propanone) is a C3 keto alcohol. This product is used in vat dyeing process in the textile industry as a reducing agent. It can advantageously replace traditional sulphur containing reducing agents in order to reduce the sulphur content in wastewater, harmful for the environment. Acetol is also a starting material for the chemical industry, used for example to make polyols or heterocyclic molecules. It possesses also interesting chelating and solvent properties.

Acetol is currently produced mainly by catalytic oxidation or dehydration of 1,2-propanediol. New processes starting from renewable feedstocks like glycerol are now proposed (see DE4128692 and WO 2005/095536). Currently, the production cost of acetol by chemical processes reduces its industrial applications and markets.

The disadvantages of the chemical processes for the production of 1,2-propanediol and acetol make biological synthesis an attractive alternative. MGS is the mandatory first step from central metabolism for the production of these two compounds. Processes for the production of 1,2-propanediol or acetol using different microorganism, Clostridium sphenoides (DE3336051), Klebsiella pneumoniae (WO 2004/087936), recombinant yeast (WO 99/28481) or recombinant E. coli (WO 98/37204) have been disclosed. Alternative approaches for the production of 1,2-propanediol or acetol have also been disclosed (WO 2005/073364, WO 2008/116852, WO 2008/116848, WO 2008/116849, WO 2008/116851)).

Lactic acid or lactate and its derivatives have a wide range of applications in the food, pharmaceutical, leather and textile industries. Recently, polylactic acid (PLA) has been developed as a renewable, biodegradable and environmentally friendly plastic and therefore, the demand for lactate is expected to expand. Lactate can be produced either by a chemical synthesis or by a biological process. However, only a biological process is able to produce the desired stereoisomer, D- or L-lactate with high optical purity, which is an important characteristic for many of its end uses. Physical properties and biodegradation rate of PLA can be controlled by manipulating the ratio of the chiral substrates, D- and L-lactate. Therefore, availability of biological processes for the production of optically pure D- and L-lactate is a prerequisite for high quality polymer synthesis.

Lactic acid bacteria are natural producers of lactate and some can be found to be specific for the D- or L-form. These bacteria have been traditionally used for the production of lactate as specialty chemical (e.g. in US 2004/0005677). However, with the emergence of lactate as commodity chemical for PLA synthesis, more efficient and cost-effective processes are needed. Alternative biocatalysts able to growth in mineral salt medium and to use a range of different sugar substrates are investigated. Yeasts and E. coli combine these characteristics with the availability of a wide range of genetic tools for metabolic engineering. Use of these catalysts for the production of lactic acid has been described in WO 03102201, WO 03102152 and US 2005/0112737 for yeast strains and in EP 1760156 and WO 2005/033324 for E. coli strains. These production processes for D- or L-lactate in microorganisms rely on the reduction of pyruvate produced by the catabolism of sugars by NADH-dependent lactate dehydrogenases, generally under anaerobic conditions. The methylglyoxal bypass with the three pathways for the degradation of MG mentioned above can serve as an alternative non-fermentative pathway for the production of lactate, as described in PCT/EP2009/053093.

According to the allosteric inhibition of MGS by Pi, the conditions necessary for the enzyme to be active would be a high concentration of its substrate DHAP or a low concentration of Pi. When Pi is limiting in the environment, G3P dehydrogenase cannot continue to work without one of its substrate and therefore G3P and hence DHAP will accumulate, filling the two conditions for efficient work of MGS. Under these conditions, methylglyoxal bypass will replace glycolysis for catabolism of triosephosphates. When Pi is abundant, glycolysis will operate because the concentration of Pi would be too high and the concentration of DHAP to low for MGS to be active (Cooper (1984), Fergusson et al (1998)). This mechanism allows the microorganism to cope with different situations with regards to Pi. However, concerning the production of metabolites in the methylglyoxal bypass when these molecules are the end-products of the metabolism, the two parallel pathways, glycolysis and methylglyoxal bypass will have to work together: glycolysis to ensure the supply of precursors and energy for growth and methylglyoxal bypass for the synthesis of the wanted products. In this case, a MGS enzyme that has lost its inhibition by phosphate would be a clear advantage.

The inventors have identified new mutant MGS that had lost allosteric inhibition by phosphate, while keeping most of their specific activity for the conversion of DHAP into MG, as demonstrated in Example 2 by the characterization of purified enzymes. Use of these mutants is a key element in the design of more efficient processes for the production of the products of the methylglyoxal bypass, particularly acetol, 1,2-propanediol and lactate.

SUMMARY

The present invention concerns a method for the production of a biochemical selected among lactic acid, acetol and 1,2-propanediol, comprising culturing a microorganism modified for an improved production of the biochemical selected among lactic acid, acetol and 1,2-propanediol in an appropriate culture medium and recovery of the desired biochemical which may be further purified wherein the microorganism expresses a methylglyoxal synthase (MGS) enzyme which activity is not inhibited by orthophosphate.

The present invention concerns a mutant methylglyoxal synthase (MGS) comprising at least one amino acid residue in the protein sequence of the parent enzyme replaced by a different amino acid residue at the same position wherein
    the mutant enzyme has retained more than 50% of the methylglyoxal synthase activity of the parent enzyme and
    the methylglyoxal synthase activity of the mutant MGS is not inhibited by orthophosphate as compared to the parent enzyme.

The invention also concerns a DNA sequence comprising a sequence coding for the mutant MGS of the invention and a microorganism expressing such MGS which activity is not inhibited by orthophosphate, particularly a microorganism comprising a gene coding for the mutant MGS of the invention.

BRIEF DESCRIPTION OF THE DRAWINGS

FIGS. 1-3 depict embodiments of the present invention as described herein.

DETAILED DESCRIPTION OF A PREFERRED EMBODIMENT

In the present application, terms are employed with their usual meaning, except when precised otherwise.

Microorganisms

A "microorganism" means all kind of unicellular organisms, including procaryotic organisms like bacteria, and eucaryotic organisms like yeasts. Preferentially, the microorganism is selected among the group consisting of bacteria, yeasts and fungi, more preferentially selected among Enterobacteriaceae, Bacillaceae, Streptomycetaceae, Clostridiaceae and Corynebacteriaceae. More preferentially, the microorganism is a species of *Escherichia*, *Klebsiella*, *Pantoea*, *Salmonella*, *Bacillus*, *Streptomyces*, *Clostridium* or *Corynebacterium*. Even more preferentially, the microorganism is selected among the group consisting of *Escherichia coli*, *Klebsiella pneumoniae*, *Thermoanaerobacterium thermosaccharolyticum*, *Clostridium sphenoides* or *Saccharomyces cerevisiae*.

As used herein, the term "modified microorganism" or "modified" or "recombinant" refer to a host cell that has a modification of its genome, e.g., as by addition of nucleic acid not naturally occurring in the organism or by a modification of nucleic acid naturally occurring in the host cell.

A "microorganism modified for an improved production of the biochemical selected among lactic acid, acetol and 1,2-propanediol" is a microorganism in which pathways to favour the production of the desired biochemical by conversion of a simple source of carbon have been modified. The microorganism modified for such improved production produces more of the desired biochemical than a native, unmodified microorganism.

Figure 2:
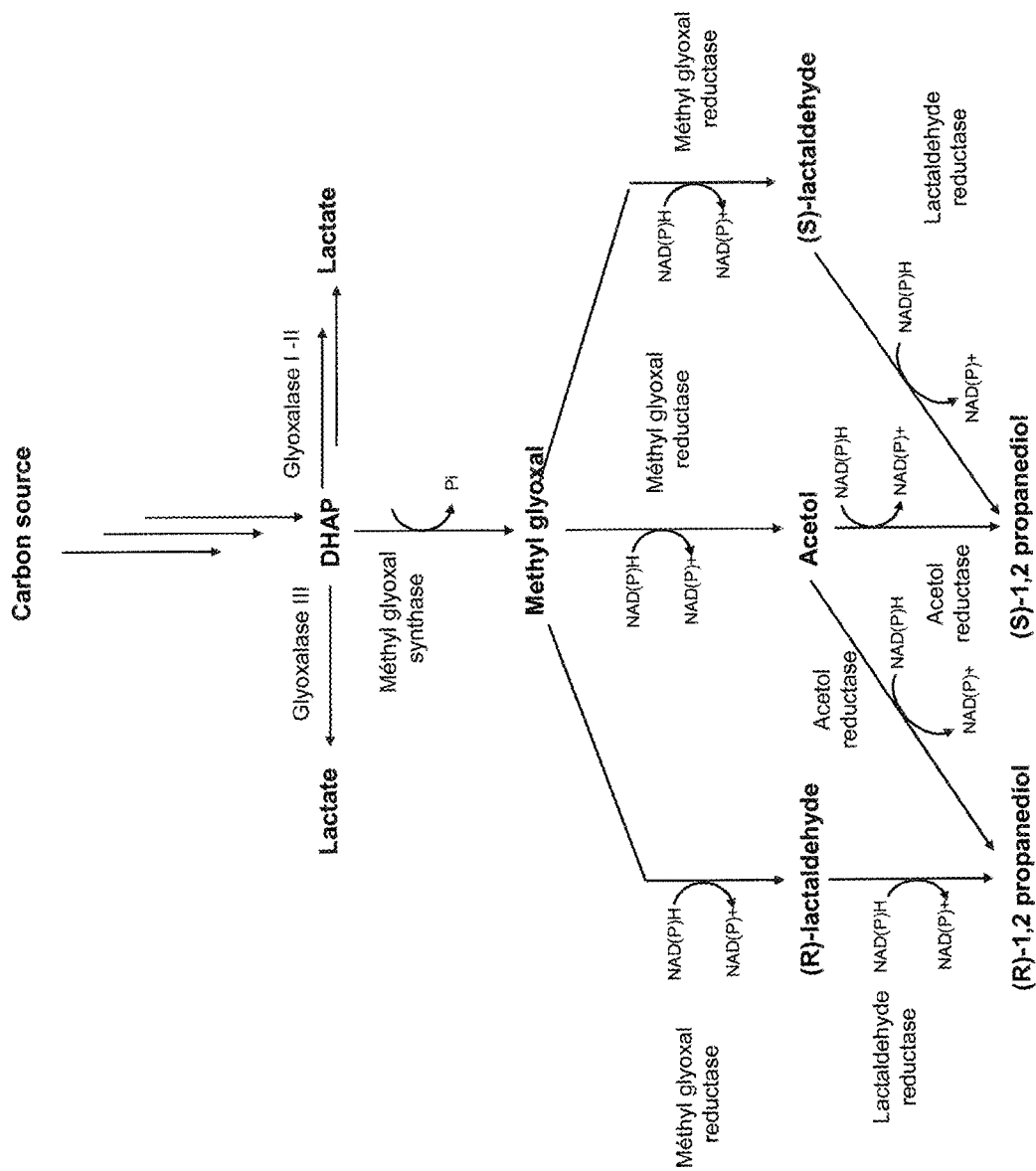

The preferred biosynthetic pathways for the production of lactic acid, acetol and propanediol with the microorganism of the invention are represented on FIG. 2. The person skilled in the art shall identify the enzymatic activities related to the pathway to be promoted and the other enzymatic activities to be attenuated.

Microorganisms modified for the improved production of lactic acid, acetol and propanediol by conversion of methylglyoxal are also disclosed in Cameron et al, 1998, Bennett and San, 2001, Ko et al, 2005 and WO 99/28481, WO 98/37204, WO 2005/073364, WO 2008/116852, WO 2008/116848, WO 2008/116849, WO 2008/116851, PCT/EP2009/053093, which content is incorporated herein by reference.

In the case of yeasts, the following modifications of the host organism are preferred:

attenuation of expression of at least one of the following genes: TPI1, NDE1, NDE2, GUT2, GPD1, GPD2, PDC1, PDC2, PDC5, PDC6, GLO1 enhancement of expression of GRE3 gene.

In the microorganisms of the invention, the DNA sequence coding for a mutant MGS of the invention may be introduced in a vector for the expression and translation of the mutant MGS. It can also be integrated in the chromosome of the said microorganism.

Integration of the DNA sequence can be done either entirely, or simply by introducing in the native gene of the microorganism, the mutation in the coding sequence by replacing the nucleotide(s) coding for the amino acid to be changed by the nucleotide(s) coding for the amino acid of the mutated protein.

Total, partial or specific nucleotides replacement in a gene of a microorganism is well known in the art of genetic engineering, including Sambrook J et al., Molecular cloning: a laboratory manual, Cold Spring Harbour Press, New York (2001), Ausubel F M et al., Current protocols in molecular biology, John Wiley and sons, New York (1999), Adams A et al., Methods in yeast genetics, Cold Spring Harbour Press, New York (1997).

The microorganism of the invention may additionally comprise a gene coding for an YqhD enzyme which catalytic efficiency towards NADPH is increased.

An YqhD enzyme "which catalytic efficiency toward NADPH is increased" means that the catalytic efficiency towards NADPH of the YqhD enzyme expressed in the microorganism is higher than the catalytic efficiency towards NADPH of the native YqhD enzyme of the same microorganism. The catalytic efficiency is defined as the ratio between the catalytic constant (Kcat) and the Michaelis constant (Km). Increase of catalytic efficiency of YqhD enzyme means that the Kcat of the enzyme is increased or that the Km of the enzyme is decreased. In a preferred embodiment the Kcat of the YqhD enzyme is increased and the Km of the YqhD enzyme is decreased.

Preferably, the catalytic efficiency towards NADPH of the YqhD enzyme is higher than the efficiency of the native YqhD enzyme of *E. coli*.

Such enzyme has preferably an enzymatic activity of at least 50% of the activity of the YqhD of *E. coli*, more preferably at least 60% of the activity of the YqhD of *E. coli*.

Particularly, the YqhD enzyme is a mutant YqhDS enzyme wherein the mutant enzyme has retained more than 50% of the YqhD activity of the parent enzyme and the catalytic efficiency toward NADPH of the mutant YqhD is increased as compared with the catalytic efficiency toward NADPH of the parent enzyme.

Preferably the mutant YqhD comprises at least a mutation selected among the group consisting of G149E, G149S and A286T, and combinations thereof. The aminoacids positions are given by reference to the YqhD sequence of *E. coli*. The person skilled in the art shall find the corresponding aminoacids in sequences from other organisms by standard techniques of sequence alignment.

The microorganism of the invention may additionally comprise a gene coding for a glycerol dehydrogenase (GlyDH) enzyme with reduced inhibition of its activity by NAD+ and/or its substrate and/or its product.

"The inhibition of which activity by NAD+ and/or its substrate and/or its product is reduced" means that the inhibition of the activity of the GlyDH enzyme expressed in the microorganism is less inhibited than the activity of the native GlyDH enzyme of the same microorganism. The inhibition of the activity of the GlyDH enzyme can be defined by the Inhibition Concentration 50 (IC50) or the Inhibition Constant (Ki) or any other techniques known by the skilled person. The reduced inhibition of the activity of the GlyDH enzyme means that the IC50 or the Ki of the GlyDH enzyme of the invention is higher than the IC50 or the Ki of the native GlyDH enzyme. The skilled person knows the relation between IC50 and Ki and their meaning on the activity of enzyme among the classic Michaelis-Menten kinetics.

Preferably, the activity of the GlyDH enzyme is less inhibited than the native GlyDH enzyme of *E. coli*. In a preferred embodiment, the enzyme activity is less inhibited for at least two members of the group consisting of NAD+, the enzyme's substrate and the enzyme's product. More preferably the enzyme activity is less inhibited by the three of NAD+, its substrate and its product.

The enzyme "substrate" is dihydroxyacetone, hydroxyacetone, methylglyoxal, lactaldehyde, glyceraldehyde, glycolaldehyde and derivatives thereof.

The enzyme "product" is the molecule obtained from the selected substrate by reduction of the carbonyl function.

For the production of 1,2-propanediol, the substrate is hydroxyacetone and the product is 1,2-propanediol.

Particularly the GlyDH enzyme is a mutant enzyme, wherein
 the mutant enzyme has retained more than 50% of the activity of the parent enzyme and
 the glycerol dehydrogenase activity of the mutant GlyDH is less inhibited by NAD+ and/or by its substrate as compared to the parent enzyme and/or by its product as compared to the parent enzyme.

Preferably, the mutant GlyDH preferably comprises at least a mutation selected among the group consisting of A160T and T120N, and combinations thereof. The aminoacids positions are given by reference to the GldA sequence of E. coli. The person skilled in the art shall find the corresponding aminoacids in sequences from other organisms by standard techniques of sequence alignment.

Methylglyoxal Synthase (MGS) Enzyme

The invention concerns a methylglyoxal synthase (MGS) which activity is not inhibited by orthophosphate a microorganism comprising the same and a method for the production of a desired biochemical by fermentation of said microorganism on a culture medium comprising a simple source of carbon.

"Not inhibited by orthophosphate" or "lacking inhibition by orthophosphate" means that no inhibition by orthophosphate is identified in an activity assay, when activity of the enzyme is studied in presence of orthophosphate. Such an activity assay is well known in the art and can be carried out as disclosed in Example 2.

In addition, kinetics of the MGS enzyme of the invention follows Michaelis-Menten kinetics regardless of the presence or absence of orthophosphate. Kinetics of the native enzyme follow a Michaelis-Menten model only in the absence of orthophosphate. The presence of orthophosphate makes the kinetic profile (specific activity over substrate concentration) of the native enzyme to become sigmoidal, which denotes the allosteric inhibition by orthophosphate.

Such enzyme has preferably a methylglyoxal synthase activity of at least 50% of the activity of the methylglyoxal synthase of E. coli.

The enzymes may be obtained by various ways known to the person skilled in the art.

A first approach consists in screening native enzymes of various organisms for their lack of inhibition by orthophosphate.

A second approach consists in inducing mutation(s) in enzymes of known organisms and selecting the enzymes for their lack of inhibition by orthophosphate. Mutations may be induced by methods known in the art such as subjecting the microorganism to mutagenic agents. Another method to induce mutations is to growth the microorganism under selection pressure, with high levels of orthophosphate and identify the microorganism growing under such conditions and select the enzymes obtained for their lack of inhibition by orthophosphate.

Other methods are also known in the art to obtain mutations by shuffling DNA from various origins and select the proteins encoded by the shuffled DNA so obtained based on their methylglyoxal synthase activity and their lack of inhibition by orthophosphate.

In a particular embodiment of the invention, the inventors obtained several mutants MGS retaining their methylglyoxal synthase activity and lacking inhibition by orthophosphate by selecting strains modified for an improved production lactic acid, acetol and/or 1,2-propanediol cultured under selection pressure as disclosed in WO 2005/073364 and as shown in Example 1.

The invention concerns particularly mutant methylglyoxal synthase (MGS) comprising at least one amino acid residue in the protein sequence of the parent enzyme replaced by a different amino acid residue at the same position wherein
 the mutant enzyme has retained more than 50% of the activity of the parent enzyme and
 the methylglyoxal synthase activity of the mutant MGS is not inhibited by orthophosphate as compared to the parent enzyme.

"Mutant" means that a mutation was introduced in a protein sequence by a person. According to the invention, a mutant enzyme is an enzyme comprising at least one amino acid difference with a parent enzyme. In the mutant enzyme of the invention, any change in amino acids may be introduced, either by directed mutagenesis or random mutagenesis, but also using chimerical enzymes comprising parts of a second enzyme replacing corresponding parts of the parent enzyme.

The "parent enzyme" is the enzyme prior mutation. The parent enzyme may be of any origin, natural, isolated from another organism or synthetic.

The method for determining that the mutated MGS has retained "more than 50%" is well known in the art and disclosed in Example 2.

Indeed, the skilled person shall choose the level of desired activity according to the final use of mutant MGS. Indeed, when a high activity is necessary, the skilled person will choose a mutant having more that 80% of activity, compared to the non mutated parent enzyme, more preferably more that 90% of activity. In other cases, selecting a mutant MGS with an activity around and above 50% compared to the parent enzyme may prevent additional modifications in a microorganism, like modifying the promoter to lower the level of expression of the enzyme.

The inventors found that in a medium comprising up to 3 mM orthophosphate, the enzymatic activity of the mutant enzyme is not inhibited by orthophosphate when the corresponding parent enzyme is inhibited. The amount of orthophosphate was chosen provided that the enzymatic reaction generally occurs in a microorganism.

According to the invention, "not inhibited by orthophosphate as compared to the parent MGS" is understood to be at orthophosphate concentrations compatible with the concentrations of orthophosphate in a microorganism growing on a medium comprising orthophosphate at concentrations compatible with the growth of the microorganism.

In a preferred embodiment, the mutant MGS of the invention comprises at least one amino acid residue of an identified region in the native parent MGS replaced by a different amino acid residue at the same position.

The inventors have identified mutants wherein at least one amino acid residue of one of the following Conserved Regions (CR) in the native parent MGS has been replaced by a different amino acid residue at the same position, the three Conserved Regions CR1, CR2 and CR3 being identified below:

-Xa1-Leu-Xa2-Xa3-His-Asp-Xa4-Xa5-Lys-(CR1)

wherein
Xa1 represents Ala and Val, preferably Ala,
Xa2 represents Val and Ile,
Xa3 represents Ala and Ser, preferably Ala,
Xa4 represents Ala, Arg, Asn, Gln, Glu, His, Lys, Met and Ser, preferably His and Lys, and Xa5 represents Arg, Cys, Gln, Lys, Met and Tyr, preferably Cys and Lys -Asp-Xa6-Xa7-Xa8-Xa9-X10-X11-His-X12-X13-Asp-X14-(CR2)

wherein
Xa6 represents Asp and Pro, preferably Pro,
Xa7 represents Leu and Met, preferably Leu,
Xa8 represents Asn, Glu, Ser and Thr, preferably Asn and Thr,
Xa9 represents Ala, Asn, Pro, Ser and Val, preferably Ala,
X10 represents Ala, Leu, Gln, Lys, Met and Val, preferably Gln and Val,
X11 represents Ala and Pro, preferably Pro,
X12 represents Asp and Glu,
X13 represents Ala, Pro and Val, preferably Pro, and
X14 represents Ile and Val, preferably Val X15-X16-X17-X18-Pro-X19-X20-X21-X22-(CR3)

wherein
X15 represents Ile, Leu and Val, preferably Val,
X16 represents Arg, Gln, His, Trp and Tyr, preferably Trp and Tyr,
X17 represents Ala, Asn, Arg, Asp, Gln, Glu, Gly, Lys and Ser, preferably Asn,
X18 represents Ile, Leu and Val, preferably Ile,
X19 represents Cys, His, Ile, Leu, Met and Val, preferably Leu and Val,
X20 represents Ala and Val, preferably Ala,
X21 represents Cys, Ile, Leu, Met and Thr, preferably Thr, and
X22 represents Asn and Thr, preferably Asn.

These conserved regions can be identified in different MGS enzymes by simple sequence alignment using standard sequence alignment tools such as ClustalW2, Kalign, MAFFT, MUSCLE or T-coffee, all available on the website www.ebi.ac.uk. A sequence alignment of several MGS of different species is given in FIG. 1.

Amino acids numbers in the present application are given by reference to the proteins of *E. coli*.

It can be found in FIG. 1 that CR1 correspond to amino acids 15 to 23 of *E. coli* MGS, CR2 correspond to amino acids 91 to 102 of *E. coli* MGS and CR3 correspond to amino acids 111 to 119 of *E. coli* MGS.

According to the invention, the mutant MGS can have at least one mutation in one of CR1, CR2 or CR3. It can have at least two mutations in CR1 and CR2, in CR1 and CR3 or in CR2 and CR3. It can also have at least three mutations in CR1, CR2 and CR3.

"At least" in such context means that the mutated enzyme may have other mutations, but nor related to the identified Conserved Regions CR1, CR2 and CR3. These other non identified mutations have no substantial impact on the mutated enzyme of the invention, provided that:
- the mutant enzyme has retained more than 50% of the methylglyoxal synthase activity of the parent enzyme and
- the methylglyoxal synthase activity of the mutant MGS is not inhibited by orthophosphate as compared to the parent enzyme.

In preferred embodiments, the amino acid residue in the Conserved Regions CR1 to CR3 in the parent MGS replaced by a different amino acid residue at the same position in the mutant MGS is selected among the group consisting of amino acid Xa4 in CR1, amino acid Xa9 in CR2 and amino acid X19 in CR3 and combinations thereof (CR1 & CR2, CR1 & CR3, CR2 & CR3 and CR1 & CR2 & CR3).

Xa4 correspond to amino acid 21 in the MGS sequence of *E. coli*. Xa9 corresponds to amino acid 95 in the MGS sequence of *E. coli*. X19 corresponds to amino acid 116 in the sequence of *E. coli*.

Particularly, the mutated MGS of the invention comprises at least one of the mutations selected among the group consisting in H21Q, A95V, V116L, and combinations thereof, the aminoacid positions being given by reference to the MGS sequence of *E. coli*.

More preferably, the mutated MGS of the invention comprises at least one of the following amino acid sequence in conserved regions CR1 to CR3
CR1: Ala Leu Val Ala His Asp Gln Cys Lys
CR2: Asp Pro Leu Asn Val Val Pro His Asp Pro Asp Val
CR3: Val Trp Asn Ile Pro Leu Ala Thr Asn
the amino acid residue marked in bold and underlined corresponding to the amino acid in the mutant MGS different from the amino acid in the parent MGS.

Particularly, the mutant MGS of the invention has at least 50% sequence identity compared to the MGS sequence of *E. coli*, provided that it comprises at least one of the following mutations in CR1 and/or CR2:
CR1: Ala Leu Val Ala His Asp Gln Cys Lys
CR2: Asp Pro Leu Asn Val Val Pro His Asp Pro Asp Val
CR3: Val Trp Asn Ile Pro Leu Ala Thr Asn.

Sequence identity is defined after sequence alignment of the MGS sequence of *E. coli* with the protein sequence to be compared using CLUSTALW2 available on the EBI website (see above) with default parameters. The sequence identity is then calculated with the sequence alignment by the ratio of the number of identical amino acids at the same position with the total number of amino acids in the reference sequence (*E. coli*).

Preferably, the mutant MGS has at least 70% sequence identity.

In most preferred embodiments, the mutant MGS of the invention comprises the sequence selected among the group consisting of MGS identified in SEQ ID NO 1, SEQ ID NO 2 and SEQ ID NO 3.

DNA, Vectors, Genes

The present invention also concerns a DNA sequence comprising a sequence coding for the mutant MGS of the invention. The sequence coding for the mutant MGS of the invention is not a limiting factor by itself. The skilled person can easily obtain the sequence of a native MGS from a microorganism and introduce in the coding sequence the mutation(s) to be introduced in the protein by changing one or more appropriate nucleotide.

The skilled person can also perform a mutagenesis in the sequence of a microorganism, and isolate the mutated DNA sequence by standard methods.

Mutations can be introduced by site-directed mutagenesis by usual methods like Polymerase Chain Reaction (PCR, see Sambrook J et al., Molecular cloning: a laboratory manual, Cold Spring Harbour Press, New York (2001), Ausubel F M et al., Current protocols in molecular biology, John Wiley and sons, New York (1999), Adams A et al., Methods in yeast genetics, Cold Spring Harbour Press, New York (1997)), or by random mutagenesis techniques, such as use of mutagenic agents (Ultra-Violet rays or chemical agents like nitrosoguanidine (NTG) or ethylmethanesulfonate (EMS)) or use of PCR techniques (DNA shuffling or error-prone PCR).

The person skilled in the art can also prepare synthetic genes with preferred codons selected for an improved expression in a specific organism. Codons usages by various organisms are well known in the art and several companies are proposing the manufacture of synthetic genes with codon optimization.

The sequence of the invention can be isolated, consisting in the coding sequence as defined above, or within a gene comprising regulatory elements upstream and downstream the coding sequence for its expression in a specific organism.

The sequence can also be present in a vector, for its replication (replication vector) or for the expression and translation of the mutated protein of the invention in a microorganism (expression vector). Such vectors are known in the art and not a limiting factor for the definition of the invention.

Said genes and vectors are also part of the invention.

Preferably, the DNA sequence of the invention is in a microorganism with regulatory elements allowing expression and translation of the mutated MGS of the invention.

Production of Lactic Acid, Acetol, or 1,2-Propanediol

The invention also concerns a method for the production of a biochemical selected among lactic acid, acetol and 1,2-propanediol by fermentation comprising culturing a microorganism of the invention, modified for an improved production of lactic acid, acetol and/or 1,2-propanediol and recovery of the biochemical.

In a particular embodiment, the recovered lactic acid and/or acetol and/or 1,2-propanediol is purified.

Methods for the purification of lactic acid, acetol and 1,2-propanediol are known in the art and described in Datta and Henry, 2006, Wasewar, 2005, U.S. Pat. No. 5,076,896 and WO 2007/074066.

Advantageously, the production is done by fermentation in a batch, fed-batch or continuous process, according to processes known to the person skilled in the art of microorganisms fermentation. Preferably, the production is done by fermentation in a fed-batch process.

Culture Medium and Carbon Source

In the production method of the invention, the microorganism is cultured on an appropriate culture medium.

An "appropriate culture medium" means a medium of known molecular composition adapted to the growth of the micro-organism. In particular, said medium contains at least a source of phosphorus and a source of nitrogen. Said appropriate medium is for example a mineral culture medium of known set composition adapted to the bacteria used, containing at least one carbon source. Said appropriate medium may also designate any liquid comprising a source of nitrogen and/or a source of phosphorus, said liquid being added and/or mixed to the source of sucrose. In particular, the mineral growth medium for Enterobacteriaceae can thus be of identical or similar composition to M9 medium (Anderson, 1946), M63 medium (Miller, 1992) or a medium such as defined by Schaefer et al. (1999).

The carbon source 'glucose' can be replaced in this medium by any other carbon source, in particular by sucrose or any sucrose-containing carbon source such as sugarcane juice or sugar beet juice.

A "carbon source" or "carbon substrate" means any carbon source capable of being metabolized by a microorganism wherein the substrate contains at least one carbon atom.

Preferably, the carbon source is selected among the group consisting of glucose, sucrose, mono- or oligosaccharides, starch or its derivatives or glycerol and mixtures thereof.

Indeed the microorganisms used in the method of the present invention can be modified to be able to grow on specific carbon sources when the non modified microorganism cannot grow on the same source of carbon, or grow at to low rates. These modifications may be necessary when the source of carbon is a byproduct of biomass degradation such as by-products of sugarcane including; filter cake from clarification of raw juice and different kind of molasses.

FIG. 1 represents the alignment of 36 protein sequences of MGS of various sources. The sequences MGSA TRESO (SEQ ID NO:53); MGSA COXBU (SEQ ID NO:54); MGSA RALSO (SEQ ID NO:55); MGSA BURMA (SEQ ID NO:56); MGSA BRUME (SEQ ID NO:57); MGSA AGRT5 (SEQ ID NO:58); MGSA RHIME (SEQ ID NO:59); MGSA SMYTH (SEQ ID NO:60); MGSA BORBU (SEQ ID NO:61); MGSA BORGA (SEQ ID NO:62); MGSA CLOPE (SEQ ID NO:63); MGSA OCEIH (SEQ ID NO:64); MGSA THETN (SEQ ID NO:65): MGSA CLOTS (SEQ ID NO:66); MGSA GEOKA (SEQ ID NO:67); MGSA BACCR (SEQ ID NO:68); MGSA BACSK (SEQ ID NO:69); MGSA BACHD (SEQ ID NO:70); MGSA BACSU (SEQ ID NO:71); MGSA ENTFA (SEQ ID NO:72); MGSA LISIN (SEQ ID NO:73); MGSA HAEIN (SEQ ID NO:74); MGSA PHOPR (SEQ ID NO:75); MGSA VIBVU (SEQ ID NO:76); MGSA VIBCH (SEQ ID NO:77); MGSA VIBPA (SEQ ID NO:78); MGSA PHOLL (SEQ ID NO:79); MGSA YERPE (SEQ ID NO:80); MGSA ERWCT (SEQ ID NO:81); MGSA ECOL6 (SEQ ID NO:82); MGSA SALTI (SEQ ID NO:83); MGSA MANSM (SEQ ID NO:84); MGSA PASMU (SEQ ID NO:85); MGSA CLOAB (SEQ ID NO:86); MGSA THEMA (SEQ ID NO:87); and MGSA LEPIC (SEQ ID NO:88) were obtained from the UniProt Knowledge Base (The UniProt consortium (2008)) and the alignment made using MUSCLE with default parameters.

FIG. 2 represents the metabolic pathways for the production of lactic acid, acetol and 1,2-propanediol in the microorganisms of the invention.

Figure 3:
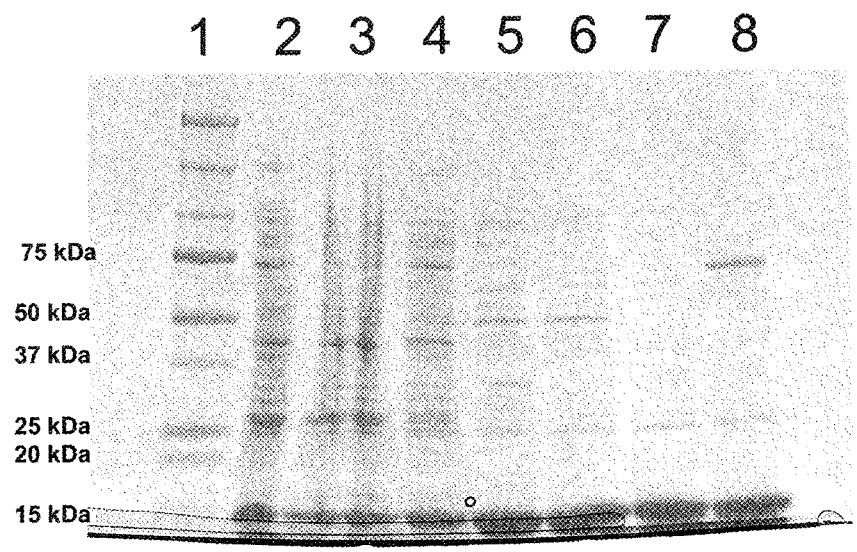

FIG. 3 represents the analysis on SDS 4-15% gradient polyacrylamide gel the different purification steps of the protein mgsA* V116L. Lane 1: Molecular weight marker, Lane 2: Crude extract, Lane 3, supernatant of the $1^{st}$ ammonium sulphate precipitation, Lane 4, pellet of the $2^{nd}$ ammonium sulphate precipitation, Lane 5, Resource Q pool, Lane 6, MonoQ pool, Lane7, superdex 200 pool, Lane 8, final pool with the BSA.

EXAMPLES

Example 1

Evolution of 3 Modified Strains of *E. coli* MG1655 in Chemostat Culture and Identification of 3 Mutant MGS Enzymes in the Evolved Clones The construction of the strains *E. coli* MG1655 lpd* ΔtpiA, ΔpflAB, ΔadhE, ldhA::Km, ΔgloA, ΔaldA, ΔaldB, Δedd (strain 1), *E. coli* MG1655 lpd* ΔtpiA, ΔpflAB, ΔadhE, ΔldhA::Cm, ΔgloA, ΔaldA, ΔaldB, Δedd (strain 2) and *E. coli* MG1655 lpd* ΔtpiA, ΔpflAB, ΔadhE, ΔldhA, ΔgloA, ΔaldA, ΔaldB, Δedd, ΔarcA, Δndh::Km (strain 3) were previously described in patent application WO 2005/073364 for strain 1 and in patent application WO 2008/116852 for strains 2 and 3.

To evolve them toward improved 1,2 propanediol production, the 3 strains were cultivated in continuous culture, either under anaerobic conditions, or under microaerobic conditions (1% oxygen) in the culture medium MPG (given in patent application WO 2008/116852) with 0.42 or 0.84 g/l sodium nitrate, with excess glucose (from 20 g/l initially with addition if the glucose becomes exhausted). The temperature was set at 37° C., the pH was regulated at 6.5 by addition of base and the dilution rate of the chemostat was set between 0.04 $h^{-1}$ and 0.08 $h^{-1}$. The evolution of the strain in the chemostats was followed by the increase of the biomass concentration coupled with the increase of the concentrations of the product, 1,2-propanediol and the co-product acetate, over several weeks. This denoted the improvement of the performances of the strains. When the cultures reached a steady state with no further increase of the concentrations under these conditions, the evolution was done.

The characteristics of the strains before and after evolution were assessed. Single colonies representing individual clones were isolated on Petri dishes. These clones were assessed using the initial strain as control in an Erlenmeyer flask assay, using the same medium MPG used in the chemostat culture, but buffered with MOPS. Among these clones, several presented better 1,2-propanediol specific production rates as compared to the control. The results obtained on the best clone for each condition of evolution are reported in Table 1 to 3 below.

TABLE 1

Comparison of the best evolved clone obtained after 81 days of evolution under anaerobic conditions with the initial strain

| Strain E. coli MG1655 Ipd* ΔtpiA ΔpflAB ΔadhE ldhA::Km ΔgloA Δald, ΔaldB Δedd (Strain 1) | Initial strain before evolution (performances measured after 2 days of culture) | Best evolved clone (performances measured after 2 days of culture) |
|---|---|---|
| Glucose specific consumption rate (g glucose/g biomass/h) | 0.13 | 0.18 (+38%) |
| 1,2-propanediol specific production rate (g 1,2-propanediol/g biomass/h) | 0.02 | 0.06 (+200%) |
| 1,2-propanediol + hydroxyacetone specific production rate (g 1,2-propanediol + hydroxyacetone/g biomass/h) | 0.04 | 0.06 (+50%) |

TABLE 2

Comparison of the best evolved clone obtained after 66 days of evolution under anaerobic conditions with the initial strain

| Strain E. coli MG1655 Ipd* ΔtpiA ΔpflAB ΔadhE ΔldhA::Cm ΔgloA Δald, ΔaldB Δedd (Strain 2) | Initial strain before evolution (performances measured after 2 days of culture) | Best evolved clone (performances measured after 2 days of culture) |
|---|---|---|
| Glucose specific consumption rate (g glucose/g biomass/h) | 0.12 | 0.21 (+75%) |
| 1,2-propanediol specific production rate (g 1,2-propanediol/g biomass/h) | 0.02 | 0.07 (+250%) |
| 1,2-propanediol + hydroxyacetone specific production rate (g 1,2-propanediol + hydroxyacetone/g biomass/h) | 0.04 | 0.08 (+100%) |

TABLE 3

Comparison of the best evolved clone obtained after 132 days of evolution under microaerobic conditions with the initial strain

| Strain E. coli MG1655 Ipd* ΔtpiA ΔpflAB ΔadhE ΔldhA::Cm ΔgloA Δald, ΔaldB, Δedd, ΔarcA Δndh (Strain 3) | Initial strain before evolution (performances measured after 2 days of culture) | Best evolved clone (performances measured after 2 days of culture) |
|---|---|---|
| Glucose specific consumption rate (g glucose/g biomass/h) | 0.15 | 0.28 (+87%) |

TABLE 3-continued

Comparison of the best evolved clone obtained after 132 days of evolution under microaerobic conditions with the initial strain

| Strain E. coli MG1655 Ipd* ΔtpiA ΔpflAB ΔadhE ΔldhA::Cm ΔgloA Δald, ΔaldB, Δedd, ΔarcA Δndh (Strain 3) | Initial strain before evolution (performances measured after 2 days of culture) | Best evolved clone (performances measured after 2 days of culture) |
|---|---|---|
| 1,2-propanediol specific production rate (g 1,2-propanediol/g biomass/h) | 0.00 | 0.10 |
| 1,2-propanediol + hydroxyacetone specific production rate (g 1,2-propanediol + hydroxyacetone/g biomass/h) | 0.04 | 0.10 (+150%) |

Specific genes involved in the terminal 1,2-propanediol biosynthetic pathway were sequenced in the 3 best evolved clones of strain 1, strain 2 and strain 3. For each clone, one mutated mgsA gene was identified resulting in expression of mutated MGS protein: MgsA*(A95V) (SEQ ID NO 1) for evolved clone of strain 1, MgsA*(H21Q) (SEQ ID NO 2) for evolved clone of strain 2 and MgsA*(V116L) (SEQ ID NO 3) for evolved clone of strain 3.

Example 2

Production, Purification and Characterization of Native MGS and 3 Mutant MGS (H21Q, A95V & V116L)

1. Construction of the Strains for Production of MGS Proteins
    1.1. Construction of the Plasmid for Overexpression of mgsA:pETTOPO-mgsA The plasmid was built to obtain the overexpression of the native protein (without His-tag). The gene mgsA (sequence 1025780-1026238) was PCR amplified from genomic DNA of E. coli MG1655 using the following oligonucleotides:

pETTOPO mgsA F (consisting of 24 pb):

cacc<u>atggaactgacgactcgca</u>, (SEQ ID NO 4)

with
   a region (underlined letters) homologous to the sequence (1026238-1026220) of the gene mgsA.
   a region (bold) for directional cloning of the fragment in the plasmid pET101.
and
   pETTOPO-N mgsA R. (consisting of 23 pb)

<u>Ttacttcagacggtccgcgagat</u> (SEQ ID NO 5)

with a region (underlined letters) homologous to the sequence (1025780-1025802) of the gene mgsA.
The fragment amplified was directly cloned into the pET101 from the "Champion pET Directional TOPO Expression Kits" (Invitrogen®). The plasmid built was named pET-TOPO-mgsA.
    1.2. Construction of the Plasmids for the Overexpression of mgsA*

The three mutant MGS bear the mutations H21Q, A95V or V116L. The plasmids for the overexpression of the three mutant proteins were built by directed mutagenesis in the plasmid pETTOPO-mgsA using Quickchange site-directed mutagenesis kit from Stratagene®. with the oligonucleotides given in Table 4.

TABLE 4

Oligonucleotides used for the site-directed mutagenesis of mgsA

| mutant | Names of oligos | Sequence of the oligonucleotide | Modification to create mutation | Homologous to the sequence |
|---|---|---|---|---|
| A95V | mgsA*A95VmutDir5' | ttctgggatccactaaatgTcgtgccgca cgatcctgacgtCaaagcc (SEQ ID NO 6) | Red capital letter: T instead of C to create A95V mutation Green capital letter: C instead of G to create AatII restriction site without change in protein sequence | 1025974 to 1025927 |
|  | mgsA*A95VmutDir3' | ggctttGacgtcaggatcgtgcggcacg Acatttagtggatcccagaa (SEQ ID NO 7) | Red capital letter: A instead of G to create A95V mutation Green capital letter: C instead of G to create AatII restriction site without disturbing without change in protein sequence |  |
| V116L | mgsA*V116LmutDir5' | cgacggtatggaacattccgCtcgcG accaacgtggcaacg (SEQ ID NO 8) | Red capital letter: C instead of G to create V116L mutation Green capital letter: G instead of C to create NruI restriction site without change in protein sequence | 1025914 to 1025873 |
|  | mgsA*V116LmutDir3' | cgttgccacgttggtCgcgaGcggaatg ttccataccgtcgc (SEQ ID NO 9) | Red capital letter: G instead of C to create V116L mutation Green capital letter: C instead of G to create NruI restriction site without change in protein sequence |  |
| H21Q | mgsA* H21Q mut dir F | ctggtggcacacgatcaAtgcaaacaG atgctgatgagctgggtg (SEQ ID NO 10) | Red capital letter: A instead of C to create V116L mutation Green capital letter: G instead of A to create AlwNl restriction site without change in protein sequence | 1026193 to 1026149 |
|  | mgsA* H21Q mut dir R | cacccagctcatcagcatCtgtttgcaTt gatcgtgtgccaccag (SEQ ID NO 11) | Red capital letter: T instead of G to create V116L mutation Green capital letter: C instead of T to create AlwNl restriction site without change in protein sequence |  |

The 3 plasmids obtained were named pETTOPO-mgsA*(A95V), pETTOPO-mgsA*(V116L) and pETTOPO-mgsA*(H21Q).

1.3. Construction of BL21 Star (DE3) ΔmgsA::Cm

To avoid the mix between the mutant proteins expressed by the plasmid and the wild-type one expressed by chromosome, the strain used to carry out the overexpression was deleted for the mgsA gene.

1.3.1. Construction of the Strain MG1655 ΔmgsA::Cm

The gene mgsA was inactivated in strain *E. coli* MG1655 by inserting a chloramphenicol antibiotic resistance cassette and deleting most of the gene concerned according to in Protocol 1.

Protocol 1:

Introduction of a PCR Product for Recombination and Selection of the Recombinants (FRT System).

The oligonucleotides chosen and given in Table 5 for replacement of a gene or an intergenic region were used to amplify either the chloramphenicol resistance cassette from the plasmid pKD3 or the kanamycin resistance cassette from the plasmid pKD4 (Datsenko, K. A. & Wanner, B. L. (2000)). The PCR product obtained was then introduced by electroporation into the recipient strain bearing the plasmid pKD46 in which the system λ Red (γ, β, exo) expressed greatly favours homologous recombination. The antibiotic-resistant transformants were then selected and the insertion of the resistance cassette was checked by PCR analysis with the appropriate oligonucleotides given in Table 6.

If they are other modifications in the strain, they were checked with the oligonucleotides given in Table 6.

The resulting strain was named *E. coli* MG1655 ΔmgsA::Cm

TABLE 5

Oligonucleotides used for replacement of a chromosomal region by recombination with a PCR product

| Region name | Names of oligos | Homology with chromosomal region |
|---|---|---|
| mgsA | DmgsA F | 1026273 to 1026193 |
|  | DmgsA R | 1025837 to 1025758 |
| edd-eda | DedaR | 1930144 to 1930223 |
|  | DeddF | 1932501 to 1932582 |
| aldA | DaldAR | 1487615 to 1487695 |
|  | DaldAF | 1486256 to 1486336 |
| aldB | DaldBR | 3754534 to 3754455 |
|  | DaldBF | 3752996 to 3753075 |
| arcA | DarcAF | 4637868 to 4637791 |
|  | DarcAR | 4637167 to 4637245 |
| Ndh | DndhF | 1165071 to 1165149 |
|  | DndhR | 1166607 to 1166528 |
| Ptrc01-gapA | Ptrc-gapAF | 1860800 to 1860762 |
|  | Ptrc-gapAR | 1860478 to 1860536 |
| gldA | DgldA F | 4137058 to 4136979 |
|  | DgldA R | 4135955 to 4136034 |
| gloA | DgloA F | 1725861 to 1725940 |
|  | DgloA R | 1726268 to 1726189 |
| yqhD | DyqhDF | 3153377 to 3153456 |
|  | DyqhDR | 3154540 to 3154460 |
| Dld | Ddld F | 2220207 to 2220288 |
|  | Ddld R | 2221919 to 2221838 |
| lldD | DlldP F | 3777860 to 3777941 |
|  | DlldP R | 3779040 to 3778961 |

TABLE 6

Oligonucleotides used for checking the insertion of resistance cassette or the loss of resistance cassette

| Region name | Names of oligos | Homology with chromosomal region |
|---|---|---|
| mgsA gene | helD F | 1025242 to 1025260 |
|  | yccT R | 1026499 to 1026480 |
| edd-eda genes | edaR | 1929754 to 1929777 |
|  | eddF | 1932996 to 1932968 |
| aldA gene | aldAF | 1485877 to 1485901 |
|  | aldAR | 1487714 to 1487689 |
| aldB gene | aldBF | 3752056 to 3752095 |
|  | aldBR | 3754644 to 3754674 |
| arcA gene | arcAF | 4638292 to 4638273 |
|  | arcAR | 4636854 to 4636874 |
| ndh gene | ndhF | 1164722 to 164742 |
|  | ndhR | 1167197 to 1167177 |
| Ptrc01-gapA | yeaAF | 1860259 to 1860287 |
|  | gapAR | 1861068 to 1861040 |
| gldA gene | talC F | 4137144 to 4137121 |
|  | yijF R | 4135136 to 4135159 |
| gloA gene | gloAF2 | 1725641 to 1725660 |
|  | gloAR2 | 1726450 to 1726431 |
| yqhD gene | yqhDF | 3153068 to 3153100 |
|  | yqhDR | 3154825 to 3154797 |
| dld gene | dld F | 2219708 to 2219729 |
|  | dld R | 2222343 to 2222323 |
| lldD gene | lldP F | 3777394 to 3777414 |
|  | lldP R | 3779406 to 3779384 |
| mgsA::Km | helDF | 1025242 to 1025260 |
|  | mgsA R3 | 1026734 to 1026715 |

1.3.2. Construction of the Strain BL21 Star (DE3) ΔmgsA::Cm The deletion of the gene mgsA by replacement of the gene by a chloramphenicol resistance cassette in the strain *E. coli* BL21 star (DE3) was performed by the technique of transduction with phage P1.

Protocol 2:

Transduction with Phage P1 for Deletion of a Gene

The deletion of the chosen gene by replacement of the gene by a resistance cassette (kanamycin or chloramphenicol) in the recipient *E. coli* strain was performed by the technique of transduction with phage P1. The protocol was in two steps, (i) the preparation of the phage lysate on the strain MG1655 with a single gene deleted and (ii) the transduction of the recipient strain by this phage lysate.

Preparation of the Phage Lysate

Seeding with 100 μl of an overnight culture of the strain MG1655 with a single gene deleted of 10 ml of LB+Cm 30 μg/ml+glucose 0.2%+CaCl$_2$ 5 mM.

Incubation for 30 min at 37° C. with shaking.

Addition of 100 μl of phage lysate P1 prepared on the wild type strain MG1655 (approx. 1×10$^9$ phage/ml).

Shaking at 37° C. for 3 hours until all cells were lysed.

Addition of 200 μl of chloroform, and vortexing.

Centrifugation for 10 min at 4500 g to eliminate cell debris.

Transfer of supernatant in a sterile tube and addition of 200 μl of chloroform.

Storage of the lysate at 4° C.

Transduction

Centrifugation for 10 min at 1500 g of 5 ml of an overnight culture of the *E. coli* recipient strain in LB medium.

Suspension of the cell pellet in 2.5 ml of MgSO$_4$ 10 mM, CaCl$_2$ 5 mM.

Control tubes: 100 μl cells

100 μl phages P1 of the strain MG1655 with a single gene deleted.

Tube test: 100 μl of cells+100 μl phages P1 of strain MG1655 with a single gene deleted.

Incubation for 30 min at 30° C. without shaking.

Addition of 100 μl sodium citrate 1 M in each tube, and vortexing.

Addition of 1 ml of LB.

Incubation for 1 hour at 37° C. with shaking

Plating on dishes LB+Cm 30 μg/ml after centrifugation of tubes for 3 min at 7000 rpm.

Incubation at 37° C. overnight.

The antibiotic-resistant transformants were then selected and the insertion of the deletion was checked by a PCR analysis with the appropriate oligonucleotides given in Table 6.

The resulting strain was named *E. coli* BL21 star (DE3) ΔmgsA::Cm.

1.4. Introduction of Plasmids in the Strain BL21 Star (DE3) ΔmgsA::Cm

The plasmids pETTOPO-mgsA, pETTOPO-mgsA* (A95V), pETTOPO-mgsA*(V116L), pETTOPO-mgsA* (H21Q) were transformed by electroporation in the strain *E. coli* BL21 star (DE3) ΔmgsA::Cm and the strains obtained were named, respectively:

BL21 star (DE3) ΔmgsA::Cm pETTOPO-mgsA

BL21 star (DE3) ΔmgsA::Cm pETTOPO-mgsA*(A95V)

BL21 star (DE3) ΔmgsA::Cm pETTOPO-mgsA*(V116L)

BL21 star (DE3) ΔmgsA::Cm pETTOPO-mgsA*(H21Q)

2. Production of MGS Proteins

The four strains BL21 star (DE3) ΔmgsA::Cm pETTOPO-mgsA, BL21 star (DE3) ΔmgsA::Cm pETTOPO-mgsA* (A95V), BL21 star (DE3) ΔmgsA::Cm pETTOPO-mgsA* (V116L) and BL21 star (DE3) ΔmgsA::Cm pETTOPO-mgsA*(H21Q) were cultivated at 37° C. under aerobic conditions in 2 l baffled Erlenmeyer flasks with 500 ml LB medium with 2.5 g/l glucose. The flasks were agitated at 200 rpm on an orbital shaker. When the optical density measured at 550 nm reached 0.5 units, the flasks were incubated at 25°

C. When the optical density reached 1.2 units, the production of MGS proteins was induced by adding 500 µM IPTG in the cultures. The biomass was harvested by centrifugation when the cultures reached an optical density above 3.5 units. The supernatant was discarded and the pellet was stored at −20° C. before use.

3. Activity Assay for MGS

A coupled activity assay, adapted from Hopper and Cooper (1972) was used to determine the enzyme activity. Dihydroxyacetone phosphate (DHAP) is converted to methylglyoxal (MG) by MGS. The formation of MG is coupled to the formation of S-D-lactoylglutathione by the non enzymatic formation to the thio hemi-acetal with glutathione and the subsequent isomerisation of the complex by glyoxalase I. The rate of increase in absorbance at 240 nm, corresponding to S-D-lactoylglutathione formation and thus to MG formation, was measured at 30° C. on a spectrophotometer. The standard assay mixture consisted of 1.5 mM DHAP, 1.5 mM glutathione, 50 mM Imidazole (pH 7.0), 2 units of yeast glyoxalase I and 30 µl of MGS sample in a total volume of 1000 µl. Control assay, lacking the MGS sample was run in parallel and the value measured for the control was subtracted to the assay to take into account non-specific formation of MG or S-D-lactoylglutathione. Initial velocities were measured by following the increase in absorbance att 240 nm over time after addition of MGS sample. A unit MGS activity was defined as the formation of 1 µmol of MG/min under the conditions of the assay. Specific enzyme activity was expressed as units per mg of protein.

4. Purification of the MGS Enzymes

The four proteins MgsA, MgsA*(V116L), MgsA*(H21Q), MgsA*(A95V) were purified using the same protocol. This protocol was adapted from Hooper and Cooper (1972).

All chromatographic columns were run at room temperature. Fractions were stored at 4° C. between purification steps.

4.1. Step 1: Preparation of Cell-Free Extracts

Between 350-400 mg of *E. coli* biomass was resuspended in 70 ml of 50 mM Imidazole, 1 mM Potassium Phosphate pH 7, and a protease inhibitor cocktail. Cells were sonicated on ice (Branson sonifier, 70 W) in a Rosett cell RZ3 during six cycles of 30 sec with 30 sec intervals. Cells debris were removed by centrifugation at 12000 g for 30 min at 4° C. Supernatant was kept as the crude extract.

4.2. Step 2: Ammonium Sulphate Precipitation

Solid ammonium sulphate (209 g/l) was added to the crude extract on ice. After 15 min of incubation at 4° C., the precipitate was removed by centrifugation at 12000 g for 15 min at 4° C. and discarded. More ammonium sulphate (111 g/l) was added to the supernatant solution at 0° C. After 15 min of incubation at 4° C., the mix was centrifuged at 12000 g for 15 min at 4° C. The supernatant was discarded and the precipitate dissolved in 200 ml of 50 mM Imidazole, 1 mM Potassium Phosphate pH 7.

4.3. Step 3: Anionic Chromatography pH 7

Using an Akta Purifier (GE Healthcare), the half of ammonium sulphate pellet resuspended in 50 mM Imidazole, 1 mM Potassium Phosphate pH 7 (100 ml) was loaded onto a 6 ml Resource Q column (GE Healthcare) equilibrated with the same buffer. Two runs were realised. For each run, the column was washed with 10 column volumes of the same buffer. Proteins were eluted with a gradient of 20 column volumes from 0 M to 0.5 M sodium chloride. After elution, the column was washed with 1 column volume of a gradient form 0.5M to 1M sodium chloride and with 5 column volumes of 1M sodium chloride. The flow rate of the column was 2 ml/min and 5 ml fractions were collected.

The MGS protein was eluted with 150 mM sodium chloride. The fractions which contain the MGS protein were pooled and dialysed against 50 mM Imidazole, 1 mM Potassium Phosphate, 100 mM NaCl pH 8 overnight.

4.4. Step 4: Anionic Chromatography pH 8

The dialysed pool was applied to a 1.7 ml Mono Q column (GE Healthcare) equilibrated with 50 mM Imidazole, 1 mM Potassium Phosphate, 100 mM NaCl pH 8. To avoid column overload, 4 runs were done. For each run, the column was washed with 10 column volumes of 50 mM Imidazole, 1 mM Potassium Phosphate, 100 mM NaCl pH 8. Proteins were eluted with a gradient of 20 column volumes from 0.1 M to 0.5 M sodium chloride. After elution, the column was washed with 1 column volume of a gradient form 0.5M to 1M sodium chloride and with 5 column volumes of 1M sodium chloride. The flow rate of the column was 1.5 ml/min and 2 ml fractions were collected.

The MGS protein was eluted with about 200 mM sodium chloride. The fractions which contain the MGS protein were pooled and concentrated to be loaded on a gel filtration column.

4.5. Step 5: Gel Filtration

The concentrated fractions from the Mono Q column were loaded onto a Superdex 200 10/300 GL column (GE Healthcare) equilibrated with 50 mM Imidazole, 1 mM Potassium Phosphate, 350 mM NaCl pH 7. Four runs were realised. The flow rate of the column was 0.5 ml/min and 0.5 ml fractions were collected. The MGS protein was eluted with about 13.5 ml of buffer. The expression and purification of the mutant MGS were remarkably similar to that of the wild type enzyme. There were no differences in the oligomerisation state between the native mgsA and the mutated mgsA*.

All proteins were stored at 4° C. in presence of 0.1 mg/ml BSA to stabilise the protein.

The pool of each purification step was analysed on a SDS 4-15% gradient polyacrylamide gel (FIG. 3). This gel shows the purity increased along the purification step. After the superdex 200 column, the protein was almost 90% pure. The final pool showed two major bands at about 17 kDa corresponding to the protein MgsA and at about 70 kDa corresponding to the BSA used to stabilize the enzyme.

5. Characterization of the MGS Enzymes in the Absence of Orthophosphate

Kinetic constants (Km, kcat and kcat/Km) for the four purified enzymes (MgsA, MgsA*(V116L), MgsA*(H21Q) and MgsA*(A95V)) were determined using the activity assay previously described. At least six DHAP concentrations between 0.08 mM and 1.5 mM were analysed for each enzyme. For all kinetics, initial velocity was determined in triplicate for all DHAP concentrations.

Before the activity assay, the purified protein stored at 4° C. in 50 mM Imidazole, 1 mM Potassium Phosphate, 350 mM NaCl, 0.1 mg/ml BSA pH 7 was diluted in 50 mM Imidazole, 10% glycerol, 0.1 mg/ml BSA pH 7.

Kinetic constants of each protein were calculated with the module enzyme kinetics from the software Sigma Plot (Systat Software Inc, San Jose Calif.). The data sets exhibiting Michaelis-Menten were fitted to a Michaelis-Menten equation. The different kinetic parameters of four MGS were compiled in the Table.

TABLE 7 kinetics parameters for the MGS enzymes without Pi

|  | MgsA | MgsA* H21Q | MgsA* V116L | MgsA* A95V |
|---|---|---|---|---|
| Km (mM) | 0.19 ± 0.017 | 0.1746 ± 0.009 | 0.1606 ± 0.021 | 0.28 ± 0.027 |
| Specific activity (μmoles/min/mg) | 1049 ± 24 | 1056 ± 15 | 505 ± 16 | 786 ± 24 |
| kcat (s − 1) | 296 ± 7 | 298 ± 4 | 143 ± 4 | 222 ± 7 |
| kcat/km (M − 1s − 1) | 1.54E+06 ± 1.72E+05 | 1.70E+06 ± 1.12E+05 | 8.87E+05 ± 1.44E+05 | 7.84E+05 ± 9.73E+04 |

The kinetics parameters of the four enzymes, the native MGS and the 3 mutant MGS in absence of orthophosphate were very similar. The value for Km is in good agreement with the value of 0.20±0.03 mM previously reported for the native enzyme (Saadat and Harrison, 1998).

Kinetic constants of each protein at each concentration of potassium phosphate (0.2 mM, 0.3 mM, 1 mM Pi) were determined with the module enzyme kinetics from the software Sigma Plot. The different kinetic parameters of MGS enzymes were compiled in the Table 8.

TABLE 8 kinetic parameters for the MGS enzymes in the presence of various concentrations of Pi

|  | Without Pi | 0.2 mM Pi | 0.3 mM Pi | 1 mM Pi |
|---|---|---|---|---|
| MgsA | | | | |
| Km (mM) | 0.19 ± 0.017 | 0.41 ± 0.013 | 0.57 ± 0.021 | >1.53 |
| Specific activity (μmol/min/mg) | 1049 ± 24 | 1019 ± 24 | 1104 ± 42 | >592 |
| kcat (s − 1) | 296 ± 7 | 287 ± 7 | 311 ± 12 | >167 |
| Kcat/Km (M − 1s − 1) | 1.5E+06 ± 1.7E+05 | 7E+05 ± 3.8E+04 | 5.4E+05 ± 4.1E+04 | >1.09E+05 |
| MgsA* A95V | | | | |
| Km (mM) | 0.28 ± 0.027 | 0.34 ± 0.077 | 0.45 ± 0.079 | 0.51 ± 0.085 |
| Specific activity (μmol/min/mg) | 786 ± 24 | 799 ± 38 | 901 ± 61 | 787 ± 52 |
| kcat (s − 1) | 222 ± 7 | 226 ± 11 | 254 ± 17 | 222 ± 15 |
| Kcat/Km (M − 1s − 1) | 7.8E+05 ± 9.7E+04 | 6.6E+05 ± 1.8E+05 | 5.7E+05 ± 1.4E+05 | 4.31E+05 ± 1.00E+05 |
| MgsA* H21Q | | | | |
| Km (mM) | 0.17 ± 0.009 | 0.22 ± 0.024 | 0.24 ± 0.016 | 0.38 ± 0.035 |
| Specific activity (μmol/min/mg) | 1056 ± 15 | 1048 ± 34 | 1057 ± 21 | 1056 ± 35 |
| kcat (s − 1) | 298 ± 4 | 295 ± 10 | 298 ± 6 | 298 ± 10 |
| Kcat/Km (M − 1s − 1) | 1.7E+06 ± 1.1E+05 | 1.3E+06 ± 1.8E+05 | 1.2E+06 ± 1.0E+05 | 7.9E+05 ± 1.0E+05 |
| MgsA* V116L | | | | |
| Km (mM) | 0.16 ± 0.021 | 0.19 ± 0.026 | 0.17 ± 0.029 | 0.47 ± 0.068 |
| Specific activity (μmol/min/mg) | 505 ± 16 | 525 ± 20 | 502 ± 23 | 598 ± 33 |
| kcat (s − 1) | 143 ± 4 | 148 ± 6 | 142 ± 7 | 169 ± 9 |
| Kcat/Km (M − 1s − 1) | 8.9E+05 ± 1.4E+05 | 7.9E+05 ± 1.4E+05 | 8.1E+05 ± 1.8E+05 | 3.6E+05 ± 7.2E+04 |

Specific activity for each MGS is directly calculated from the kcat value. Specific activity of MgsA and MgsA*(H21Q) were similar. Specific activity of MgsA*(A95V) represented 75% of the specific activity of MgsA. Specific activity of MgsA*(V116L) represented 50% of the specific activity of MgsA. The mutations were not detrimental for the activity of the enzyme.

6. Characterization of the MGS Enzymes in the Presence of Orthophosphate

The kinetic parameters (Km, kcat and kcat/Km) of the four purified enzymes (MgsA, MgsA*(V116L), MgsA*(H21Q) and MgsA*(A95V)) stored at 4° C. in 50 mM Imidazole, 1 mM Potassium Phosphate, 350 mM NaCl, 0.1 mg/ml BSA pH 7 were determined in presence of different concentration of potassium phosphate in the activity assay (0.2 mM, 0.3 mM, 1 mM orthophosphate (Pi)). Before the activity assay, the protein is diluted in 50 mM Imidazole, 10% glycerol, 0.1 mg/ml BSA pH 7. To determine precisely these kinetic parameters, all measures of initial velocities were done in triplicate for at least six concentrations in substrate (DHAP) between 0.08 mM and 1.5 mM.

For the native MgsA, when activity was measured at various concentration of DHAP without phosphate, the enzyme showed standard Michaelis-Menten kinetics. However, the presence of Pi at concentrations of 0.2-0.3 mM caused the response to DHAP to become sigmoidal, and raising the Pi concentration led to an increasingly pronounced sigmoidal response. As a consequence, the Km of the enzyme was sharply increased. This denoted the allosteric inhibition of the MGS enzyme by orthophosphate, as already described in the literature (Saadat and Harrison, 1998).

For the three mutants MgsA*(V116L), MgsA*(H21Q) and MgsA*(A95V), at all concentrations of Pi, the kinetics fitted to a Michaelis-Menten equation and no allosteric inhibition by Pi was found. The Michaelis Menten curves were very similar in absence and in presence of orthophosphate.

To summarize, the properties of the 3 mutant MGS were very similar: the mutant MGS have lost the allosteric inhibition by orthophosphate shown by the native MGS enzyme.

Example 3

Construction of Two E. coli 1,2-Propanediol Producer Strains Expressing Wildtype or Modified MGS and Assessment of 1,2-Propanediol Production 1. Construction of the Modified Strain E. coli MG1655, mgsA*(H21Q)::Km, Δedd-eda, ΔgloA, ΔaldA, ΔaldB, ΔarcA, Δndh (pME101-VB01-yqhD*(G149E)-gldA* (160T).

1.1. Construction of a Modified Strain E. coli ΔgloA::Cm

The gene gloA was inactivated in strain E. coli MG1655 by inserting a chloramphenicol antibiotic cassette and deleting most of the gene concerned using the technique described in protocol 1 with the oligonucleotides given in Table 5. The deletion was checked by a PCR analysis with the appropriate oligonucleotides given in Table 6. The resulting strain was named E. coli MG1655 ΔgloA::Cm.

1.2. Construction of a Modified Strain E. coli ΔgloA::Cm Δedd-eda::Km 1.2.1. Construction of a Modified Strain E. coli Δedd-eda::Km The genes edd-eda were inactivated in strain E. coli MG1655 by inserting a kanamycin antibiotic cassette and deleting most of the gene concerned using the technique described in Protocol 1 with the oligonucleotides given in Table 5. The deletion was checked by a PCR analysis with the appropriate oligonucleotides given in Table 6. The resulting strain was named E. coli MG1655 Δedd-eda::Km.

1.2.2. Construction of a Modified Strain E. coli ΔgloA:: Cm, Δedd-eda::Km.

The deletion of the genes edd-eda by replacement of the genes by a kanamycin resistance cassette in the strain E. coli ΔgloA::Cm was performed by the technique of transduction with phage P1 according to Protocol 2.

Protocol 2: Transduction with Phage P1 for Deletion of a Gene

The deletion of the chosen gene by replacement of the gene by a resistance cassette (kanamycin or chloramphenicol) in the recipient E. coli strain was performed by the technique of transduction with phage P1. The protocol was in two steps, (i) the preparation of the phage lysate on the strain MG1655 with a single gene deleted and (ii) the transduction of the recipient strain by this phage lysate.

Preparation of the Phage Lysate

Seeding with 100 µl of an overnight culture of the strain MG1655 with a single gene deleted of 10 ml of LB+Cm 30 ng/ml+glucose 0.2%+$CaCl_2$ 5 mM.

Incubation for 30 min at 37° C. with shaking.

Addition of 100 µl of phage lysate P1 prepared on the wild type strain MG1655 (approx. 1×10$^9$ phage/ml).

Shaking at 37° C. for 3 hours until all cells were lysed.

Addition of 200 µl of chloroform, and vortexing.

Centrifugation for 10 min at 4500 g to eliminate cell debris.

Transfer of supernatant in a sterile tube and addition of 200 µl of chloroform.

Storage of the lysate at 4° C.

Transduction

Centrifugation for 10 min at 1500 g of 5 ml of an overnight culture of the E. coli recipient strain in LB medium.

Suspension of the cell pellet in 2.5 ml of $MgSO_4$ 10 mM, $CaCl_2$ 5 mM.

Control tubes: 100 µl cells
100 µl phages P1 of the strain MG1655 with a single gene deleted.

Tube test: 100 µl of cells+100 µl phages P1 of strain MG1655 with a single gene deleted.

Incubation for 30 min at 30° C. without shaking.

Addition of 100 µl sodium citrate 1 M in each tube, and vortexing.

Addition of 1 ml of LB.

Incubation for 1 hour at 37° C. with shaking

Plating on dishes LB+Cm 30 µg/ml after centrifugation of tubes for 3 min at 7000 rpm.

Incubation at 37° C. overnight.

The antibiotic-resistant transformants were then selected and the insertion of the deletion was checked by a PCR analysis with the appropriate oligonucleotides given in Table 6.

The deletion was checked by a PCR analysis with the appropriate oligonucleotides given in Table 6 as well as the other deletions already present in the strain.

The resulting strain was named E. coli ΔgloA::Cm, Δedd-eda::Km.

1.3. Construction of a Modified Strain E. coli MG1655 ΔgloA, Δedd-eda

The antibiotic resistance cassettes were eliminated in the strain E. coli ΔgloA::Cm Δedd-eda::Km, according to Protocol 3.

Protocol 3:

Elimination of Resistance Cassettes (FRT System)

The chloramphenicol and/or kanamycin resistance cassettes were eliminated according to the following technique. The plasmid pCP20 carrying the FLP recombinase acting at the FRT sites of the chloramphenicol and/or kanamycin resistance cassettes was introduced into the strain by electroporation. After serial culture at 42° C., the loss of the antibiotic resistance cassettes was checked by PCR analysis with the oligonucleotides given in Table 5.

The presence of the modifications previously built in the strain was checked using the oligonucleotides given in Table 6.

The strain obtained was named E. coli MG1655 ΔgloA Δedd-eda.

1.4. Construction of the Modified Strain E. coli MG1655 Δedd-eda ΔgloA, ΔaldA::Cm 1.4.1. Construction of the Modified Strain E. coli MG1655 ΔaldA::Cm The gene aldA was inactivated in strain E. coli MG1655 by inserting a chloramphenicol antibiotic cassette and deleting most of the gene concerned using the technique described in protocol 1 with the oligonucleotides given in Table 5. The deletion was checked by a PCR analysis with the appropriate oligonucleotides given in Table 6. The resulting strain was named E. coli MG1655 ΔaldA::Cm.

1.4.2. Construction of the Modified Strain E. coli MG1655 Δedd-eda ΔgloA, ΔaldA::Cm The deletion of the gene aldA by replacement of the gene by a chloramphenicol resistance cassette in the strain E. coli MG1655 Δedd-eda ΔgloA was performed by the technique of transduction with phage P1 (Protocol 2).

The deletion ΔaldA::Cm and the others modifications were checked using the oligonucleotides described in Table 6.

The resulting strain was named E. coli MG1655 Δedd-eda ΔgloA, ΔaldA::Cm.

1.5. Construction of the Modified Strain E. coli MG1655 Δedd-eda, ΔgloA, ΔaldA::Cm, ΔaldB::Km 1.5.1. Construction of the Modified Strain E. coli MG1655 ΔaldB::Km The gene aldB was inactivated in strain E. coli MG1655 by inserting a Kanamycin antibiotic cassette and deleting most of the gene concerned using the technique described in protocol 1 with the oligonucleotides given in Table 5. The deletion was checked by a PCR analysis with the appropriate oligonucleotides given in Table 6. The resulting strain was named E. coli MG1655 ΔaldB::Km.

1.5.2. Construction of the Modified Strain E. coli MG1655 Δedd-eda ΔgloA, ΔaldA::Cm, ΔaldB::Km The deletion of the gene aldA by replacement of the gene by a Kanamycin resistance cassette in the strain E. coli MG1655 Δedd-eda ΔgloA ΔaldA::Cm, was performed by the technique of transduction with phage P1 (Protocol 2).
The deletion ΔaldB::Km and the others modifications were checked using the oligonucleotides described in Table 6.
The resulting strain was named E. coli MG1655 Δedd-eda ΔgloA, ΔaldA::Cm, ΔaldB::Km.

1.6. Construction of the Modified Strain E. coli MG1655 Δedd-eda ΔgloA, ΔaldA, ΔaldB The antibiotic resistance cassettes were eliminated in the strain E. coli MG1655 Δedd-eda ΔgloA, ΔaldA::Cm, ΔaldB::Km according to Protocol 3.
The loss of the antibiotic resistance cassettes was checked by PCR analysis with the oligonucleotides given in Table 6. The presence of the modifications previously built in the strain was also checked using the oligonucleotides given in Table 6.
The strain obtained was named E. coli MG1655 Δedd-eda ΔgloA, ΔaldA, ΔaldB.

1.7. Construction of the Modified Strain E. coli MG1655 Δedd-eda ΔgloA, ΔaldA, ΔaldB, ΔarcA::Km 1.7.1. Construction of the Modified Strain E. coli MG1655 ΔarcA::Km The gene arcA was inactivated in strain E. coli MG1655 by inserting a Kanamycin antibiotic cassette and deleting most of the gene concerned using the technique described in Protocol 1 with the oligonucleotides given in Table 5. The deletion was checked by a PCR analysis with the appropriate oligonucleotides given in Table 6.
The resulting strain was named E. coli MG1655 ΔarcA::Km.

1.7.2. Construction of the Modified Strain E. coli MG1655 Δedd-eda ΔgloA, ΔaldA, ΔaldB, ΔarcA::Km The deletion of the gene arcA by replacement of the gene by a Kanamycin resistance cassette in the strain E. coli Δedd-eda ΔgloA, ΔaldA, ΔaldB, ΔarcA::Km, was performed by the technique of transduction with phage P1 (Protocol 2)
The deletion ΔarcA::Km and the others modifications were checked using the oligonucleotides described in Table 6.
The strain obtained was named E. coli MG1655 Δedd-eda ΔgloA, ΔaldA, Δald, ΔarcA::Km.

1.8. Construction of the Modified Strain E. coli MG1655 Δedd-eda ΔgloA, ΔaldA, ΔaldB, ΔarcA::Km, Δndh::Cm 1.8.1. Construction of the Modified Strain E. coli MG1655 Δndh::Cm The gene ndh was inactivated in strain E. coli MG1655 by inserting a chloramphenicol resistance cassette and deleting most of the gene concerned using the technique described in Protocol 1 with the oligonucleotides given in Table 5. The deletion was checked by a PCR analysis with the appropriate oligonucleotides given in Table 6.
The resulting strain was named E. coli MG1655 Δndh::Cm.

1.8.2. Construction of the Modified Strain E. coli MG1655 Δedd-eda ΔgloA, ΔaldA, ΔaldB, ΔarcA::Km, Δndh::Cm The deletion of the gene ndh by replacement of the gene by a chloramphenicol resistance cassette in the strain E. coli Δedd-eda ΔgloA, ΔaldA, ΔaldB, ΔarcA::Km, was performed by the technique of transduction with phage P1 (Protocol 2). The deletion Δndh::Cm and the others modifications were checked using the oligonucleotides described in Table 6.
The strain obtained was named E. coli MG1655 Δedd-eda ΔgloA, ΔaldA, Δald, ΔarcA::Km, Δndh::Cm.

1.9. Construction of the Modified Strain E. coli MG1655 Δedd-eda, ΔgloA, ΔaldA, ΔaldB, ΔarcA, Δndh The antibiotic resistance cassette was eliminated in the strain E. coli MG1655 Δedd-eda ΔgloA, ΔaldA, ΔaldB, ΔarcA::Km, Δndh::Cm according to Protocol 3.
The loss of the antibiotic resistance cassettes was checked by PCR analysis with the oligonucleotides given in Table 6. The presence of the modifications previously built in the strain was also checked using the oligonucleotides given in Table 6.
The strain obtained was named E. coli MG1655 Δedd-eda ΔgloA, ΔaldA, ΔaldB, ΔarcA, Δndh.

1.10. Construction of the Modified Strain E. coli MG1655 ΔgloA, Δedd-eda, ΔaldA, ΔaldB, ΔarcA, Δndh (pME101VB01-yqhD*(G149E)-gldA*(A160T))

1.10.1. Construction of the Plasmid pME101-VB01-yqhD*(G149E)-gldA*(A160T)

1.10.1.1. Construction of the Plasmid pME101-VB01
The plasmid pME101VB01 was derived from plasmid pME101 and harbors a multiple cloning site containing recognition site sequences specific for the rare restriction endonucleases NheI, SnaBI, PacI, BglII, AvrII, SacII and AgeI following by the adc transcription terminator of Clostridium acetobutylicum ATCC824.
For the expression from a low copy vector the plasmid pME101 was constructed as follows. The plasmid pCL1920 (Lerner & Inouye, 1990, NAR 18, 15 p 4631—GenBank AX085428) was PCR amplified using the oligonucleotides PME101F and PME101R and the BstZ17I-XmnI fragment from the vector pTrc99A (Amersham Pharmacia Biotech, Piscataway, N.J.) harboring the lacI gene and the trc promoter was inserted into the amplified vector.

```
PME101F (SEQ ID NO 12):
ccgacagtaagacgggtaagcctg

PME101R (SEQ ID NO 13):
agcttagtaaagccctcgctag
```

A synthetic double-stranded nucleic acid linker comprising the multicloning site and adc transcriptional terminator was used to generate pME101VB01. Two 100 bases oligonucleotides that complement flanked by NcoI or HindIII digested restriction sites were annealed. The 100-base pair product was subcloned into NcoI/HindIII digested plasmid pME101 to generate pME101VB01.

```
pME101VB01 1, consisting of 100 bases (SEQ ID NO 14):
catgggctagctacgtattaattaaagatctcctagggagctcaccggtTAAAAATAAGAGTTACCTTAAAT GGTAACTCTTATTTTTTAggcgcgcca pME101VB01 2, consisting of 100 bases (SEQ ID NO 15):
agcttggcgcgccTAAAAAAATAAGAGTTACCATTTAAGGTAACTCTTATTTTTAaccgg tgagctccctaggagatctttaattaatacgtagctagcc
``` with:
- a region (underlined lower-case letters) corresponding to the multicloning site
- a region (upper-case letters) corresponding to the adc transcription terminator (sequence 179847 to 179814) of *Clostridium acetobutylicum* ATCC 824 pSOL1 (NC_001988).

1.10.1.2. Construction of the Plasmid pME101-VB01-yqhD*(G149E)-gldA*(A160T)

1.10.1.2.1. Construction of the Plasmid pSCB-yqhD*(G149E)

The gene yqhD was PCR amplified from genomic DNA of *E. coli* MG1655 using the following oligonucleotides

```
yqhD F, consisting of 43 pb,
                                         (SEQ ID NO 16)
cgatgcacgtcatgaacaactttaatctgcacaccccaacccg
``` with:
- a region (underlined letter) homologous to the sequence (3153377 to 3153408) of the gene yqhD
- a restriction site BspHI (bold face letters)

```
yqhD R, consisting of 29 pb
                                         (SEQ ID NO 17)
Ctagctagcttagcgggcggcttcgtata
```

With:
- a region (underlined letter) homologous to the sequence (3154540 to 3154521) the gene yqhD
- a restriction site NheI (bold face letters)

The PCR amplified fragment was cloned in pSCB (Strataclone®). The resulting plasmid was named pSCB-yqhD. A directed mutagenesis was performed on this plasmid with the following oligonucleotides: yqhD*G149EmutDirF (consisting of 45 pb, ggttcagaatccaacgcagaagcggt-gatAtcccgtaaaaccacaggc, (SEQ ID NO 18) and yqhD*G149EmutDirR (consisting of 45 pb gcctgtggttttacgg-gaTatcaccgcttctgcgttggattctgaacc, (SEQ ID NO 19). The two oligonucleotides were homologous to the region 3153803 to 3153850. In bold face letter, bases which were changed to create the mutation G149E and capital letter, the base which were changed to create EcoRV restriction site. The resulted plasmid was named pSCB-yqhD*(G149E).

1.10.1.2.2. Construction of the Plasmid pSCB-gldA*(A160T)

The gene gldA, PCR amplified from genomic DNA of *E. coli* MG1655 using the oligonucleotides gldA F and gldA R was cloned in pSCB (Strataclone®). The resulting plasmid was named pSCB-gldA.

A directed mutagenesis was performed on this plasmid with the following oligonucleotides: gldA*A160TmutDirF (consisting of 45 pb, gacaccaaaatcgtcgctggcacacctg-cacgtctgCtagcggcg, SEQ ID NO 20) and gldA*A160TmutDirR (consisting of 45 pb cgccgctaGca-gacgtgcaggtgtgccagcgacgattttggtgtc, SEQ ID NO 21). The two oligonucleotides are homologous to the region 4136602 to 4136558. In bold face letter, bases which were changed to create the mutation A160T and underlined letter, the base which were change to create EcoRV restriction site. The resulted plasmid was named pSCB-gldA*(A160T).

1.10.1.3. Construction of the pME101VB01-yqhD*(G149E)-gldA*(A160T)

The pSCB-yqhD*(G149E) was cut with the restriction enzymes BspHI and NheI and the fragment containing yqhD*(G149E) was cloned into the NcoI/NheI sites of the vector pME101VB01. The resulting plasmid was named pME101VB01-yqhD*(G149E). The pSCB-gldA*(A160T) was cut with the restriction enzymes avrII and SacI and the fragment containing gldA*(A160T) was cloned into the avrII/SacI sites of the vector pME101VB01-yqhD*(G149E). The resulting plasmid was named pME101VB01-yqhD*(G149S)-gldA*(A160T).

1.10.2. Construction of the Modified Strain *E. coli* MG1655 ΔgloA, Δedd-eda, ΔaldA, ΔaldB, ΔarcA, Δndh (pME101VB01-yqhD*(G149E)-gldA*(A160T))

The plasmid pME101VB01-yqhD-gldA*(A160T) was introduced by electroporation into the strain *E. coli* MG1655 ΔgloA, Δedd-eda, ΔaldA, ΔaldB, ΔarcA, Δndh.

The strain obtained was named *E. coli* MG1655 ΔgloA, Δedd-eda, ΔaldA, ΔaldB, ΔarcA, Δndh (pME101VB01-yqhD*(G149E)-gldA*(A160T).

1.11. Construction of the Modified Strain *E. coli* MG1655 mgsA*(H21Q)::Km Δedd-eda, ΔgloA, ΔaldA, ΔaldB, ΔarcA, Δndh (pME101VB01-yqhD*(G149E)-gldA*(A160T))

1.11.1. Construction of the Modified Strain *E. coli* MG1655 mgsA*(H21Q)::Km 1.11.1.1. Construction of the Modified Strain *E. coli* MG1655 mgsA*(H21Q)

A mutation was introduced in the mgsA gene in order to obtain the mutant protein MgsA*(H21Q). The technique used to build this modification was described by Heermann et al. (2008), Microbial Cell Factories. 7(14): 1-8.

The following oligonucleotides were used to amplify the rpsL-Neo cassette:

```
1.mgsA*(H21Q) ::rpsL-Neo F, consisting in 105 pb,
                                         (SEQ ID NO 22)
gttaactacggatgtacattatggaactgacgactcgcactttacctgcgcggaaacatattgcgctggtggcacacgatcaggcct
ggtgatgatggcgggatc
``` with,
- a region (underlined letter) homologous to the sequence of the gene mgsA.
- a region (bold face letter) to amplified rpsL-Neo cassette.

2. mgsA*(H21Q) ::rpsL-Neo R (SEQ ID NO 23)

<u>gggaaattaagttaccggtagtgcctgttgcatacagtacgtgttgttccagtaacggttgatgccgttccacccagctcat</u>

<u>cagcatctgtttgcat</u>tcagaagaactcgtcaagaagg with,
- a region (underlined letter) homologous to the sequence of the gene mgsA with two mutation, the first one (in red) to create the mutation H21Q and the second one (in yellow) to create the restriction site AlwN1.
- a region (bold face letter) to amplify rpsL-Neo cassette.

The fragment obtained was introduced into the strain MG1655 rpsL* (built as described in Heermann et al.) according to Protocol 1. The strain obtained was checked by PCR and sequence analysis. The strain obtained is named *E. coli* mgsA*(H21Q)::rpsL-Neo.

The deletion of the cassette rpsL-Neo was performed according to Protocol 1. The fragment transformed was obtained by the restriction with NcoI and SacI of the plasmid pETTOPO-mgsA*(H21Q).

The modification was checked by PCR using oligonucleotides described in Table 6.

The strain obtained was named strain *E. coli* MG1655 mgsA*(H21Q).

1.11.1.2. Construction of the Modified Strain *E. coli* MG1655 mgsA*(H21 Q)::Km

A kanamycin resistance cassette was introduced in 3' of mgsA*(H21Q) open reading frame (ORF) using the following primers:

mgsA ::Km F consisting of 100 bp:

(SEQ ID NO 24)

<u>tccagtcgccgcatttcaacgacgcggtcgatattctgatccccgattatcagcgttatctcgcggaccgtctgaagtaa</u>tgtaggct ggagctgcttcg with:
- a region (underlined letters) homologous to the end of mgsA*(H21Q) ORF,
- a region (Bold letter) to amplified Kanamycin cassette.

mgsA ::Km R consisting of 100 bp:

(SEQ ID NO 25)

<u>Tgtggaaatactgaaaaatctggatgtgccggtggcgagaaaaccgtaagaaacaggtggcgtttgccacctgtgcaata</u>catat gaatatcctccttag

- a region (underlined letters) homologous to the end of helD ORF,
- a region (Bold letter) to amplified Kanamycin cassette.

The fragment obtained was introduced into the strain MG1655 mgsA*(H21Q) according to Protocol 1. The strain obtained was checked by PCR. The strain obtained was named *E. coli* mgsA*(H21Q)::Km 1.11.2. Construction of the Modified Strain *E. coli* MG1655 mgsA*(H21Q)::Km ΔgloA, Δedd-eda, ΔaldA, ΔaldB, ΔarcA, Δndh (pME101VB01-yqhD*(G149E)-gldA*(A160T))

The replacement of the mgsA with the mgsA*(H21Q)::Km into the strain *E. coli* ΔgloA, Δedd-eda ΔaldA, ΔaldB, ΔarcA, Δndh (pME101VB01-yqhD*(G149E)-gldA*(A160T)) was performed by the technique of transduction with phage P1.

IPTG was added to the culture to promote the expression of the genes borne on the plasmid.

The modifications mgsA*(H21Q)::Km and the others deletion were checked using the oligonucleotides described in Table 6.

2. Construction of the Modified Strain *E. coli* MG1655 mgsA::Km, Δedd-eda, ΔgloA, ΔaldA, ΔaldB, ΔarcA, Δndh (pME101-VB01-yqhD*(G149E)-gldA*(160T).

2.1. Construction of the Modified Strain *E. coli* MG1655 ΔgloA, Δedd-eda, ΔaldA, ΔaldB, ΔarcA, Δndh (pME101VB01-yqhD*(G149E)-gldA*(A160T))

The construction of this strain is described above.

2.2. Construction of the Modified Strain *E. coli* MG1655 mgsA::Km Δedd-eda, ΔgloA, ΔaldA, ΔaldB, ΔarcA, Δndh (pME101VB01-yqhD*(G149E)-gldA*(A160T))

2.2.1. Construction of the Modified Strain *E. coli* MG1655 mgsA::Km

A kanamycin resistance cassette was introduced in 3' of mgsA open reading frame using the following primers: as shown in SEQ ID NO 24 and SEQ ID NO 25.

The fragment obtained was introduced into the strain MG1655 according to Protocol 1. The strain obtained was checked by PCR. The strain obtained was named *E. coli* mgsA::Km 2.2.2 Construction of the Modified Strain *E. coli* MG1655 mgsA::Km, ΔgloA, Δedd-eda, ΔaldA, ΔaldB, ΔarcA, Δndh (pME101VB01-yqhD*(G149E)-gldA*(A160T))

The replacement of the mgsA with the mgsA::Km into the strain *E. coli* Δedd-eda ΔgloA, ΔaldA, ΔaldB, ΔarcA, Δndh (pME101VB01-yqhD*(G149E)-gldA*(A160T)) was performed by the technique of transduction with phage P1. The modifications mgsA::Km and the others deletion were checked using the oligonucleotides described in Table 6. The resulting strain was named *E. coli* MG1655 mgsA::Km, ΔgloA, Δedd-eda, ΔaldA, ΔaldB, ΔarcA, Δndh (pME101VB01-yqhD*(G149E)-gldA*(A160T)).

3. Assessment of 1,2-Propanediol Production in Two *E. coli* Isogenic Strains Differing Only in the mgsA Alleles The two strains described above were cultivated in an Erlenmeyer flask assay (500 ml flasks with 50 ml of medium) under aerobic conditions in minimal medium MML11PG1_100 (see composition in Table 9) with 20 g/l glucose as sole carbon source. Spectinomycin was added at a concentration of 50 mg/l.

TABLE 9 composition of minimal medium MML11PG1_100.

| Constituent | Concentration (g/l) |
|---|---|
| EDTA | 0.0084 |
| $CoCl_2\ 6H_2O$ | 0.0025 |
| $MnCl_2\ 4H_2O$ | 0.0150 |
| $CuCl_2\ 2H_2O$ | 0.0015 |
| $H_3BO_3$ | 0.0030 |
| $Na_2MoO_4\ 2H_2O$ | 0.0025 |
| $Zn(CH_3COO)_2\ 2H_2O$ | 0.0130 |
| Fe(III) citrate $H_2O$ | 0.1064 |
| Citric acid | 1.70 |
| $KH_2PO_4$ | 1.65 |
| $K_2HPO_4\ 3H_2O$ | 0.92 |
| $(NH_4)_2HPO_4$ | 0.40 |
| $(NH_4)_2SO_4$ | 4.88 |
| $MgSO_4\ 7H_2O$ | 1.00 |
| $CaCl_2\ 2H_2O$ | 0.08 |
| Thiamine | 0.01 |
| Glucose or Sucrose | 20.00 |
| MOPS buffer | 40.00 |

The pH of the medium was adjusted to 6.8 with sodium hydroxide

The culture was carried out at 37° C. and the pH was maintained by buffering the culture medium with MOPS.

At the end of the culture, 1,2-propanediol and residual glucose in the fermentation broth were analysed by HPLC using a Biorad HPX 97H column for the separation and a refractometer for the detection. The yields of 1,2-propanediol over glucose were then calculated.

TABLE 10 production of 1,2-propanediol in minimal medium with glucose as carbon source.

| Strain/ | Carbon source | 1,2-propanediol titer (g/l) | 1,2-propanediol yield (g/g carbon source) |
|---|---|---|---|
| E. coli MG1655 mgsA::Km ΔgloA Δedd-eda ΔaldA ΔaldB ΔarcA Δndh (pME101VB01-yqhD*(G149E)-gldA*(A160T)) | glucose | ND (n = 3) | — (n = 3) |
| E. coli MG1655 mgsA*(H21Q)::Km ΔgloA Δedd-eda ΔaldA ΔaldB ΔarcA Δndh (pME101VB01-yqhD*(G149E)-gldA *(A160T)) | glucose | 0.904 +/− 0.049 (n = 3) | 0.133 +/− 0.009 (n = 3) |

ND means 'not detected'
n is the number of repetitions of the same experiment
The figures given are the mean and standard deviation of the figures obtained for n repetitions.
The strain with wild-type MGS does not produce any 1,2-propanediol due to the inhibition by inorganic phosphate.
The E. coli strain with a mutant MGS clearly produces 1,2-propanediol, confirming together with the above findings that strains with mutant MGS that are insensitive to inhibition by inorganic phosphate can produce 1,2-propanediol in the presence of inorganic phosphate.

Example 4

Production of 1,2-Propanediol by E. coli with a Mutant MGS, a Mutant YqhD and a Mutant GlyDH on Glucose and Sucrose 1. Construction of the Modified Strain E. coli MG1655 mgsA*(H21Q)::Km ΔgloA, Δedd-eda, ΔaldA, ΔaldB, ΔarcA, Δndh (pME101-VB01-yqhD*(G149E)-gldA* (A160T)))

The construction of this strain was described previously.

2. Construction of the Modified Strain E. coli MG1655 mgsA*(H21Q) ΔgloA, Δedd-eda, ΔaldA, ΔaldB, ΔarcA, Δndh (pME101-VB01-yqhD*(G149E)-gldA*(A160T)) (pBBR1MCS5-cscBKAR)

2.1. Construction of the Plasmid pBBR1MCS5-cscBKAR

The plasmid pKJL101.1 (Jahreis et al. (2002), J. Bacteriol. 184:5307-5316) was digested by EcoRI. The fragment containing the cscBKAR gene was cloned in pBBR1MCS5 (Kovach et al. (1995), Gene, 166 175-176) also digested by EcoRI.

The resulted plasmid was named pBBR1MCS5-cscBKAR.

2.2. Construction of the Modified Strain E. coli MG1655 mgsA*(H21Q)::Km, ΔgloA, Δedd-eda, ΔaldA, ΔaldB, ΔarcA, Δndh (pME101-VB01-yqhD*(G149E)-gldA* (A160T)) (pBBR1MCS5-cscBKAR)

The plasmids pME101-VB01-yqhD*(G149E)-gldA* (A160T) and pBBR1MCS5-cscBKAR were introduced by electroporation in the strain E. coli MG1655 mgsA*(H21Q), Δedd-eda, ΔgloA, ΔaldA, ΔaldB, ΔarcA, Δndh.

The strain obtained was named strain E. coli MG1655 mgsA* (H21Q)::Km, ΔgloA, Δedd-eda, ΔaldA, ΔaldB, ΔarcA, Δndh (pME101-VB01-yqhD*(G149E)-gldA*(A160T)) (pBBR1MCS5-cscBKAR).

3. Assessment of 1,2-Propanediol Production in Two E. coli with a Mutant MGS, a Mutant YqhD and a Mutant GlyDH on Glucose and Sucrose The two strains described above were cultivated in an Erlenmeyer flask assay (500 ml flasks with 50 ml of medium) under aerobic conditions in minimal medium MML11PG1_100 (see composition in Table 9) with 20 g/l glucose or sucrose as sole carbon source. Spectinomycin was added at a concentration of 50 mg/l.

The culture was carried out at 37° C. and the pH was maintained by buffering the culture medium with MOPS.

At the end of the culture, 1,2-propanediol and residual glucose or sucrose in the fermentation broth were analysed by HPLC using a Biorad HPX 97H column for the separation and a refractometer for the detection. The yields of 1,2-propanediol over glucose or sucrose were then calculated.

TABLE 11 production of 1,2-propanediol in minimal medium with glucose or sucrose as carbon source.

| Strain | Carbon source | 1,2-propanediol titer (g/l) | 1,2-propanediol yield (g/g carbon source) |
|---|---|---|---|
| E. coli MG1655 mgsA*(H21Q)::Km ΔgloA Δedd-eda ΔaldA ΔaldB ΔarcA Δndh (pME101VB01-yqhD*(G149E)-gldA*(A160T)) | glucose | 0.904 +/− 0.049 (n = 3) | 0.133 +/− 0.009 (n = 3) |
| E. coli MG1655 mgsA*(H21Q)::Km ΔgloA Δedd-eda ΔaldA ΔaldB ΔarcA Δndh (pME101VB01-yqhD*(G149E)-gldA*(A160T)) (pBBR1MCS5-cscBKAR) | sucrose | 1.823 +/− 0.098 (n = 3) | 0.196 +/− 0.007 (n = 3) | n is the number of repetitions of the same experiment
The figures given are the mean and standard deviation of the figures obtained for n repetitions.
The production of 1,2-propanediol in a E. coli strain with a mutant MGS was improved on sucrose as sole carbon source as compared with glucose.

Example 5

Construction of Two E. coli Acetol Producer Strains Expressing Wildtype or Modified MGS and Assessment of Acetol Production 1. Construction of the Modified Strain E. coli MG1655 mgsA*(H21Q)::Km Ptrc01-gapA::cm, Δedd-eda, ΔgloA, ΔaldA, ΔaldB, ΔgldA, (pME101-VB01-yqhD)

1.1. Construction of the Modified Strain E. coli MG1655 ΔgloA, Δedd-eda ΔaldA, ΔaldB, ΔgldA 1.1.1. Construction of the Modified Strain ΔgldA::Km The gene gldA was inactivated in strain E. coli MG1655 by inserting a Kanamycin antibiotic cassette and deleting most of the gene concerned using the technique described in Protocol 1 with the oligonucleotides given in Table 5. The deletion was checked by a PCR analysis with the appropriate oligonucleotides given in Table 5.

The resulting strain was named E. coli MG1655 ΔgldA::Km.

1.1.2. Construction of the Modified Strain E. coli MG1655 Δedd-eda ΔgloA, ΔaldA, ΔaldB, ΔgldA::Km The deletion of the gene gldA by replacement of the gene by a Kanamycine resistance cassette in the strain E. coli MG1655 Δedd-eda ΔgloA, ΔaldA, ΔaldB was performed by the technique of transduction with phage P1 (Protocol 2).
   The deletion was checked by a PCR analysis with the appropriate oligonucleotides given in Table 6 as well as the other deletions already present in the strain.
   The resulting strain was named E. coli MG1655 Δedd-eda ΔgloA, ΔaldA, ΔaldB, ΔgldA::Km 1.1.3. Construction of the Modified Strain E. coli MG1655 Δedd-eda ΔgloA, ΔaldA, ΔaldB, ΔgldA The antibiotic resistance cassette was eliminated in the strain E. coli MG1655 Δedd-eda ΔgloA, ΔaldA, ΔaldB, ΔgldA::Km according to Protocol 3.
   The loss of the antibiotic resistance cassette was checked by PCR analysis with the oligonucleotides given in Table 6. The presence of the modifications previously built in the strain was also checked using the oligonucleotides given in Table 6.
   The strain obtained was named E. coli MG1655 Δedd-eda ΔgloA, ΔaldA, ΔaldB, ΔgldA.

1.2. Construction of the Modified Strain E. coli MG1655 Ptrc01-gapA::cm ΔgloA, Δedd-eda, ΔaldA, ΔaldB, ΔgldA 1.2.1. Construction of the Modified Strain MG1655 Ptrc01-gapA::Cm The replacement of the natural gapA promoter with the synthetic short Ptrc01 promoter (SEQ ID NO 26: gagctgttgactattaatcatccggctcgaataatgtgtgg) into the strain E. coli MG1655 was made by replacing 225 pb of upstream gapA sequence with FRT-CmR-FRT and an engineered promoter using the technique described in Protocol 2 with the oligonucleotides given in Table 5.
   The modification was checked by a PCR analysis with the appropriate oligonucleotides given in Table 6. The resulting strain was named E. coli MG1655 Ptrc01-gapA::Cm.

1.2.2. Construction of the Modified Strain E. coli MG1655 Ptrc01-gapA::cm Δedd-eda ΔgloA, ΔaldA, ΔaldB, ΔgldA The replacement of the natural gapA promoter with the synthetic short Ptrc01 promoter into the strain E. coli MG1655 Δedd-eda ΔgloA, ΔaldA, ΔaldB, ΔgldA was performed by the technique of transduction with phage P1.
   The modification Ptrc01-gapA::cm and the other deletions were checked using the oligonucleotides described in Table 6. The strain obtained was named E. coli MG1655 Ptrc01-gapA::cm Δedd-eda ΔgloA, ΔaldA, ΔaldB, ΔgldA.

1.3. Construction of the Modified Strain E. coli MG1655 Ptrc01-gapA::cm Δedd-eda ΔgloA, ΔaldA, ΔaldB, ΔgldA pME101-VB01-yqhD*(G149E), The plasmid pME101VB01-yqhD*(G149E) was introduced by electroporation into the strain E. coli MG1655 Ptrc01-gapA::cm Δedd-eda ΔgloA, ΔaldA, ΔaldB, ΔgldA.
   The strain obtained was named E. coli MG1655 Ptrc01-gapA::cm, ΔgloA, Δedd-eda, ΔaldA, ΔaldB, ΔgldA (pME101-VB01-yqhD*(G149E)).

1.4. Construction of the Modified Strain E. coli MG1655 mgsA*(H21Q)::Km Ptrc01-gapA::cm Δedd-eda ΔgloA, ΔaldA, ΔaldB, ΔgldA pME101-VB01-yqhD*(G149E)

The replacement of the mgsA with the mgsA*(H21Q)::Km into the strain E. coli Δedd-eda ΔgloA, ΔaldA, ΔgldA (pME101VB01-yqhD*(G149E)) was performed by the technique of transduction with phage P1. IPTG was added to the culture to promote the expression of the gene borne on the plasmid.
   The modification mgsA*(H21Q)::Km and the other deletions were checked using the oligonucleotides described in Table 6.
   The resulting strain was named E. coli MG1655 mgsA*(H21Q)::Km Ptrc01-gapA::cm Δedd-eda ΔgloA, ΔaldA, ΔaldB, ΔgldA pME101-VB01-yqhD*(G149E).

2. Construction of the Modified Strain E. coli MG1655 Ptrc01-gapA::cm, mgsA::Km Δedd-eda, ΔgloA, ΔaldA, ΔaldB, ΔgldA, (pME101-VB01-yqhD*(G149E))

2.1. Construction of the Modified Strain E. coli MG1655 Ptrc01-gapA::cm, mgsA::Km Δedd-eda, ΔgloA, ΔaldA, ΔaldB, ΔgldA(pME101-VB01-yqhD*(G149E))

The mgsA::Km was constructed in the strain E. coli MG1655 Ptrc01-gapA::cm Δedd-eda, ΔgloA, ΔaldA, ΔaldB, ΔgldA (pME101-VB01-yqhD*(G149E)) as previously described.
   The strain obtained was named strain E. coli MG1655 Ptrc01-gapA::cm, mgsA::Km, Δedd-eda, ΔgloA, ΔaldA, ΔaldB, ΔgldA. (pME101-VB01-yqhD*(G149E))

3. Assessment of Acetol Production in Two E. coli Isogenic Strains Differing Only in the mgsA Alleles The two strains described above were cultivated in an Erlenmeyer flask assay (500 ml flasks with 50 ml of medium) under aerobic conditions in minimal medium MML11PG1_100 (see composition in Table 9) with 20 g/l glucose as sole carbon source. Spectinomycin was added at a concentration of 50 mg/l.
   The culture was carried out at 37° C. and the pH was maintained by buffering the culture medium with MOPS.
   At the end of the culture, acetol and residual glucose in the fermentation broth were analysed by HPLC using a Biorad HPX 97H column for the separation and a refractometer for the detection. The yields of acetol over glucose or sucrose were then calculated.

TABLE 12 production of acetol in minimal medium with glucose as carbon source.

| Strain | Carbon source | acetol titer (g/l) | acetol yield (g/g carbon source) |
|---|---|---|---|
| E. coli MG1655 mgsA::Km ΔgloA Δedd-eda ΔaldA ΔaldB ΔgldA (pME101VB01-yqhD*(G149E) | glucose | 0.27 +/− 0.37 (n = 2) | 0.014 +/− 0.020 (n = 2) |
| E. coli MG1655 mgsA*(H21Q)::Km | glucose | 2.23 +/− | 0.272 +/− |

TABLE 12-continued production of acetol in minimal medium with glucose as carbon source.

| Strain | Carbon source | acetol titer (g/l) | acetol yield (g/g carbon source) |
|---|---|---|---|
| ΔgloA Δedd-eda ΔaldA ΔaldB ΔgldA (pME101VB01-yqhD*(G149E)) | | 0.23 (n = 2) | 0.022 (n = 2) | n is the number of cultures of different clones of the same strain
The figures given are the mean and standard deviation of the figures obtained for n cultures.
The production of acetol in the E. coli strain with a mutant MGS was dramatically improved as compared with the isogenic strain with a native MGS.

Example 6

Production of Acetol by *E. coli* with a Mutant MGS and a Mutant YqhD on Glucose and Sucrose 1. Construction of the Modified Strain *E. coli* MG1655 Ptrc01-gapA::cm, mgsA*(H21Q::Km), Δedd-eda ΔgloA, ΔaldA, ΔaldB, ΔgldA, pME101-VB01-yqhD*(G149E), The construction of this strain was described previously.

2. Construction of the Modified Strain *E. coli* MG1655 Ptrc01-gapA::cm, mgsA*(H21Q), Δedd-eda ΔgloA, ΔaldA, ΔaldB, ΔgldA pME101-VB01-yqhD*(G149E) pBBR1MCS5-cscBKAR The plasmid pBBR1MCS5-cscBKA was introduced by electroporation in the strain *E. coli* MG1655 Ptrc01-gapA::cm, mgsA*(H21Q::Km), Δedd-eda ΔgloA, ΔaldA, ΔaldB, ΔgldA pME101-VB01-yqhD*(G149E)

The resulted strain was named *E. coli* MG1655 Ptrc01-gapA::cm, mgsA*(H21Q)::Km, Δedd-eda ΔgloA, ΔaldA, ΔaldB, ΔgldA pME101-VB01-yqhD*(G149E) pBBR1MCS5-cscBKAR.

Example 7

Construction of Two *E. coli* Lactate Producer Strains Expressing Wildtype or Modified MGS and Assessment of Lactate Production 1—Construction of a Modified Strain *E. coli* MG1655 Ptrc01-gapA, Δedd-eda, ΔyqhD, Δdld, ΔlldD (pJB137-PgapA-ppsA) (pME101-VB01-yedU).

1.1. Construction of the Modified Strain *E. coli* MG1655 Ptrc01-gapA, Δedd-eda 1.1.1. Construction of the Strain *E. coli* MG1655 Ptrc01-gapA::cm, Δedd-eda::Km The deletion of the gene edd-eda by replacement of the gene by a kanamycin resistance cassette in the strain *E. coli* MG1655 Ptrc01-gapA::cm (see Example 3) is performed by the technique of transduction with phage P1 (protocol 2).

The deletion is checked by a PCR analysis with the appropriate oligonucleotides given in table 6 as well as the others deletions present in the strain.

The resulting strain is named *E. coli* MG1655 Ptrc01-gapA::cm, Δedd-eda::Km 1.1.2. Construction of the Strain *E. coli* MG1655 Ptrc01-gapA, Δedd-eda The antibiotic resistance cassette is eliminated in the strain *E. coli* MG1655 Δ Ptrc01-gapA::cm, Δedd-eda::Km according to protocol 3.

The loss of the antibiotic resistance cassettes is checked by PCR analysis with the oligonucleotides given in Table 6. The presence of the modifications previously built in the strain is also checked using the oligonucleotides given in Table 6.

The strain obtained is named *E. coli* MG1655 Ptrc01-gapA, Δedd-eda.

1.2. Construction of the *E. coli* MG1655 Ptrc01-gapA, Δedd-eda, ΔyqhD.

1.2.1. Construction of the Modified Strain *E. coli* MG1655 ΔyqhD::Km

The gene yqhD is inactivated by inserting a kanamycin antibiotic resistance cassette and deleting most of the gene concerned using the technique described in Protocol 1 with the oligonucleotides given in Table 5. The deletion is checked by a PCR analysis with the appropriate oligonucleotides given in table 6.

The strain obtained is named *E. coli* MG1655 ΔyqhD::Km.

1.2.2. Construction of the Modified Strain *E. coli* Ptrc01-gapA, Δedd-eda, ΔyqhD The deletion of the gene yqhD by replacement of the gene by a Kanamycin resistance cassette in the strain *E. coli* MG1655 Ptrc01-gapA Δedd-eda is performed using the transduction technique with phage P1 described in Protocol 2. The deletion is checked by a PCR analysis with the appropriate oligonucleotides given in table 6.

The strain obtained is named *E. coli* Ptrc01-gapA, Δedd-eda, ΔyqhD::Km.

1.3. Construction of the Modified Strain *E. coli* Ptrc01-gapA, Δedd-eda, ΔyqhD, Δdld 1.3.1. Construction of the Modified Strain *E. coli* MG1655 Δdld::Cm The gene dld is inactivated by inserting a chloramphenicol antibiotic resistance cassette and deleting most of the gene concerned using the technique described in Protocol 2 with the oligonucleotides given in Table 5. The deletion is checked by a PCR analysis with the appropriate oligonucleotides given in table 6.

The strain obtained is named *E. coli* MG1655 Δdld::Cm.

1.3.2. Construction of the Modified Strain *E. coli* MG1655 Ptrc01-gapA, Δedd-eda, ΔyqhD, Δdld.

The deletion of the gene dld in the strain *E. coli* MG1655 *E. coli* MG1655 Ptrc01-gapA, Δedd-eda, ΔyqhD::Km is performed using the transduction technique with phage P1 described in Protocol 2.

The resulting strain is named *E. coli* MG1655 Ptrc01-gapA, Δedd-eda, ΔyqhD::Km, Δdld::Cm.

The chloramphenicol and kanamycin resistance cassettes are then eliminated according to Protocol 3.

The strain obtained is named *E. coli* MG1655 Ptrc01-gapA, Δedd-eda, ΔyqhD, Δdld.

1.4. Construction of the Modified Strain *E. coli* Ptrc01-gapA, Δedd-eda, ΔyqhD, Δdld, ΔlldD 1.4.1. *E. coli* MG1655 ΔlldD::Cm The gene lldD is inactivated by inserting a chloramphenicol antibiotic resistance cassette and deleting most of the gene concerned using the technique described in Protocol 2 with the oligonucleotides given in Table 5. The deletion is checked by a PCR analysis with the appropriate oligonucleotides given in Table 6.

The strain obtained is named *E. coli* MG1655 ΔlldD::Cm.

1.4.2. *E. coli* MG1655 MG1655 Ptrc01-gapA, Δedd-eda, ΔyqhD, Δdld, ΔlldD

The deletion of the gene lldD in the strain *E. coli* MG1655 Ptrc01-gapA, Δedd-eda, ΔyqhD, Δdld is performed using the transduction technique with phage P1 described in Protocol 3.

The resulting strain is named *E. coli* MG1655 Ptrc01-gapA, Δedd-eda, ΔyqhD, Δdld, ΔlldD::Cm.

The chloramphenicol resistance cassette is then eliminated according to Protocol 3. The strain obtained is named *E. coli* MG1655 Ptrc01-gapA, Δedd-eda, ΔyqhD, Δdld, ΔlldD.

1.5. Construction of the Modified Strain E. coli MG1655 Ptrc01-gapA, Δedd-eda, ΔyqhD, Δdld, ΔlldD (pJB137-PgapA-ppsA) (pME101-VB01-yedU)

The plasmids pJB137-PgapA-ppsA and pME101-VB01-yedU (described in patent application PCT/EP2009/053093) are introduced by electroporation in the strain E. coli MG1655 Ptrc01-gapA, Δedd-eda, ΔyqhD, Δdld, ΔlldD.

The resulted strain is named E. coli MG1655 Ptrc01-gapA, Δedd-eda, ΔyqhD, Δdld, ΔlldD. (pJB137-PgapA-ppsA) (pME101-VB01-yedU).

2.—Construction of a Modified Strain E. coli MG1655 Ptrc01-gapA, mgsA*(H21Q), Δedd-eda, ΔyqhD, Δdld, ΔlldD (pJB137-PgapA-ppsA) (pME101-VB01-yedU)

2.1. Construction of a Modified Strain E. coli MG1655 Ptrc01-gapA, mgsA*(H21Q), Δedd-eda, ΔyqhD, Δdld, ΔlldD The mutation mgsA*(H21Q) is constructed in the strain E. coli MG1655 Ptrc01-gapA, Δedd-eda, ΔyqhD, MN, ΔlldD as previously described in Example 3.

The strain obtained is named strain E. coli MG1655 Ptrc01-gapA, mgsA*(H21Q), Δedd-eda, ΔyqhD, Δdld, ΔlldD.

2.2. Construction of a Modified Strain E. coli MG1655 Ptrc01-gapA, mgsA*(H21Q), Δedd-eda, ΔyqhD, Δdld, ΔlldD (pJB137-PgapA-ppsA) (pME101-VB01-yedU)

The plasmids pJB137-PgapA-ppsA and pME101-VB01-yedU, are introduced by electroporation in the strain E. coli MG1655 Ptrc01-gapA, mgsA*(H21Q), Δedd-eda, ΔyqhD, Δdld, ΔlldD.

The resulted strain is named E. coli MG1655 Ptrc01-gapA, mgsA*(H21Q), Δedd-eda, ΔyqhD, Δdld, ΔlldD (pJB137-PgapA-ppsA) (pME101-VB01-yedU).

Example 8

Construction of Two Saccharomyces cerevisiae 1,2-Propanediol Producer Strains and Assessment of 1,2-Propanediol Production 1—Construction of Two S. cerevisiae Strains CENPK Δgpd2, Δtpi1, gldA*(A160T), yqhD, mgsA*(H21Q) and CENPK Δgpd2, Δtpi1, gldA*(A160T), yqhD*(G149E), mgsA*(H21Q)

1-1. Construction of S. cerevisiae Strain CENPK Δgpd2, gldA*(A160T).

The S. cerevisiae strain used was CEN.PK2-1C (MATa; ura3-52; trp1-289; leu2-3,112; h is 3 Δ1; MAL2-8C; SUC2) from Euroscarf.

The gene GPD2 was inactivated by transforming the strain CEN.PK2-1C with a PCR fragment corresponding to pTDH3-gldA*(A160T)-CYCt-pTEF1-ble-TEF1t cassette, built using the "short flanking homology" (SFH) method described by Guldener et al. (1996).

The pTDH3-gldA*(A160T)-CYCt-pTEF1-ble-TEF1t cassette was constructed using long PCR-based fusion of several fragments as described by Shevchuk et al. (2004).

pTDH3 and CYCt were amplified from the plasmid p406TDH3 (Addgene) using pTDH3/GPD2 F and pTDH3 R primers and CYCt/gldA F and CYCt/Zeo R primers respectively.

gldA*(A160T)- was amplified from pSCB gldA*(A160T)- using primers gldA/TDH3F and gldA/CYCtR.

pTEF1-ble-TEF1t was amplified from the plasmid pUG66 from Euroscarf using Zeo/CYCt F and ZEO/GPD2 R as primers.

All fragments were amplified using primers having overlapping ends as described in Table 13. Each fragment was then purified.

100 ng of each fragment was used in a PCR experiment without primers, using low annealing conditions allowing their simultaneous fusion.

The unpurified product obtained in this step was used as a matrix a in a PCR experiment at high Tm, using pTDH3/GPD2 F and ZEO/GPD2 R primers having an extension of 40 by homologous to the 40 first and 40 last by of the GPD2 locus (Table 13).

This fragments was integrated in the GPD2 locus, replacing the GPD2 open reading frame.

The transformation method used was the lithium acetate method described by Schiestl and Gietz (1989). The strain CENPK, Δgpd2, gldA*(A160T) was selected on YEPD rich medium (1% bacto yeast extract, 2% bactopeptone, 2% glucose) supplemented with 75 ng/ml of phleomycin (Cayla, France). The integration of gldA*(A160T) and the deletion of GPD2 gene were confirmed by PCR on genomic DNA extracted, using GPD2 ver F and GPD2 ver R primers (Table 13).

This resulted in the heterologous expression of gldA*(A160T) and deletion of GPD2. The resulting strain was named CENPK Δgpd2, gldA*(A160T).

TABLE 13

| Primer Name | Sequence | Description |
|---|---|---|
| pTDH3/GPD2 F | ATG CTT GCT GTC AGA AGA TTA ACA AGA TAC ACA TTC CTT AGT TTA TCA TTA TCA ATA CTC G (SEQ ID NO 27) | The underlined 40 nucleotides correspond to the 40 first bp of GPD2 gene 21 nucleotides in bold are homologous to the 21 first bp of pTDH3 |
| pTDH3 R | ATCCTCGAAACTAAGTTCTTGGT (SEQ ID NO 28) | 23 nucleotides homologous to the 23 last bp of pTDH3 |
| gldA/TDH3F | AAA CAC CAG AAC TTA GTT TCG AAC TAG TTT ATT CCC ACT CTT (SEQ ID NO 29) | The underlined 22 nucleotides underlined correspond to the last bp of pTDH3 20 nucleotides in bold are homologous to the 20 first bp of gldA or gldA* (A160T) |

TABLE 13-continued

| Primer Name | Sequence | Description |
|---|---|---|
| gldA/CYCtR | TGA AAT ATA AAT AAC GTT CTT AAT ACT AAC ATA ACT ATA AAC TAG TAT GGA CCG CAT TAT TC (SEQ ID NO 30) | The underlined 42 nucleotides correspond to the 42 first bp of CYCt 20 nucleotides in bold are homologous to the 20 last bp of gldA or gldA* (A160T) |
| CYCt/gldA F | CCT GGA TGT ATT TAC CCG GTG ATT GAA TAA TCC GGT CCA TAC TAG TTT ATA GTT ATG TTA GTA TTA (SEQ ID NO 31) | The underlined 46 nucleotides correspond to the 46 last bp of gldA or gldA 20 nucleotides in bold are homologous to the 20 first bp of CYCt |
| CYCt/Zeo R | GAG GCA AGC TAA ACA GAT CTC TAG ACC TAG GTA CCC GCC GGC AAA TTA AAG CCT TCG AGC (SEQ ID NO 32) | The underlined 40 nucleotides correspond to the 40 first bp of ble gene 20 nucleotides in bold are homologous to the 20 last bp of CYCt |
| Zeo/CYCt F | GCT TGA GAA GGT TTT GGG ACG CTC GAA GGC TTT AAT TTG CTA GGT CTA GAG ATC TGT TTA GC (SEQ ID NO 33) | The underlined 40 nucleotides correspond to the 40 last bp of CYCt 22 nucleotides in bold are homologous to the 22 first bp of TEF1p |
| ZEO/GPD2R | CTA TTC GTC ATC GAT GTC TAG CTC TTC AAT CAT CTC CGG TCC ACT AGT GGA TCT GAT ATC ACC T (SEQ ID NO 34) | The underlined 40 nucleotides correspond to the 40 last bp of GPD2 gene 24 nucleotides in bold are homologous to the 24 last bp of TEF1t |
| GPD2ver F | ATG CTT GCT GTC AGA AGA TT (SEQ ID NO 35) | 20 nucleotides homologous to the 20 first bp of GPD2 gene |
| GPD2 ver R | TAG TAT GGA CCG CAT TAT TC (SEQ ID NO 36) | 20 nucleotides homologous to the 20 last nucleotides of gldA*(A160T) |

1-2. Construction of Two *S. cerevisiae* Strains CENPK Δgpd2, gldA*(A160T), yqhD and CENPK Δgpd2, gldA* (A160T), yqhD*(G149E)

The strain used was CENPK, Δgpd2, gldA*(A160T), previously built. The expression of yqhD or yqhD*(G149E) was realised by transforming the strains with a PCR fragment corresponding to a pTEF1-yqhD-CYCt-pTEF1-nat1-TEF1t cassette or pTEF1-yqhD* (G149E)-CYCt-pTEF1-nat1-TEF1t cassette using the "short flanking homology" (SFH) method.

The pTEF1-yqhD-CYCt-pTEF1-nat1-TEF1t cassette or pTEF1-yqhD*(G149E)-CYCt-pTEF1-nat1-TEF1t cassette were constructed using long PCR-based fusion of several fragments.

pTEF1 and CYCt were amplified from the plasmid p405TEF1 (Addgene) using pTEF1/URA3 F and pTEF R primers and CYCt/yqhD F and CYCt/Nat1R primers respectively.

yqhD and yqhD* were amplified respectively from pSCB-yqhD and pSCB yqhD* (G149E) using primers yqhD/TEF-F and yqhD/CYCtR.

pTEF1-nat1-TEF1t was amplified from the plasmid pAG35 from Euroscarf using Nat1/CYCt F and Nat1/Leu2 as primers.

All fragments were amplified using primers having overlapping ends as described in Table 14. Each fragment was then purified.

100 ng of each fragment was used in a PCR experiment without primers using low annealing conditions allowing their simultaneous fusion.

The unpurified product obtained in this step was used as a matrix in a PCR experiment with at high Tm, using pTEF1/LEU2 F and Nat1/Leu2 primers having an extension of 40 by homologous to the 40 first and 40 last by of the LEU2 locus (Table 14).

These fragments were integrated in the LEU2 locus, replacing the LEU2 open reading frame.

The transformation method used was the lithium acetate method. The strain CENPK, Δgpd2, gldA*(A160T) was transformed either by pTEF1-yqhD-CYCt-pTEF1-nat1-TEF1t cassette or by pTEF1-yqhD*(G149E)-CYCt-pTEF1-nat1-TEF1t to obtained CENPK, Δgpd2, gldA* (A160T), yqhD and CENPK, Δgpd2, gldA* (A160T), yqhD* (G149E). Transformants were selected on YEPD rich medium (1% bacto yeast extract, 2% bactopeptone, 2% glucose) supplemented with 50 ng/ml of nourseothricine (Weber bioagents, Germany). The integration of yqhD or yqhD* (G149E) were confirmed by PCR on genomic DNA extracted, using YQHD ver F and YQHD ver R primers (Table 14).

This resulted in the heterologous expression of yqhD and yqhD* (G149E). The resulting strains were named CENPK Δgpd2, gldA*(A160T), yqhD and CENPK Δgpd2, gldA* (A160T), yqhD*(G149E).

TABLE 14

| Primer Name | Sequence | Description |
| --- | --- | --- |
| pTEF1/URA3 F | ATG TCT GCC CCT AAG AAG ATC GTC GTT TTG CCA GGT GAC CAG CTG GAG CTC ATA GCT TCA (SEQ ID NO 37) | The underlined 40 nucleotides correspond to the 40 first bp of LEU2 gene 20 nucleotides in bold are homologous to the 20 first bp pTEF1 |
| pTEF R | TGC GGG TTG GGG TGT GCA GAT TAA AGT TGT TCA TAC TAG TGG ATC CAC TAG TTC TAG AAA (SEQ ID NO 38) | The underlined 40 nucleotides correspond to the 40 first bp of yqhD or yqhD*(G419E) 20 nucleotides bold are homologous to the 20 last bp of pTEF1 |
| yqhD/TEF-F | CAT AGC AAT CTA ATC TAA GTT TTC TAG AAC TAG TGG ATC CAC TAG TAT GAA CAA CTT TAA (SEQ ID NO 39) | The underlined 40 nucleotides correspond to the 40 last bp of pTEF1 20 nucleotides in bold are homologous to the 20 first bp of yqhD or yqhD*(G419E) |
| yqhD/CYCtR | TGA AAT ATA AAT AAC GTT CTT AAT ACT AAC ATA ACT ATA AAC TAG TTT AGC GGG CGG CTT (SEQ ID NO 40) | The underlined 40 nucleotides correspond to the 40 first bp of CYCt 20 nucleotides in bold are homologous to the 20 last bp of yqhD or yqhD*(G419E) |
| CYCt/yqhD F | TGT CAG CCG CCG TAT ATA CGA AGC CGC CCG CTA AAC TAG TTT ATA GTT ATG TTA GTA TTA (SEQ ID NO 41) | The underlined 40 nucleotides correspond to the 40 last bp of yqhD or yqhD*(G419E) 20 nucleotides in bold are homologous to the 20 first bp of CYCt |
| CYCt/Nat1R | CTCCATGTCGCTGGCCGGGTGACCCGG CGGGGACGAGGCAGCAAATTAAA GCCTTCGAGC (SEQ ID NO 42) | The underlined 40 nucleotides correspondto the 40 first bp of pTEF1 20 nucleotides in bold are homologous to the 20 last bp of CYCt |
| Nat1/CYCt F | GCT TGA GAA GGT TTT GGG ACG CTC GAA GGC TTT AAT TTG CTG CCT CGT CCC CGC CGG GTC (SEQ ID NO 43) | The underlined 40 nucleotides correspond to the 40 last bp of CYCt 20 nucleotides in bold are homologous to the 20 first bp of pTEF1 |
| Nat1/Leu2 | TTA AGC AAG GAT TTT CTT AAC TTC TTC GGC GAC AGC ATC ACA GTA TAG CGA CCA GCA TTC (SEQ ID NO 44) | The underlined 40 nucleotides correspond to the 40 last bp of LEU2 gene 20 nucleotides in bold are homologous to the 20 last bp of TEF1t |
| YQHD ver F | ATG TCT GCC CCT AAG AAG ATC (SEQ ID NO 45) | 20 nucleotides homologous to the 20 first bp of LEU2 gene |
| YQHD ver R | AC TAG TTT AGC GGG CGG CTT (SEQ ID NO 46) | 20 nucleotides homologous to the 20 last bp of yqhD* (G149E) |

1-3. Construction of Two S. cerevisiae Strain CENPK Δgpd2, Δtpi1, gldA*(A160T), yqhD, mgsA*(H21Q) and CENPK Δgpd2, Δtpi1, gldA*(A160T), yqhD*(G149E), mgsA*(H21Q)

The two strains used was CENPK, Δgpd2, gldA*(A160T), yqhD or CENPK, Δgpd2, gldA*(A160T), yqhD*, previously built.

The gene TPI1 was inactivated by transforming the strains with a PCR fragment corresponding to a pTEF1-hph-TEF1t-pPGK 1-msgA*(H21Q) cassette using the "short flanking homology" (SFH) method.

The pTEF1-hph-TEF1t-pPGK1-msgA*(H21Q) cassette was constructed using long PCR-based fusion of several fragments.

The pTEF1-hph-TEF1t-pPGK1 were amplified from the plasmid pAG35pPGK1 constructed from pAG35 (Euroscarf) using PGK1/TPI1F and PGK1/mgsAR mgsA*(H21Q) was amplified from pETTOPO mgsA*(H21Q) using the primers mgsA/PGK1F and mgsA/TPI R as primers.

All fragments were amplified using primers having overlapping ends as described in Table 15. Each fragment was then purified.

100 ng of each fragment was used in a PCR experiment without primers and using low annealing conditions, allowing their simultaneous fusion.

The unpurified product obtained in this step was used as a matrix in a PCR experiment at high Tm, using PGK1/TPI1F and mgsA/TPI R primers having an extension of 40 by homologous to the 40 first and 40 last by of the TPI1 locus (Table 15).

This fragment was integrated in the TPI1 locus, replacing TPI1 open reading frame.

The transformation method used is the lithium acetate method. The strain CENPK, Δgpd2, gldA*(A160T), yqhD and the strain CENPK, Δgpd2, gldA*(A160T), yqhD* (G149E) was transformed by pTEF1-hph-TEF1t-pPGK1-msgA*(H21Q) cassette to obtained CENPK, Δgpd2, Δtpi1, gldA*(A160T), yqhD* (G419E), msgA*(H21Q), CENPK, Δgpd2, Δtpi1, gldA*(A16 Transformants were selected on YEPD rich medium (1% bacto yeast extract, 2% bactopeptone, 2% glucose) supplemented with 250 µg/ml of hygromycin (Sigma-Aldrich).

The integration of msgA*(H21Q) was confirmed by PCR on genomic DNA extracted, using mgsA ver F and mgsA ver R primers (Table 15).

This resulted in the heterologous expression of mgsA* (H21Q) and deletion of TPI1. The resulting strains were named CENPK Δgpd2, Δtpi1, gldA*(A160T), yqhD, mgsA* (H21Q) and CENPK Δgpd2, Δtpi1, gldA*(A160T), yqhD* (G149E), msgA*(H21Q).

2—Assessment of 1,2-Propanediol Production in *S. cerevisiae* CENPK Δgpd2, Δtpi1, gldA*(A160T), yqhD, mgsA* (H21Q)

The strain CENPK, Δgpd2, Δtpi1, gldA*(A160T), yqhD, msgA*(H21Q) described above and the control strain CEN.PK2-1C were cultivated in batch culture, under anaerobic or aerobic conditions in minimal medium (SD medium 0.67% of Yeast nitrogen base without amino acid (DIFCO)) containing either 5% of glucose or 5% of sucrose as sole carbon source. Minimal medium was supplemented with 50 mg/l of uracil, 250 mg/l of leucine, 50 mg/L of histidine and 50 mg/L of tryptophan. Cultures were grown at 28° C. under agitation at 225 rpm.

Aerobic cultures were carried out in shake flask of 250 ml containing 50 ml of medium. Anaerobic cultures were carried out in penicillin flask of 100 ml containing 90 ml of medium. At the end of the culture, 1,2-propanediol in the fermentation broth were analysed by gas chromatography/mass spectrometry (GC/MS) with an Agilent 7890A Series gas chromotograph coupled to an Agilent 5975C Series mass selective detector (EI) and a HP INNOWax column. The retention time and mass spectrum of 1,2-propanediol generated were compared to those of authentic 1,2-propanediol. Residual glucose or sucrose in the fermentation broth were analysed by HPLC using a Biorad HPX 97H column for the separation and a refractometer for the detection. The yields of 1,2-propanediol over glucose or sucrose were then calculated.

TABLE 15

| Primer Name | Sequence | Description |
|---|---|---|
| PGK1/TPI1F | ATG TCG AAA GCT ACA TAT AAG GAA CGT GCT GCT ACT CAT CGC CAG ATC TGT TTA GCT TGC (SEQ ID NO 47) | The underlined 40 nucleotides correspond to the 40 first bp of TPI1 gene 20 nucleotides in bold are homologous to 20 the first bp pTEF1 |
| PGK1/mgsAR | GTC CGA GTC GTC AGT TCC ATA ATA CGC AAA CCG CCT CTC C (SEQ ID NO 48) | The underlined 21 nucleotides correspond to the 40 first bp of mgsA or msgA*(H21Q) 19 nucleotides in bold are homologous to 20 the last bp of pPGK1 |
| mgsA/PGK1F | GGA GAG GCG GTT TGC GTA TTA TGG AAC TGA CGA CTC GCA C (SEQ ID NO 49) | The underlined 22 nucleotides correspond to the 40 last bp of pPGK1 18 nucleotides in bold are homologous to the 20 first bp of mgsA or msgA*(H21Q) |
| mgsA/TPI R | TTA GTT TTG CTG GCC GCA TCT TCT CAA ATA TGC TTC CCT TTA CTT CAG ACG GTC CGC GAG (SEQ ID NO 50) | The underlined 40 nucleotides correspond to the 40 last bp of TPI1 20 nucleotides in bold are homologous to the 20 last bp of mgsA or msgA*(H21Q) |
| mgsA ver F | GC AAC TGA CGA CTC GCA C (SEQ ID NO 51) | 20 nucleotides homologous to the 20 first bp of TPI1 gene |
| mgsA ver R | TTAGTTTCTAGAGTTGATGA (SEQ ID NO 52) | 20 nucleotides homologous to the 20 last bp of mgsA or msgA*(H21Q) |

TABLE 16 production of 1,2-propanediol in minimal medium in aerobic or anaerobic conditions with glucose or sucrose as carbon source.

| Strain | Conditions | Carbon source | 1,2-propanediol titer (mg/l) | 1,2-propanediol yield (mg/g carbon source) |
|---|---|---|---|---|
| CEN.PK2-1C | aerobic culture | glucose | 44 | 0.9 |
| CENPK, Δgpd2, Δtpil, gldA*(A160T), yqhD, msgA*(H21Q) | aerobic culture | glucose | 75 | 1.6 |
| CEN.PK2-1C | aerobic culture | sucrose | 41 | 0.9 |
| CENPK, Δgpd2, Δtpil, gldA*(A160T), yqhD, msgA*(H21Q) | aerobic culture | sucrose | 69 | 1.6 |
| CEN.PK2-1C | anaerobic culture | glucose | 11 | 0.2 |
| CENPK, Δgpd2, Δtpil, gldA*(A160T), yqhD, msgA*(H21Q) | anaerobic culture | glucose | 44 | 0.9 |

The production of 1,2-propanediol in a *S. cerevisiae* strain with a mutant MGS was improved under anaerobic or aerobic conditions with glucose or sucrose as compared with the non-modified control strain.

REFERENCES

Cooper R A and Anderson A (1970), *FEBS Lett.* 11: 273-276
Hopper D J and Cooper R A (1971), *FEBS Lett.* 13: 213-216
Hopper D J and Cooper R A (1972), *Biochem. J.* 128: 321-329
Cooper R A (1984), *Annu. Rev. Microbiol.* 38: 49-68
Saadat D and Harrison D H T (1998), *Biochemistry* 37: 10074-10086
Saadat D and Harrison D H T (1999), *Structure* 7: 309-317
Saadat D and Harrison D H T (2000), *Biochemistry* 39: 2950-2960
Marks G T, Susler M, Harrison D H T (2004), *Biochemistry* 43: 3802-3813
Tötemeyer S, Booth N A, Nichols W W, Dunbar B, Booth I R (1998), *Mol. Microbiol.* 27: 553-562
Ferguson G P, Tötmeyer S, MacLean M J, Booth I R (1998), *Arch. Microbiol.* 170:209-219
Garvie E I (1980), *Microbiol. Rev.* 44: 106-139
Cooper R A (1984), *Annu. Rev. Microbiol.* 38: 49-68 Arch. Microbiol. 170: 209-219
Rule G S, Pratt E A, Chin C C Q, Wold F, Ho C (1985), *J. Bacteriol.* 161: 1059-1068
Dong J M, Taylor J S, Latour D J, Iuchi S, Lin E C C (1993), *J. Bacteriol.* 175: 6671-6678
Grabar T B, Zhou S, Shanmugam K T, Yomano L P, Ingram L O (2006), *Biotechnol. Lett.* 28: 1527-1535
Misra K, Banerjee A R, Ray S, Ray M (1995), *Biochem. J.* 305: 999-1003
Cameron D C, Altaras N E, Hoffman M L, Shaw A J (1998), *Biotechnol. Prog.* 14: 116-125
Altaras N E and Cameron D C (2000), *Biotechnol. Prog.* 16: 940-946
Bennett G N and San K Y, (2001), *Appl. Microbiol. Biotechnol.* 55: 1-9
Ko J, Kim I, Yoo S, Min B, Kim K, Park C (2005), *J. Bacteriol.* 187: 5782-5789
Datta R and Henry M, (2006), *J. Chem. Technol. Biotechnol.* 81: 1119-1129
Wasewar K L, (2005), *Chem. Biochem. Eng. Q.* 19: 159-172
The UniProt consortium, (2008), *Nucleic Acids Res.* 36: D190-195
Guldener, U., et al., (1996), *Nucleic Acids Res.* 24: 2519-24
Schiestl, R. H. and Gietz, R. D., (1989), *Curr Genet.* 16: 339-46.
Shevchuk, N. A., et al., (2004), *Nucleic Acids Res.* 32: e19

The invention claimed is:

1. A mutant methylglyoxal synthase (MGS) enzyme comprising a protein sequence selected from the group consisting of SEQ ID NO:1, SEQ ID NO:2, and SEQ ID NO:3, wherein the mutant enzyme has retained more than 50% of the methylglyoxal synthase activity of the parent enzyme, and the methylglyoxal synthase activity of the mutant MGS is not inhibited by orthophosphate.

* * * * *

```
SEQUENCE LISTING

<160> NUMBER OF SEQ ID NOS: 88

<210> SEQ ID NO 1
<211> LENGTH: 152
<212> TYPE: PRT
<213> ORGANISM: Escherichia coli

<400> SEQUENCE: 1

Met Glu Leu Thr Thr Arg Thr Leu Pro Ala Arg Lys His Ile Ala Leu
1               5                   10                  15

Val Ala His Asp His Cys Lys Gln Met Leu Met Ser Trp Val Glu Arg
            20                  25                  30

His Gln Pro Leu Leu Glu Gln His Val Leu Tyr Ala Thr Gly Thr Thr
        35                  40                  45

Gly Asn Leu Ile Ser Arg Ala Thr Gly Met Asn Val Asn Ala Met Leu
    50                  55                  60

Ser Gly Pro Met Gly Gly Asp Gln Gln Val Gly Ala Leu Ile Ser Glu
65                  70                  75                  80

Gly Lys Ile Asp Val Leu Ile Phe Phe Trp Asp Pro Leu Asn Val Val
                85                  90                  95

Pro His Asp Pro Asp Val Lys Ala Leu Leu Arg Leu Ala Thr Val Trp
            100                 105                 110

Asn Ile Pro Val Ala Thr Asn Val Ala Thr Ala Asp Phe Ile Ile Gln
        115                 120                 125
```

Ser Pro His Phe Asn Asp Ala Val Asp Ile Leu Ile Pro Asp Tyr Gln
            130                 135                 140

Arg Tyr Leu Ala Asp Arg Leu Lys
145                 150

<210> SEQ ID NO 2
<211> LENGTH: 152
<212> TYPE: PRT
<213> ORGANISM: Escherichia coli

<400> SEQUENCE: 2

Met Glu Leu Thr Thr Arg Thr Leu Pro Ala Arg Lys His Ile Ala Leu
1               5                   10                  15

Val Ala His Asp Gln Cys Lys Gln Met Leu Met Ser Trp Val Glu Arg
            20                  25                  30

His Gln Pro Leu Leu Glu Gln His Val Leu Tyr Ala Thr Gly Thr Thr
        35                  40                  45

Gly Asn Leu Ile Ser Arg Ala Thr Gly Met Asn Val Asn Ala Met Leu
    50                  55                  60

Ser Gly Pro Met Gly Gly Asp Gln Gln Val Gly Ala Leu Ile Ser Glu
65                  70                  75                  80

Gly Lys Ile Asp Val Leu Ile Phe Phe Trp Asp Pro Leu Asn Ala Val
                85                  90                  95

Pro His Asp Pro Asp Val Lys Ala Leu Leu Arg Leu Ala Thr Val Trp
            100                 105                 110

Asn Ile Pro Val Ala Thr Asn Val Ala Thr Ala Asp Phe Ile Ile Gln
        115                 120                 125

Ser Pro His Phe Asn Asp Ala Val Asp Ile Leu Ile Pro Asp Tyr Gln
    130                 135                 140

Arg Tyr Leu Ala Asp Arg Leu Lys
145                 150

<210> SEQ ID NO 3
<211> LENGTH: 152
<212> TYPE: PRT
<213> ORGANISM: Escherichia coli

<400> SEQUENCE: 3

Met Glu Leu Thr Thr Arg Thr Leu Pro Ala Arg Lys His Ile Ala Leu
1               5                   10                  15

Val Ala His Asp His Cys Lys Gln Met Leu Met Ser Trp Val Glu Arg
            20                  25                  30

His Gln Pro Leu Leu Glu Gln His Val Leu Tyr Ala Thr Gly Thr Thr
        35                  40                  45

Gly Asn Leu Ile Ser Arg Ala Thr Gly Met Asn Val Asn Ala Met Leu
    50                  55                  60

Ser Gly Pro Met Gly Gly Asp Gln Gln Val Gly Ala Leu Ile Ser Glu
65                  70                  75                  80

Gly Lys Ile Asp Val Leu Ile Phe Phe Trp Asp Pro Leu Asn Ala Val
                85                  90                  95

Pro His Asp Pro Asp Val Lys Ala Leu Leu Arg Leu Ala Thr Val Trp
            100                 105                 110

Asn Ile Pro Leu Ala Thr Asn Val Ala Thr Ala Asp Phe Ile Ile Gln
        115                 120                 125

Ser Pro His Phe Asn Asp Ala Val Asp Ile Leu Ile Pro Asp Tyr Gln
    130                 135                 140

Arg Tyr Leu Ala Asp Arg Leu Lys
145                 150

<210> SEQ ID NO 4
<211> LENGTH: 23
<212> TYPE: DNA
<213> ORGANISM: Artificial Sequence
<220> FEATURE:
<223> OTHER INFORMATION: Oligonucleotide

<400> SEQUENCE: 4
caccatggaa ctgacgactc gca                                          23

<210> SEQ ID NO 5
<211> LENGTH: 23
<212> TYPE: DNA
<213> ORGANISM: Artificial Sequence
<220> FEATURE:
<223> OTHER INFORMATION: Oligonucleotide

<400> SEQUENCE: 5
ttacttcaga cggtccgcga gat                                          23

<210> SEQ ID NO 6
<211> LENGTH: 48
<212> TYPE: DNA
<213> ORGANISM: Artificial Sequence
<220> FEATURE:
<223> OTHER INFORMATION: Oligonucleotide

<400> SEQUENCE: 6
ttctgggatc cactaaatgt cgtgccgcac gatcctgacg tcaaagcc               48

<210> SEQ ID NO 7
<211> LENGTH: 48
<212> TYPE: DNA
<213> ORGANISM: Artificial Sequence
<220> FEATURE:
<223> OTHER INFORMATION: Oligonucleotide

<400> SEQUENCE: 7
ggctttgacg tcaggatcgt gcggcacgac atttagtgga tcccagaa               48

<210> SEQ ID NO 8
<211> LENGTH: 42
<212> TYPE: DNA
<213> ORGANISM: Artificial Sequence
<220> FEATURE:
<223> OTHER INFORMATION: Oligonucleotide

<400> SEQUENCE: 8
gcgacggtat ggaacattcc gctcgcgacc aacgtggcaa cg                     42

<210> SEQ ID NO 9
<211> LENGTH: 42
<212> TYPE: DNA
<213> ORGANISM: Artificial Sequence
<220> FEATURE:
<223> OTHER INFORMATION: Oligonucleotide

<400> SEQUENCE: 9
cgttgccacg ttggtcgcga gcggaatgtt ccataccgtc gc                     42

<210> SEQ ID NO 10
<211> LENGTH: 45
<212> TYPE: DNA
<213> ORGANISM: Artificial Sequence

```
<220> FEATURE:
<223> OTHER INFORMATION: Oligonucleotide

<400> SEQUENCE: 10
ctggtggcac acgatcaatg caaacagatg ctgatgagct gggtg            45

<210> SEQ ID NO 11
<211> LENGTH: 45
<212> TYPE: DNA
<213> ORGANISM: Artificial Sequence
<220> FEATURE:
<223> OTHER INFORMATION: Oligonucleotide

<400> SEQUENCE: 11
cacccagctc atcagcatct gtttgcattg atcgtgtgcc accag            45

<210> SEQ ID NO 12
<211> LENGTH: 24
<212> TYPE: DNA
<213> ORGANISM: Artificial Sequence
<220> FEATURE:
<223> OTHER INFORMATION: Oligonucleotide

<400> SEQUENCE: 12
ccgacagtaa gacgggtaag cctg                                   24

<210> SEQ ID NO 13
<211> LENGTH: 22
<212> TYPE: DNA
<213> ORGANISM: Artificial Sequence
<220> FEATURE:
<223> OTHER INFORMATION: Oligonucleotide

<400> SEQUENCE: 13
agcttagtaa agccctcgct ag                                     22

<210> SEQ ID NO 14
<211> LENGTH: 100
<212> TYPE: DNA
<213> ORGANISM: Artificial Sequence
<220> FEATURE:
<223> OTHER INFORMATION: Oligonucleotide

<400> SEQUENCE: 14
catgggctag ctacgtatta attaaagatc tcctagggag ctcaccggtt aaaaataaga    60
gttaccttaa atggtaactc ttattttttt aggcgcgcca                        100

<210> SEQ ID NO 15
<211> LENGTH: 100
<212> TYPE: DNA
<213> ORGANISM: Artificial Sequence
<220> FEATURE:
<223> OTHER INFORMATION: Oligonucleotide

<400> SEQUENCE: 15
agcttggcgc gcctaaaaaa ataagagtta ccatttaagg taactcttat ttttaaccgg    60
tgagctccct aggagatctt taattaatac gtagctagcc                        100

<210> SEQ ID NO 16
<211> LENGTH: 43
<212> TYPE: DNA
<213> ORGANISM: Artificial Sequence
<220> FEATURE:
<223> OTHER INFORMATION: Oligonucleotide

<400> SEQUENCE: 16
```

```
cgatgcacgt catgaacaac tttaatctgc acaccccaac ccg            43
```

<210> SEQ ID NO 17
<211> LENGTH: 29
<212> TYPE: DNA
<213> ORGANISM: Artificial Sequence
<220> FEATURE:
<223> OTHER INFORMATION: Oligonucleotide

<400> SEQUENCE: 17

```
ctagctagct tagcgggcgg cttcgtata                            29
```

<210> SEQ ID NO 18
<211> LENGTH: 48
<212> TYPE: DNA
<213> ORGANISM: Artificial Sequence
<220> FEATURE:
<223> OTHER INFORMATION: Oligonucleotide

<400> SEQUENCE: 18

```
ggttcagaat ccaacgcaga agcggtgata tcccgtaaaa ccacaggc       48
```

<210> SEQ ID NO 19
<211> LENGTH: 48
<212> TYPE: DNA
<213> ORGANISM: Artificial Sequence
<220> FEATURE:
<223> OTHER INFORMATION: Oligonucleotide

<400> SEQUENCE: 19

```
gcctgtggtt ttacgggata tcaccgcttc tgcgttggat tctgaacc       48
```

<210> SEQ ID NO 20
<211> LENGTH: 45
<212> TYPE: DNA
<213> ORGANISM: Artificial Sequence
<220> FEATURE:
<223> OTHER INFORMATION: Oligonucleotide

<400> SEQUENCE: 20

```
gacaccaaaa tcgtcgctgg cacacctgca cgtctgctag cggcg          45
```

<210> SEQ ID NO 21
<211> LENGTH: 45
<212> TYPE: DNA
<213> ORGANISM: Artificial Sequence
<220> FEATURE:
<223> OTHER INFORMATION: Oligonucleotide

<400> SEQUENCE: 21

```
cgccgctagc agacgtgcag gtgtgccagc gacgattttg gtgtc          45
```

<210> SEQ ID NO 22
<211> LENGTH: 105
<212> TYPE: DNA
<213> ORGANISM: Artificial Sequence
<220> FEATURE:
<223> OTHER INFORMATION: Oligonucleotide

<400> SEQUENCE: 22

```
gttaactacg gatgtacatt atggaactga cgactcgcac tttacctgcg cggaaacata    60
ttgcgctggt ggcacacgat caggcctggt gatgatggcg ggatc                   105
```

<210> SEQ ID NO 23
<211> LENGTH: 120

```
<212> TYPE: DNA
<213> ORGANISM: Artificial Sequence
<220> FEATURE:
<223> OTHER INFORMATION: Oligonucleotide

<400> SEQUENCE: 23
gggaaattaa gttaccggta gtgcctgttg catacagtac gtgttgttcc agtaacggtt     60
gatgccgttc cacccagctc atcagcatct gtttgcattc agaagaactc gtcaagaagg   120

<210> SEQ ID NO 24
<211> LENGTH: 100
<212> TYPE: DNA
<213> ORGANISM: Artificial sequence
<220> FEATURE:
<223> OTHER INFORMATION: Oligonucleotide

<400> SEQUENCE: 24
tccagtcgcc gcatttcaac gacgcggtcg atattctgat ccccgattat cagcgttatc     60
tcgcggaccg tctgaagtaa tgtaggctgg agctgcttcg                          100

<210> SEQ ID NO 25
<211> LENGTH: 100
<212> TYPE: DNA
<213> ORGANISM: Artificial sequence
<220> FEATURE:
<223> OTHER INFORMATION: Oligonucleotide

<400> SEQUENCE: 25
tgtggaaata ctgaaaaatc tggatgtgcc ggtggcgaga aaaccgtaag aaacaggtgg     60
cgtttgccac ctgtgcaata catatgaata tcctccttag                          100

<210> SEQ ID NO 26
<211> LENGTH: 41
<212> TYPE: DNA
<213> ORGANISM: Artificial Sequence
<220> FEATURE:
<223> OTHER INFORMATION: Synthetic Ptrc01 promoter

<400> SEQUENCE: 26
gagctgttga ctattaatca tccggctcga ataatgtgtg g                         41

<210> SEQ ID NO 27
<211> LENGTH: 61
<212> TYPE: DNA
<213> ORGANISM: Artificial Sequence
<220> FEATURE:
<223> OTHER INFORMATION: Oligonucleotide

<400> SEQUENCE: 27
atgcttgctg tcagaagatt aacaagatac acattcctta gtttatcatt atcaatactc     60
g                                                                    61

<210> SEQ ID NO 28
<211> LENGTH: 23
<212> TYPE: DNA
<213> ORGANISM: Artificial Sequence
<220> FEATURE:
<223> OTHER INFORMATION: Oligonucleotide

<400> SEQUENCE: 28
atcctcgaaa ctaagttctt ggt                                             23

<210> SEQ ID NO 29
<211> LENGTH: 42
```

<212> TYPE: DNA
<213> ORGANISM: Artificial Sequence
<220> FEATURE:
<223> OTHER INFORMATION: Oligonucleotide

<400> SEQUENCE: 29
aaacaccaga acttagtttc gaactagttt attcccactc tt         42

<210> SEQ ID NO 30
<211> LENGTH: 62
<212> TYPE: DNA
<213> ORGANISM: Artificial Sequence
<220> FEATURE:
<223> OTHER INFORMATION: Oligonucleotide

<400> SEQUENCE: 30
tgaaatataa ataacgttct taatactaac ataactataa actagtatgg accgcattat    60
tc                                                                   62

<210> SEQ ID NO 31
<211> LENGTH: 66
<212> TYPE: DNA
<213> ORGANISM: Artificial Sequence
<220> FEATURE:
<223> OTHER INFORMATION: Oligonucleotide

<400> SEQUENCE: 31
cctggatgta tttacccggt gattgaataa tgcggtccat actagtttat agttatgtta    60
gtatta                                                               66

<210> SEQ ID NO 32
<211> LENGTH: 60
<212> TYPE: DNA
<213> ORGANISM: Artificial Sequence
<220> FEATURE:
<223> OTHER INFORMATION: Oligonucleotide

<400> SEQUENCE: 32
gaggcaagct aaacagatct ctagacctag gtacccgccg gcaaattaaa gccttcgagc    60

<210> SEQ ID NO 33
<211> LENGTH: 62
<212> TYPE: DNA
<213> ORGANISM: Artificial Sequence
<220> FEATURE:
<223> OTHER INFORMATION: Oligonucleotide

<400> SEQUENCE: 33
gcttgagaag gttttgggac gctcgaaggc tttaatttgc taggtctaga gatctgttta    60
gc                                                                   62

<210> SEQ ID NO 34
<211> LENGTH: 64
<212> TYPE: DNA
<213> ORGANISM: Artificial Sequence
<220> FEATURE:
<223> OTHER INFORMATION: Oligonucleotide

<400> SEQUENCE: 34
ctattcgtca tcgatgtcta gctcttcaat catctccggt ccactagtgg atctgatatc    60
acct                                                                 64

<210> SEQ ID NO 35
<211> LENGTH: 20

```
<212> TYPE: DNA
<213> ORGANISM: Artificial Sequence
<220> FEATURE:
<223> OTHER INFORMATION: Oligonucleotide

<400> SEQUENCE: 35
atgcttgctg tcagaagatt                                                 20

<210> SEQ ID NO 36
<211> LENGTH: 20
<212> TYPE: DNA
<213> ORGANISM: Artificial Sequence
<220> FEATURE:
<223> OTHER INFORMATION: Oligonucleotide

<400> SEQUENCE: 36
tagtatggac cgcattattc                                                 20

<210> SEQ ID NO 37
<211> LENGTH: 60
<212> TYPE: DNA
<213> ORGANISM: Artificial Sequence
<220> FEATURE:
<223> OTHER INFORMATION: Oligonucleotide

<400> SEQUENCE: 37
atgtctgccc ctaagaagat cgtcgttttg ccaggtgacc agctggagct catagcttca     60

<210> SEQ ID NO 38
<211> LENGTH: 60
<212> TYPE: DNA
<213> ORGANISM: Artificial Sequence
<220> FEATURE:
<223> OTHER INFORMATION: Oligonucleotide

<400> SEQUENCE: 38
tgcgggttgg ggtgtgcaga ttaaagttgt tcatactagt ggatccacta gttctagaaa     60

<210> SEQ ID NO 39
<211> LENGTH: 60
<212> TYPE: DNA
<213> ORGANISM: Artificial Sequence
<220> FEATURE:
<223> OTHER INFORMATION: Oligonucleotide

<400> SEQUENCE: 39
catagcaatc taatctaagt tttctagaac tagtggatcc actagtatga acaactttaa     60

<210> SEQ ID NO 40
<211> LENGTH: 60
<212> TYPE: DNA
<213> ORGANISM: Artificial Sequence
<220> FEATURE:
<223> OTHER INFORMATION: Oligonucleotide

<400> SEQUENCE: 40
tgaaatataa ataacgttct taatactaac ataactataa actagtttag cgggcggctt     60

<210> SEQ ID NO 41
<211> LENGTH: 60
<212> TYPE: DNA
<213> ORGANISM: Artificial Sequence
<220> FEATURE:
<223> OTHER INFORMATION: Oligonucleotide

<400> SEQUENCE: 41
tgtcagccgc cgtatatacg aagccgcccg ctaaactagt ttatagttat gttagtatta     60
```

<210> SEQ ID NO 42
<211> LENGTH: 60
<212> TYPE: DNA
<213> ORGANISM: Artificial Sequence
<220> FEATURE:
<223> OTHER INFORMATION: Oligonucleotide

<400> SEQUENCE: 42
ctccatgtcg ctggccgggt gacccggcgg ggacgaggca gcaaattaaa gccttcgagc    60

<210> SEQ ID NO 43
<211> LENGTH: 60
<212> TYPE: DNA
<213> ORGANISM: Artificial Sequence
<220> FEATURE:
<223> OTHER INFORMATION: Oligonucleotide

<400> SEQUENCE: 43
gcttgagaag gttttgggac gctcgaaggc tttaatttgc tgcctcgtcc ccgccgggtc    60

<210> SEQ ID NO 44
<211> LENGTH: 60
<212> TYPE: DNA
<213> ORGANISM: Artificial Sequence
<220> FEATURE:
<223> OTHER INFORMATION: Oligonucleotide

<400> SEQUENCE: 44
ttaagcaagg attttcttaa cttcttcggc gacagcatca cagtatagcg accagcattc    60

<210> SEQ ID NO 45
<211> LENGTH: 21
<212> TYPE: DNA
<213> ORGANISM: Artificial Sequence
<220> FEATURE:
<223> OTHER INFORMATION: Oligonucleotide

<400> SEQUENCE: 45
atgtctgccc ctaagaagat c                                              21

<210> SEQ ID NO 46
<211> LENGTH: 20
<212> TYPE: DNA
<213> ORGANISM: Artificial Sequence
<220> FEATURE:
<223> OTHER INFORMATION: Oligonucleotide

<400> SEQUENCE: 46
actagtttag cgggcggctt                                                20

<210> SEQ ID NO 47
<211> LENGTH: 60
<212> TYPE: DNA
<213> ORGANISM: Artificial Sequence
<220> FEATURE:
<223> OTHER INFORMATION: Oligonucleotide

<400> SEQUENCE: 47
atgtcgaaag ctacatataa ggaacgtgct gctactcatc gccagatctg tttagcttgc    60

<210> SEQ ID NO 48
<211> LENGTH: 40
<212> TYPE: DNA
<213> ORGANISM: Artificial Sequence
<220> FEATURE:
<223> OTHER INFORMATION: Oligonucleotide

<400> SEQUENCE: 48
gtgcgagtcg tcagttccat aatacgcaaa ccgcctctcc                               40

<210> SEQ ID NO 49
<211> LENGTH: 40
<212> TYPE: DNA
<213> ORGANISM: Artificial Sequence
<220> FEATURE:
<223> OTHER INFORMATION: Oligonucleotide

<400> SEQUENCE: 49
ggagaggcgg tttgcgtatt atggaactga cgactcgcac                               40

<210> SEQ ID NO 50
<211> LENGTH: 60
<212> TYPE: DNA
<213> ORGANISM: Artificial Sequence
<220> FEATURE:
<223> OTHER INFORMATION: Oligonucleotide

<400> SEQUENCE: 50
ttagttttgc tggccgcatc ttctcaaata tgcttcectt tacttcagac ggtccgcgag         60

<210> SEQ ID NO 51
<211> LENGTH: 18
<212> TYPE: DNA
<213> ORGANISM: Artificial Sequence
<220> FEATURE:
<223> OTHER INFORMATION: Oligonucleotide

<400> SEQUENCE: 51
ggaactgacg actcgcac                                                      18

<210> SEQ ID NO 52
<211> LENGTH: 20
<212> TYPE: DNA
<213> ORGANISM: Artificial Sequence
<220> FEATURE:
<223> OTHER INFORMATION: Oligonucleotide

<400> SEQUENCE: 52
ttagtttcta gagttgatga                                                    20

<210> SEQ ID NO 53
<211> LENGTH: 158
<212> TYPE: PRT
<213> ORGANISM: Treponema socranskii

<400> SEQUENCE: 53

Met Arg Arg Lys Leu Arg Ile Ala Leu Val Ala His Asp Asn Arg Lys
1               5                   10                  15

Ala Asp Ile Val Asp Trp Ala Leu Asn Asn Ala Glu Met Leu Ser Gln
            20                  25                  30

His Arg Leu Phe Gly Thr Gly Thr Thr Gly Thr Leu Val Arg Glu Ser
        35                  40                  45

Phe Met Lys Arg Gly Ile Ala Ser Asp Ile Thr Cys Met His Ser Gly
    50                  55                  60

Pro Met Gly Gly Asp Ala Glu Ile Ala Ala Leu Val Val Arg Lys Glu
65                  70                  75                  80

Ile Asp Phe Ala Val Phe Phe Ile Asp Asp Leu Asn Pro Gln Pro His
                85                  90                  95

Glu Ala Asp Ile Gln Met Leu Leu Arg Gln Cys Arg Ile His Asn Ile

```
                100                 105                 110
Pro Ile Ala Cys Asn Arg Tyr Ser Ala Asp Leu Met Ile Thr Ser Ser
            115                 120                 125

Leu Trp Asp Asp Ala Gly Tyr Val Pro Lys Asp Pro Ile Tyr Ala Pro
130                 135                 140

Phe Asp Arg Lys Ala Phe Glu Glu Ser Leu Lys Val Lys Glu
145                 150                 155
```

<210> SEQ ID NO 54
<211> LENGTH: 143
<212> TYPE: PRT
<213> ORGANISM: Coxiella burnetii

<400> SEQUENCE: 54

```
Met Thr Val Lys Lys Ile Ala Leu Val Ala His Asp Arg Met Lys Lys
1               5                   10                  15

Glu Leu Ile Glu Trp Ile Lys Lys His Gln Asn Leu Leu Lys His His
            20                  25                  30

Glu Leu Tyr Ala Thr Gly Ser Thr Gly Gln Ala Ile Glu Lys Thr Leu
        35                  40                  45

Asn Val Thr Val Thr Lys Met Glu Ser Gly Pro Leu Gly Gly Asp Leu
    50                  55                  60

Gln Leu Gly Ala Lys Ile Val Asn Lys Glu Ile Asp Ile Leu Ile Phe
65                  70                  75                  80

Phe Trp Asp Pro Leu Glu Ala Gln Pro His Asp Pro Asp Val Arg Ala
                85                  90                  95

Leu Leu Arg Ile Ala Val Val Trp Asn Leu Pro Val Ala Cys Asn Ala
            100                 105                 110

Ser Thr Ala Asp Tyr Leu Leu Thr Ser Pro Leu Phe Ser Asp Tyr
        115                 120                 125

His Pro Glu Thr Pro Asp Tyr Glu Ala Tyr Arg Asn Arg Ile Ile
    130                 135                 140
```

<210> SEQ ID NO 55
<211> LENGTH: 135
<212> TYPE: PRT
<213> ORGANISM: Ralstonia solanacearum

<400> SEQUENCE: 55

```
Met Pro Lys Arg Arg Arg Ile Ala Leu Ile Ala His Asp His Lys Lys
1               5                   10                  15

Asp Asp Met Ile Ala Phe Ala Gln Thr His Lys Ala Phe Leu Met Arg
            20                  25                  30

Cys Asp Leu Leu Ala Thr Gly Thr Thr Gly Gly Arg Leu Gln Asp Glu
        35                  40                  45

Val Gly Leu Ser Val Gln Arg Met Leu Ser Gly Pro Trp Gly Gly Asp
    50                  55                  60

Leu Gln Ile Gly Ala Gln Leu Ala Glu Gly Arg Val Asp Ala Val Ile
65                  70                  75                  80

Phe Leu Arg Asp Pro Met Thr Pro Gln Pro His Glu Pro Asp Ile Asn
                85                  90                  95

Ala Leu Val Arg Ala Cys Asp Val His Asn Ile Pro Cys Ala Thr Asn
            100                 105                 110

Leu Ala Thr Ala Asp Leu Val Met Ile Ala Leu Gly Leu Ala Gln Pro
        115                 120                 125

Asp Pro Lys Glu Ile His Ala
    130                 135
```

-continued

```
<210> SEQ ID NO 56
<211> LENGTH: 130
<212> TYPE: PRT
<213> ORGANISM: Burkholderia mallei

<400> SEQUENCE: 56

Met Ser Thr Pro Arg Ile Ala Leu Ile Ala His Asp Ala Lys Lys Asp
1               5                   10                  15

Asp Ile Val Ala Leu Ala Gly Ala Tyr Arg Ala Thr Leu Ala Gln Cys
                20                  25                  30

Arg Leu Val Ala Thr Gly Thr Thr Gly Gly Arg Ile Ala Gln Ala His
            35                  40                  45

Gly Leu Asp Val Glu Arg Lys Leu Ser Gly Pro Leu Gly Gly Asp Leu
        50                  55                  60

Gln Ile Gly Ala Glu Leu Ala Asp Gly Arg Val Asp Ile Val Ile Phe
65                  70                  75                  80

Leu Arg Asp Pro Met Thr Ala Gln Pro His Asp Pro Asp Ile Thr Ala
                85                  90                  95

Leu Val Arg Ala Cys Asp Val His Asp Val Pro Val Ala Thr Asn Val
            100                 105                 110

Ala Thr Ala Arg Val Leu Leu Asp Asp Leu Ala Arg Arg Leu Thr Ala
        115                 120                 125

Asn Ala
    130

<210> SEQ ID NO 57
<211> LENGTH: 125
<212> TYPE: PRT
<213> ORGANISM: Brucella melitensis

<400> SEQUENCE: 57

Met Thr Gln Arg Leu Arg Ile Ala Leu Ile Ala His Asp Gln Lys Lys
1               5                   10                  15

Asp Asp Met Val Ala Phe Ala Arg Ala His Glu Gln Ala Leu Ser Arg
                20                  25                  30

Tyr Asp Ile Val Ala Thr Gly Thr Thr Gly Gly Leu Ile Gln Asp Ala
            35                  40                  45

Cys Pro Ser Leu Asn Ile His Arg Val Lys Ser Gly Pro Leu Gly Gly
        50                  55                  60

Asp Gln Gln Ile Gly Ala Met Ile Ala Glu Gly Thr Val Glu Val Leu
65                  70                  75                  80

Ile Phe Phe Ile Asp Pro Leu Ser Pro Leu Pro His Asp Val Asp Val
                85                  90                  95

Lys Ala Leu Thr Arg Leu Gly Ser Val Tyr Asp Ile Pro Met Ala Leu
            100                 105                 110

Asn Arg Ala Thr Ala Glu Lys Leu Val Arg Ala Leu Asp
        115                 120                 125

<210> SEQ ID NO 58
<211> LENGTH: 127
<212> TYPE: PRT
<213> ORGANISM: Agrobacterium tumefaciens

<400> SEQUENCE: 58

Met Glu Gly Gln Arg Cys Ile Ala Leu Ile Ala His Asp Glu Lys Lys
1               5                   10                  15

Asp Asp Met Ala Asp Phe Ala Arg His His Gln Lys Val Leu Ala Ser
```

```
              20                  25                  30
Phe Arg Ile Val Ala Thr Gly Thr Gly Gly Arg Val Gln Glu Ala
             35                  40                  45
Cys Pro Gly Leu Glu Val Ile Arg Leu Lys Ser Gly Pro Leu Gly Gly
         50                  55                  60
Asp Gln Gln Ile Gly Ala Met Ile Ala Thr Gly Glu Val Asp Met Leu
65                  70                  75                  80
Ile Phe Phe Thr Asp Pro Leu Thr Ala Met Pro His Asp Val Asp Val
             85                  90                  95
Lys Ala Leu Thr Arg Leu Ala Thr Val Tyr Asp Ile Pro Met Ala Leu
            100                 105                 110
Asn Arg Ala Thr Ala Glu Asn Leu Ile Asp Phe Asn Ser Ala Asp
            115                 120                 125

<210> SEQ ID NO 59
<211> LENGTH: 126
<212> TYPE: PRT
<213> ORGANISM: Rhizobium meliloti

<400> SEQUENCE: 59

Met Ala Asp Arg Lys Cys Leu Ala Leu Ile Ala His Asp Gln Lys Lys
1               5                  10                  15
Asp Asp Leu Ala Ala Phe Ala Lys Ala Asn Glu Ala Val Leu Ser Lys
             20                  25                  30
Trp Lys Ile Val Ala Thr Gly Thr Thr Gly Gly Arg Val Leu Asp Val
             35                  40                  45
Cys Pro Ala Leu Asp Ile Val Arg Leu Lys Ser Gly Pro Leu Gly Gly
         50                  55                  60
Asp Gln Gln Ile Gly Ala Leu Ile Ala Thr Gly Asp Val Asp Cys Leu
65                  70                  75                  80
Ile Phe Phe Val Asp Pro Leu Thr Ala Met Pro His Asp Val Asp Val
             85                  90                  95
Lys Ala Leu Met Arg Leu Ala Ile Val Tyr Asp Ile Pro Met Ala Leu
            100                 105                 110
Asn Arg Ala Thr Ala Glu Gln Leu Ile Asp Phe Arg Arg Asn
            115                 120                 125

<210> SEQ ID NO 60
<211> LENGTH: 126
<212> TYPE: PRT
<213> ORGANISM: Symbiobacterium thermophilum

<400> SEQUENCE: 60

Met Arg Ile Ala Leu Ile Ala His Asp Asn Arg Lys Gln Asp Met Leu
1               5                  10                  15
Lys Phe Val Lys Asp His Lys Ser Ala Phe Glu Gly His Gln Leu Phe
             20                  25                  30
Ala Thr Gly Thr Thr Gly Lys Leu Ile Arg Glu His Thr Gly Leu Asp
             35                  40                  45
Val His Cys Phe Leu Ser Gly Pro Leu Gly Gly Asp Gln Gln Ile Gly
         50                  55                  60
Ser Arg Val Ala Thr Gly Glu Ile Asp Met Val Ile Phe Leu Arg Asp
65                  70                  75                  80
Pro Leu Thr Ala Met Pro His Glu Pro Asp Val Gln Gly Leu Leu Arg
             85                  90                  95
Leu Cys Asp Val Arg Asp Ile Pro Val Ala Thr Asn Leu Gly Ser Ala
            100                 105                 110
```

```
Arg Met Phe Ala Asp Asp Leu Met Arg Leu Lys Asp Val Lys
        115                 120                 125
```

<210> SEQ ID NO 61
<211> LENGTH: 126
<212> TYPE: PRT
<213> ORGANISM: Borrelia burgdorferi

<400> SEQUENCE: 61

```
Met Glu Lys Lys Ile Ala Leu Ile Ala His Asp Lys Lys Lys Glu Asp
1               5                   10                  15

Leu Val Asn Phe Val Lys Gln Asn Tyr Leu Phe Leu Ser Lys Phe Lys
            20                  25                  30

Leu Ile Ala Thr Gly Thr Thr Gly Ser Lys Ile Gln Gln Ala Thr Asp
        35                  40                  45

Leu Thr Ile Phe Lys Tyr Lys Ser Gly Pro Met Gly Gly Asp Gln Gln
    50                  55                  60

Ile Gly Ala Glu Val Ala Glu Gly Asn Ile Leu Ala Ile Phe Phe Phe
65                  70                  75                  80

Arg Asp Pro Leu Thr Ser Gln Pro His Glu Pro Asp Val Ser Ala Leu
                85                  90                  95

Ile Arg Leu Cys Asp Val His Lys Ile Pro Leu Ala Thr Asn Val Lys
            100                 105                 110

Thr Ala Glu Ile Leu Ile Lys Gly Leu Glu Ser Leu Ile Phe
        115                 120                 125
```

<210> SEQ ID NO 62
<211> LENGTH: 126
<212> TYPE: PRT
<213> ORGANISM: Borrelia garinii

<400> SEQUENCE: 62

```
Met Glu Lys Lys Ile Ala Leu Ile Ala His Asp Lys Lys Lys Asp Asp
1               5                   10                  15

Leu Val Asn Phe Val Lys Gln Asn Tyr Leu Phe Leu Ser Lys Phe Lys
            20                  25                  30

Leu Ile Ala Thr Gly Thr Thr Gly Ser Arg Ile Gln Gln Ala Thr Asp
        35                  40                  45

Leu Thr Ile Ile Lys Tyr Lys Ser Gly Pro Met Gly Gly Asp Gln Gln
    50                  55                  60

Ile Gly Ala Glu Val Ala Glu Gly Asn Val Leu Ala Ile Phe Phe Phe
65                  70                  75                  80

Arg Asp Pro Leu Thr Asn Gln Pro His Glu Pro Asp Val Ser Ala Leu
                85                  90                  95

Ile Arg Leu Cys Asp Val His Asn Ile Pro Leu Ala Thr Asn Val Lys
            100                 105                 110

Thr Ala Glu Ile Leu Ile Lys Gly Phe Glu Gly Leu Asn Thr
        115                 120                 125
```

<210> SEQ ID NO 63
<211> LENGTH: 119
<212> TYPE: PRT
<213> ORGANISM: Clostridium perfringens

<400> SEQUENCE: 63

```
Met Lys Ile Ala Leu Ile Ala His Asp Lys Lys Lys Glu Glu Met Ile
1               5                   10                  15

Glu Leu Ala Lys Asp Phe Glu Asp Lys Leu Ser Lys His Ile Leu Val
```

-continued

```
                 20                  25                  30
Ala Thr Gly Thr Thr Gly Leu Lys Ile Met Gln Asn Thr Ser Leu Glu
             35                  40                  45

Val Lys Arg Cys Lys Ser Gly Pro Leu Gly Gly Asp Gln Glu Ile Gly
         50                  55                  60

Ala Met Val Ala Asn His Asp Val Asp Met Val Ile Phe Leu Arg Asp
65                  70                  75                  80

Pro Leu Thr Ala Gln Pro His Glu Pro Asp Ile Ser Ala Leu Leu Arg
             85                  90                  95

Leu Cys Asp Val Tyr Lys Val Pro Leu Ala Thr Asn Thr Glu Ser Ala
            100                 105                 110

Lys Leu Ile Met Ala Asp Ile
            115

<210> SEQ ID NO 64
<211> LENGTH: 140
<212> TYPE: PRT
<213> ORGANISM: Oceanobacillus iheyensis

<400> SEQUENCE: 64

Met Asn Ile Ala Leu Ile Ala His Asp Glu Lys Lys Glu Asp Met Ile
1               5                  10                  15

Gln Phe Thr Thr Ala Tyr Thr His Val Leu Ser Lys His Arg Leu Phe
             20                  25                  30

Ala Thr Gly Thr Thr Gly Met Lys Ile Ser Asn Ala Thr Gly Leu Gln
             35                  40                  45

Ile His Arg Phe Gln Ser Gly Pro Leu Gly Gly Asp Gln Gln Ile Gly
         50                  55                  60

Ala Met Ile Ala Asn Gly Glu Met Asp Met Ile Ile Phe Phe Arg Asp
65                  70                  75                  80

Pro Leu Thr Ala Gln Pro His Glu Pro Asp Val Ser Ala Leu Met Arg
             85                  90                  95

Leu Cys Asp Val His Gln Ile Pro Leu Val Thr Asn Ile Ala Gly Ala
            100                 105                 110

Glu Ile Phe Ile His Gly Leu Ser Arg Gly Asp Leu Lys Trp Arg Glu
            115                 120                 125

Ile Ile Lys Glu Arg Gln Glu Lys Glu Gly Thr Pro
            130                 135                 140

<210> SEQ ID NO 65
<211> LENGTH: 129
<212> TYPE: PRT
<213> ORGANISM: Thermoanaerobacter tengcongensis

<400> SEQUENCE: 65

Met Asn Ile Ala Leu Ile Ala His Asp Gln Lys Lys Glu Leu Met Val
1               5                  10                  15

Asn Phe Ala Ile Ala Tyr Lys His Ile Phe Glu Lys Cys Asn Leu Tyr
             20                  25                  30

Ala Thr Gly His Thr Gly Gln Leu Ile Lys Glu Ala Thr Gly Leu Asp
             35                  40                  45

Val His Cys Leu Leu Pro Gly Leu Gly Gly Asp Gln Gln Ile Gly
         50                  55                  60

Ala Leu Ile Ala Glu Asn Lys Ile Asp Leu Val Ile Phe Leu Arg Asp
65                  70                  75                  80

Pro Leu Thr Val Gln Pro His Glu Pro Asp Ile Leu Ala Leu Leu Arg
             85                  90                  95
```

```
Val Cys Asp Val His Ser Ile Pro Val Ala Thr Asn Ile Ala Thr Ala
            100                 105                 110

Glu Val Leu Leu Lys Gly Met Glu Met Gly Leu Leu Asp Trp Arg Gln
        115                 120                 125

Ile
```

<210> SEQ ID NO 66
<211> LENGTH: 134
<212> TYPE: PRT
<213> ORGANISM: Thermoanaerobacterium thermosaccharolyticum

<400> SEQUENCE: 66

```
Met Val Asn Leu Asn Ile Ala Leu Ile Ala His Asp Met Lys Lys Ser
1               5                   10                  15

Leu Met Ile Asp Phe Ala Ile Ala Tyr Lys Asp Ile Leu Glu Lys Cys
            20                  25                  30

Asn Ile Tyr Ala Thr Gly Ala Thr Gly Gln Leu Val Glu Glu Ala Thr
        35                  40                  45

Gly Ile Lys Val Asn Lys Phe Leu Pro Gly Pro Met Gly Gly Asp Gln
    50                  55                  60

Gln Ile Gly Ala Met Ile Ala Glu Asp Lys Met Asp Leu Val Ile Phe
65                  70                  75                  80

Leu Arg Asp Pro Leu Thr Ala Gln Pro His Glu Pro Asp Ile Leu Ala
                85                  90                  95

Leu Leu Arg Val Cys Asp Val His Ser Ile Pro Leu Ala Thr Asn Leu
            100                 105                 110

Ala Thr Ala Glu Val Leu Ile Lys Gly Leu Asp Ala Gly Leu Leu Glu
        115                 120                 125

Trp Arg Asn Ala Val Lys
    130
```

<210> SEQ ID NO 67
<211> LENGTH: 144
<212> TYPE: PRT
<213> ORGANISM: Geobacillus kaustophilus

<400> SEQUENCE: 67

```
Met Lys Ile Ala Leu Ile Ala His Asp Gln Lys Glu Glu Met Val
1               5                   10                  15

Ala Phe Ala Thr Ala Tyr Ala Pro Val Leu Ala Asn His Glu Leu Tyr
            20                  25                  30

Ala Thr Gly Thr Thr Gly Leu Arg Ile Gln Glu Ala Thr Gly Leu Pro
        35                  40                  45

Val His Arg Phe Gln Ser Gly Pro Tyr Gly Gly Asp Gln Glu Ile Gly
    50                  55                  60

Ala Met Ile Ala Arg Asn Glu Met Asp Leu Val Ile Phe Phe Arg Asp
65                  70                  75                  80

Pro Leu Thr Ala Gln Pro His Glu Pro Asp Ile Ser Ala Leu Met Arg
                85                  90                  95

Leu Cys Asp Val Tyr Ala Val Pro Leu Ala Thr Asn Ile Gly Thr Ala
            100                 105                 110

Glu Leu Leu Ile Arg Ala Leu Glu Arg Gly Asp Leu Ala Trp Arg Ser
        115                 120                 125

Ile Val Arg Gly Gln Thr Lys Gly Gly Glu Glu Ser Lys Thr Glu Arg
    130                 135                 140
```

<210> SEQ ID NO 68
<211> LENGTH: 131
<212> TYPE: PRT
<213> ORGANISM: Bacillus cereus

<400> SEQUENCE: 68

```
Met Lys Ile Ala Leu Ile Ala His Asp Lys Lys Lys Asn Asp Met Val
1               5                   10                  15

Ser Phe Ala Tyr Ala Tyr Lys Pro Ile Phe Glu Gln His Glu Leu Phe
            20                  25                  30

Ala Thr Gly Thr Thr Gly Leu Arg Ile Met Glu Ala Thr Gly Leu Val
        35                  40                  45

Ile Thr Arg Tyr Gln Ser Gly Pro Leu Gly Gly Asp Gln Glu Ile Gly
    50                  55                  60

Ala Met Ile Ala Lys Asn Asp Leu Asp Met Val Ile Phe Phe Arg Asp
65                  70                  75                  80

Pro Leu Thr Ala Gln Pro His Glu Pro Asp Val Asn Ala Leu Leu Arg
                85                  90                  95

Leu Cys Asp Val Tyr Ala Ile Pro Leu Ala Thr Asn Met Ala Ser Ala
            100                 105                 110

Glu Met Leu Met His Ala Leu Glu Arg Gly Asp Leu Asp Tyr Arg Lys
        115                 120                 125

Leu Arg Lys
    130
```

<210> SEQ ID NO 69
<211> LENGTH: 142
<212> TYPE: PRT
<213> ORGANISM: Bacillus clausii

<400> SEQUENCE: 69

```
Met Lys Ile Ala Leu Ile Ala His Asp Lys Lys Lys Gln Glu Leu Val
1               5                   10                  15

Asp Phe Cys Val Ala Tyr Glu Pro Ile Leu Lys Glu His Glu Leu Tyr
            20                  25                  30

Ala Thr Gly Thr Thr Gly Thr Arg Ile Met Glu Ala Thr Glu Leu Val
        35                  40                  45

Val Thr Arg Phe Lys Ser Gly Pro Leu Gly Gly Asp Gln Gln Ile Gly
    50                  55                  60

Ala Leu Val Ala Glu Asn Gln Phe Asp Leu Ile Leu Phe Met Arg Asp
65                  70                  75                  80

Pro Leu Thr Ala Gln Pro His Glu Pro Asp Val Thr Ala Leu Ile Arg
                85                  90                  95

Leu Cys Asp Val Gln Ser Val Pro Leu Ala Thr Asn Met Gly Thr Ala
            100                 105                 110

Glu Ile Leu Ile Lys Gly Leu Glu Arg Gly Asp Phe Ala Phe Arg Asp
        115                 120                 125

Ile Ile His Glu Gln Glu Lys Ala Asn Pro Leu Lys Glu Gly
    130                 135                 140
```

<210> SEQ ID NO 70
<211> LENGTH: 138
<212> TYPE: PRT
<213> ORGANISM: Bacillus halodurans

<400> SEQUENCE: 70

```
Met Arg Ile Ala Leu Ile Ala His Asp Lys Lys Lys Asp Glu Met Val
1               5                   10                  15
```

```
Gln Phe Thr Ile Ala Tyr Lys Asp Val Leu Lys Asp His Glu Leu Tyr
         20                  25                  30

Ala Thr Gly Thr Thr Gly Met Arg Ile Met Glu Ala Ala Gln Leu Pro
         35                  40                  45

Val Lys Arg Phe Lys Ser Gly Pro Leu Gly Gly Asp Gln Gln Ile Gly
 50                  55                  60

Ala Leu Val Ala Glu Asn Lys Phe Asp Leu Ile Ile Phe Leu Arg Asp
 65                  70                  75                  80

Pro Leu Thr Ala Gln Pro His Glu Pro Asp Val Thr Ala Leu Val Arg
                 85                  90                  95

Leu Cys Asp Val Gln Arg Val Pro Leu Ala Thr Asn Ile Gly Thr Ala
             100                 105                 110

Glu Ile Leu Ile Lys Gly Leu Ala Arg Gly Asp Phe Thr Trp Arg Glu
             115                 120                 125

Leu Val His Asp Glu Glu Pro Arg Val
             130                 135

<210> SEQ ID NO 71
<211> LENGTH: 137
<212> TYPE: PRT
<213> ORGANISM: Bacillus subtilis

<400> SEQUENCE: 71

Met Lys Ile Ala Leu Ile Ala His Asp Lys Lys Gln Asp Met Val
 1               5                  10                  15

Gln Phe Thr Thr Ala Tyr Arg Asp Ile Leu Lys Asn His Asp Leu Tyr
         20                  25                  30

Ala Thr Gly Thr Thr Gly Leu Lys Ile His Glu Ala Thr Gly Leu Gln
         35                  40                  45

Ile Glu Arg Phe Gln Ser Gly Pro Leu Gly Gly Asp Gln Gln Ile Gly
 50                  55                  60

Ala Leu Ile Ala Ala Asn Ala Leu Asp Leu Val Ile Phe Leu Arg Asp
 65                  70                  75                  80

Pro Leu Thr Ala Gln Pro His Glu Pro Asp Val Ser Ala Leu Ile Arg
                 85                  90                  95

Leu Cys Asp Val Tyr Ser Ile Pro Leu Ala Thr Asn Met Gly Thr Ala
             100                 105                 110

Glu Ile Leu Val Arg Thr Leu Asp Gly Val Phe Glu Phe Arg Asp
             115                 120                 125

Leu Leu Arg Gly Glu Glu Pro Asn Val
             130                 135

<210> SEQ ID NO 72
<211> LENGTH: 140
<212> TYPE: PRT
<213> ORGANISM: Enterococcus faecalis

<400> SEQUENCE: 72

Met Lys Ile Ala Leu Ile Ala His Asp Arg Lys Lys Thr Leu Met Ile
 1               5                  10                  15

Lys Leu Ala Thr Ala Tyr Lys His Ile Leu Glu Lys His Glu Leu Tyr
         20                  25                  30

Ala Thr Gly Thr Thr Gly Met Lys Val Met Glu Ala Thr Gly Leu Pro
         35                  40                  45

Val His Cys Phe Lys Ser Gly Pro Leu Gly Gly Asp Gln Gln Ile Gly
 50                  55                  60

Ala Met Ile Ser Glu Asp Asn Ile Asp Leu Val Ile Phe Leu Arg Asp
```

```
                65                  70                  75                  80
Pro Leu Ser Ala Gln Pro His Glu Pro Asp Val Thr Ala Leu Ile Arg
                    85                  90                  95

Leu Ser Asp Val Tyr Glu Ile Pro Leu Ala Thr Asn Ile Gly Ser Ala
                100                 105                 110

Glu Ile Leu Leu Arg Gly Val Glu Ala Gly Phe Ala Asp Phe Arg Glu
            115                 120                 125

Val Ile His Glu Gly Asp Arg Arg Pro Leu Ala Phe
        130                 135                 140

<210> SEQ ID NO 73
<211> LENGTH: 134
<212> TYPE: PRT
<213> ORGANISM: Listeria innocua serovar 6a

<400> SEQUENCE: 73

Met His Ile Ala Leu Ile Ala His Asp Glu Lys Lys Asp Leu Met Val
1               5                   10                  15

Gly Phe Ala Thr Ala Tyr Lys His Leu Leu Glu Pro His Gln Leu Tyr
                20                  25                  30

Ala Thr Gly Thr Thr Gly Leu Arg Ile Ile Glu Ala Thr Gly Leu Thr
            35                  40                  45

Val His Arg Phe Lys Ser Gly Pro Leu Gly Gly Asp Gln Gln Ile Gly
        50                  55                  60

Ala Arg Ile Ser Glu Asn Lys Met Asp Leu Val Ile Phe Leu Arg Asp
65                  70                  75                  80

Pro Leu Thr Ala Gln Pro His Glu Pro Asp Val Ser Ala Leu Ile Arg
                85                  90                  95

Leu Cys Asp Val Tyr Glu Ile Pro Leu Ala Thr Asn Ile Gly Thr Ala
                100                 105                 110

Glu Ile Leu Ile Arg Gly Leu Gly Ala Gly Phe Leu Asp Trp Arg Asp
            115                 120                 125

Leu Arg Arg Asn Asp Glu
        130

<210> SEQ ID NO 74
<211> LENGTH: 152
<212> TYPE: PRT
<213> ORGANISM: Haemophilus influenzae
<220> FEATURE:
<221> NAME/KEY: misc_feature
<222> LOCATION: (91)..(91)
<223> OTHER INFORMATION: Xaa can be any naturally occurring amino acid

<400> SEQUENCE: 74

Met Gln Thr Thr Thr Arg Thr Leu Thr Gln His Lys Arg Ile Ala Leu
1               5                   10                  15

Val Ala His Asp Ser Cys Lys Lys Asn Leu Leu Asn Trp Thr Gln Lys
                20                  25                  30

His Lys Glu Ala Leu Lys Pro His Ile Leu Tyr Ala Thr Gly Thr Thr
            35                  40                  45

Gly His Ile Leu Glu Arg Glu Thr Gly Leu Ser Ile Gln Ser Leu Leu
        50                  55                  60

Ser Gly Pro Met Gly Gly Asp Gln Gln Leu Gly Gly Leu Ile Ala Glu
65                  70                  75                  80

Lys Lys Ile Asp Met Met Ile Phe Phe Trp Xaa Pro Met Asn Ala Ala
                85                  90                  95

Pro His Glu Pro Asp Val Lys Ala Leu Met Arg Ile Ala Thr Val Trp
```

```
              100                 105                 110

Asn Ile Pro Val Ala Ile Asn Gln Ser Ser Ala Asp Phe Leu Leu Thr
            115                 120                 125

Ser Val Leu Phe Glu Gln Asp Val Glu Ile Asp Val Pro Asp Tyr Glu
            130                 135                 140

Gly Tyr Leu Lys Glu Arg Leu Ala
145                 150

<210> SEQ ID NO 75
<211> LENGTH: 152
<212> TYPE: PRT
<213> ORGANISM: Photobacterium profundum

<400> SEQUENCE: 75

Met Gln Val Thr Thr Arg Thr Met Asn Lys Ser Lys His Ile Ala Leu
1               5                   10                  15

Val Ala His Asp Asn Cys Lys Gln Asp Leu Leu Arg Trp Val Lys Glu
            20                  25                  30

Phe Glu Asp Lys Leu Glu Asp His Thr Leu Tyr Ala Thr Gly Thr Thr
            35                  40                  45

Gly His Leu Leu Ser Lys Glu Thr Gly Leu Lys Ile Asn Cys Met Ile
        50                  55                  60

Ser Gly Pro Met Gly Gly Asp Gln Gln Leu Gly Ala Leu Ile Ser Glu
65                  70                  75                  80

Ser Lys Ile Asp Met Met Ile Phe Phe Trp Asp Pro Leu Asn Ala Val
                85                  90                  95

Pro His Asp Pro Asp Val Lys Ala Leu Leu Arg Ile Ser Ala Val Trp
            100                 105                 110

Asn Val Pro Val Ala Thr Asn Arg Ala Ser Ala Lys Phe Met Ile Thr
            115                 120                 125

Ser Pro Leu Leu Ala Glu Glu Ile Ser Ile Glu Ile Pro Asp Tyr Glu
            130                 135                 140

Ala Tyr Leu Ala Glu Arg Ile Gly
145                 150

<210> SEQ ID NO 76
<211> LENGTH: 151
<212> TYPE: PRT
<213> ORGANISM: Vibrio vulnificus

<400> SEQUENCE: 76

Met Gln Lys Thr Thr Arg Thr Met Pro Ala His Lys His Ile Ala Leu
1               5                   10                  15

Val Ala His Asp Asn Tyr Lys Pro Glu Leu Leu Arg Trp Val Lys Glu
            20                  25                  30

Asn Lys Glu Lys Leu Gln Ser His Phe Leu Tyr Ala Thr Gly Thr Thr
            35                  40                  45

Gly His Met Leu Ser Arg Glu Thr Gly Leu Ala Ile Lys Ser Met Ile
        50                  55                  60

Ser Gly Pro Met Gly Gly Asp Gln Gln Leu Gly Ala Leu Ile Ser Glu
65                  70                  75                  80

Gly Lys Ile Asp Met Leu Ile Phe Phe Trp Asp Pro Leu Asn Ala Val
                85                  90                  95

Pro His Asp Pro Asp Val Lys Ala Leu Leu Arg Ile Ala Ser Val Trp
            100                 105                 110

Asn Ile Pro Val Ala Thr Asn Arg Ala Thr Ala Lys Phe Leu Phe Glu
            115                 120                 125
```

Ser Pro Leu Leu Asn Glu Glu Val Asp Val Glu Ile Pro Asp Tyr Gln
130                 135                 140

Ala Tyr Leu Ala Gly Arg Thr
145                 150

<210> SEQ ID NO 77
<211> LENGTH: 151
<212> TYPE: PRT
<213> ORGANISM: Vibrio cholerae serotype O1

<400> SEQUENCE: 77

Met Lys Lys Thr Thr Arg Thr Met Ala Ala His Lys His Val Ala Leu
1               5                   10                  15

Val Ala His Asp Asn Cys Lys Gly Glu Leu Leu Arg Trp Val Thr Glu
                20                  25                  30

Asn Lys Glu Lys Leu Gln Arg His Phe Leu Tyr Ala Thr Gly Thr Thr
            35                  40                  45

Gly His Met Leu Ser Lys Glu Thr Gly Leu

```
Ala Tyr Leu Ala Glu Arg Met
145                 150

<210> SEQ ID NO 79
<211> LENGTH: 152
<212> TYPE: PRT
<213> ORGANISM: Photorhabdus luminescens subsp. laumondii

<400> SEQUENCE: 79

Met Glu Leu Thr Thr Arg Thr Met Ala Thr Ala Lys Asn Ile Ala Leu
1               5                   10                  15

Ile Ala His Asp His Cys Lys Thr Ser Leu Leu Ala Trp Ser Lys Lys
                20                  25                  30

His Lys Ser Leu Leu Lys Lys His His Leu Tyr Ala Thr Gly Thr Thr
            35                  40                  45

Gly Asn Leu Ile Gln Asn Glu Thr Gly Leu Ser Val Thr Asn Met Leu
        50                  55                  60

Ser Gly Pro Met Gly Gly Asp Gln Gln Ile Gly Ser Leu Ile Ser Glu
65                  70                  75                  80

Gly Lys Ile Asp Val Leu Ile Phe Phe Trp Asp Pro Leu Asn Ser Val
                85                  90                  95

Pro His Asp Pro Asp Val Lys Ala Leu Leu Arg Leu Ala Thr Val Trp
            100                 105                 110

Asn Ile Pro Val Ala Thr Asn Leu Ala Ser Ala Asp Phe Ile Val Ser
        115                 120                 125

Ser Pro Leu Phe Ser Glu Ser Val Asp Ile Gln Val Pro Asp Tyr Gln
130                 135                 140

His Tyr Leu Asn Gly Arg Leu Lys
145                 150

<210> SEQ ID NO 80
<211> LENGTH: 154
<212> TYPE: PRT
<213> ORGANISM: Yersinia pestis

<400> SEQUENCE: 80

Met Glu Leu Thr Thr Arg Thr

<210> SEQ ID NO 81
<211> LENGTH: 152
<212> TYPE: PRT
<213> ORGANISM: Erwinia carotovora subsp. atroseptica

<400> SEQUENCE: 81

Met Glu Phe Thr Thr Arg Thr Ile Pro Ala Gln Lys His Ile Ala Leu
1               5                   10                  15

Val Ala His Asp His Cys Lys Gln Ser Leu Leu Asp Trp Val Gly Thr
            20                  25                  30

Asn Lys Gln Gln Leu Thr Glu His Thr Leu Tyr Ala Thr Gly Thr Thr
        35                  40                  45

Gly Asn Leu Ile Gln Ser Asn Thr Gly Leu Pro Val Lys Ser Met Leu
    50                  55                  60

Ser Gly Pro Met Gly Gly Asp Gln Gln Val Gly Ala Leu Ile Ser Glu
65                  70                  75                  80

Gly Lys Ile Asp Leu Met Ile Phe Phe Trp Asp Pro Leu Asn Ala Val
                85                  90                  95

Pro His Asp Pro Asp Val Lys Ala Leu Leu Arg Leu Ala Thr Val Trp
            100                 105                 110

Asn Ile Pro Val Ala Thr Asn Arg Ala Thr Ala Asp Phe Leu Ile Asn
        115                 120                 125

Ser Ala Leu Phe Lys Glu Pro Val Gln Ile Ala Ile Pro Asp Tyr Gln
    130                 135                 140

Arg Tyr Leu Gln Asp Arg Leu Lys
145                 150

<210> SEQ ID NO 82
<211> LENGTH: 152
<212> TYPE: PRT
<213> ORGANISM: Escherichia coli O6:H1

<400> SEQUENCE: 82

Met Glu Leu Thr Thr Arg Thr Leu Pro Ser Arg Lys His Ile Ala Leu
1               5                   10                  15

Val Ala His Asp His Cys Lys Gln Met Leu Met Ser Trp Val Glu Arg
            20                  25                  30

His Gln Pro Leu Leu Glu Gln His Val Leu Tyr Ala Thr Gly Thr Thr
        35                  40                  45

Gly Asn Leu Ile Ser Arg Ala Thr Gly Met Asn Val Asn Ala Met Leu
    50                  55                  60

Ser Gly Pro Met Gly Gly Asp Gln Gln Val Gly Ala Leu Ile Ser Glu
65                  70                  75                  80

Gly Lys Ile Asp Val Leu Ile Phe Phe Trp Asp Pro Leu Asn Ala Val
                85                  90                  95

Pro His Asp Pro Asp Val Lys Ala Leu Leu Arg Leu Ala Thr Val Trp
            100                 105                 110

Asn Ile Pro Val Ala Thr Asn Val Ala Thr Ala Asp Phe Ile Ile Gln
        115                 120                 125

Ser Pro His Phe Asn Asp Ala Val Asp Ile Leu Ile Pro Asp Tyr Gln
    130                 135                 140

Arg Tyr Leu Ala Asp Arg Leu Lys
145                 150

<210> SEQ ID NO 83
<211> LENGTH: 152
<212> TYPE: PRT
<213> ORGANISM: Salmonella typhi

<400> SEQUENCE: 83

| | | | | | | | | | | | | | | |
|---|---|---|---|---|---|---|---|---|---|---|---|---|---|---|
| Met | Glu | Leu | Thr | Thr | Arg | Thr | Leu | Pro | Thr | Arg | Lys | His | Ile | Ala | Leu |
| 1 | | | | 5 | | | | | 10 | | | | | 15 | |
| Val | Ala | His | Asp | His | Cys | Lys | Gln | Met | Leu | Met | Asn | Trp | Val | Glu | Arg |
| | | | 20 | | | | | 25 | | | | | 30 | | |
| His | Gln | Pro | Leu | Leu | Glu | Lys | His | Val | Leu | Tyr | Ala | Thr | Gly | Thr | Thr |
| | | | 35 | | | | | 40 | | | | | 45 | | |
| Gly | Asn | Leu | Ile | Gln | Arg | Ala | Thr | Gly | Met | Asp | Val | Asn | Ala | Met | Leu |
| | 50 | | | | | 55 | | | | | 60 | | | | |
| Ser | Gly | Pro | Met | Gly | Gly | Asp | Gln | Gln | Val | Gly | Ala | Leu | Ile | Ser | Glu |
| 65 | | | | | 70 | | | | | 75 | | | | | 80 |
| Gly | Lys | Ile | Asp | Val | Leu | Ile | Phe | Phe | Trp | Asp | Pro | Leu | Asn | Ala | Val |
| | | | | 85 | | | | | 90 | | | | | 95 | |
| Pro | His | Asp | Pro | Asp | Val | Lys | Ala | Leu | Leu | Arg | Leu | Ala | Thr | Val | Trp |
| | | | 100 | | | | | 105 | | | | | 110 | | |
| Asn | Ile | Pro | Val | Ala | Thr | Asn | Val | Ser | Thr | Ala | Asp | Phe | Ile | Ile | Gln |
| | | | 115 | | | | | 120 | | | | | 125 | | |
| Ser | Pro | His | Phe | Asn | Asp | Ala | Val | Asp | Ile | Leu | Ile | Pro | Asp | Tyr | Ala |
| | | | 130 | | | | | 135 | | | | | 140 | | |
| Arg | Tyr | Leu | Ala | Glu | Arg | Leu | Lys | | | | | | | | |
| 145 | | | | | 150 | | | | | | | | | | |

<210> SEQ ID NO 84
<211> LENGTH: 152
<212> TYPE: PRT
<213> ORGANISM: Mannheimia succiniciproducens

<400> SEQUENCE: 84

| | | | | | | | | | | | | | | |
|---|---|---|---|---|---|---|---|---|---|---|---|---|---|---|---|
| Met | Glu | Thr | Thr | Phe | Arg | His | Val | Ala | Ala | Gln | Lys | His | Ile | Ala | Leu |
| 1 | | | | 5 | | | | | 10 | | | | | 15 | |
| Val | Ala | His | Asp | His | Cys | Lys | Glu | Asp | Leu | Ile | Asn | Trp | Cys | Gln | Lys |
| | | | 20 | | | | | 25 | | | | | 30 | | |
| Asn | Val | His | His | Leu | Gln | Asn | His | Gln | Leu | Tyr | Ala | Thr | Gly | Thr | Thr |
| | | | 35 | | | | | 40 | | | | | 45 | | |
| Gly | His | Leu | Ile | Glu | Lys | Ala | Thr | Glu | Leu | Lys | Ile | Asn | Ser | Leu | Leu |
| | 50 | | | | | 55 | | | | | 60 | | | | |
| Ser | Gly | Pro | Met | Gly | Gly | Asp | Gln | Gln | Leu | Gly | Ala | Leu | Ile | Ala | Glu |
| 65 | | | | | 70 | | | | | 75 | | | | | 80 |
| Asn | Lys | Ile | Asp | Val | Met | Ile | Phe | Phe | Trp | Asp | Pro | Met | Asn | Ala | Val |
| | | | | 85 | | | | | 90 | | | | | 95 | |
| Pro | His | Asp | Pro | Asp | Val | Lys | Ala | Leu | Leu | Arg | Ile | Ala | Ala | Val | Trp |
| | | | 100 | | | | | 105 | | | | | 110 | | |
| Asn | Ile | Pro | His | Ala | Met | Asn | Ile | Ala | Ser | Ala | Asp | Leu | Leu | Ile | Asn |
| | | | 115 | | | | | 120 | | | | | 125 | | |
| Ser | Pro | Leu | Ile | Asn | Arg | Glu | Ile | Glu | Leu | Arg | Ile | Pro | Asp | Tyr | Gln |
| | | | 130 | | | | | 135 | | | | | 140 | | |
| Thr | Tyr | Leu | Gln | Lys | Arg | Leu | Lys | | | | | | | | |
| 145 | | | | | 150 | | | | | | | | | | |

<210> SEQ ID NO 85
<211> LENGTH: 152
<212> TYPE: PRT
<213> ORGANISM: Pasteurella multocida

<400> SEQUENCE: 85

| | | | | | | | | | | | | | | |
|---|---|---|---|---|---|---|---|---|---|---|---|---|---|---|---|
| Met | Gln | Ser | Thr | Ala | Arg | Thr | Leu | Ser | Val | Asn | Lys | His | Ile | Ala | Leu |

-continued

```
                1               5                  10                  15
Val Ala His Asp His Cys Lys Gln Asp Leu Ile Asn Trp Cys Lys Thr
                        20                  25                  30

His Arg Thr Leu Leu Ala Gln His Thr Leu Tyr Ala Thr Gly Thr Thr
                        35                  40                  45

Gly Asn Leu Ile Gln Lys Glu Ala Asn Leu Pro Ile Lys Ser Leu Leu
            50                  55                  60

Ser Gly Pro Met Gly Gly Asp Gln Gln Leu Gly Leu Ile Ala Glu
65                      70                  75                      80

Lys Gln Ile Asp Val Leu Ile Phe Phe Trp Asp Pro Met Asn Ala Val
                        85                  90                  95

Pro His Asp Pro Asp Val Lys Ala Leu Met Arg Ile Ala Thr Val Trp
                        100                 105                 110

Asn Ile Pro Val Ala Met Asn Met Ala Thr Ala Asp Phe Leu Ile Thr
                        115                 120                 125

Ser Pro Ser Phe Ala Gln Glu Thr Gln Val Arg Ile Pro Asp Tyr Asp
            130                 135                 140

Gly Tyr Leu Lys Glu Arg Leu Lys
145                 150
```

<210> SEQ ID NO 86
<211> LENGTH: 145
<212> TYPE: PRT
<213> ORGANISM: Clostridium acetobutylicum

<400> SEQUENCE: 86

```
Met Asn Ser Lys Lys Ile Ala Leu Val Ala His Asp Asn Arg Lys
1                   5                   10                  15

Lys Ala Leu Ile Ser Trp Cys Glu Ala Asn Ser Glu Val Leu Ser Asn
                        20                  25                  30

His Ser Leu Cys Gly Thr Gly Thr Thr Ala Lys Leu Ile Lys Glu Ala
                        35                  40                  45

Thr Gly Leu Glu Val Phe Pro Tyr Lys Ser Gly Pro Met Gly Gly Asp
            50                  55                  60

Gln Gln Ile Gly Ala Ala Ile Val Asn Glu Asp Ile Asp Phe Met Ile
65                      70                  75                      80

Phe Phe Trp Asp Pro Leu Thr Ala Gln Pro His Asp Pro Asp Val Lys
                        85                  90                  95

Ala Leu Leu Arg Ile Ser Val Leu Tyr Asp Ile Pro Ile Ala Met Asn
                        100                 105                 110

Glu Ser Thr Ala Glu Phe Leu Ile Lys Ser Pro Ile Met Lys Glu Gln
            115                 120                 125

His Glu Arg His Ile Ile Asp Tyr Tyr Gln Lys Ile Arg Lys Asp Asn
            130                 135                 140

Phe
145
```

<210> SEQ ID NO 87
<211> LENGTH: 155
<212> TYPE: PRT
<213> ORGANISM: Thermotoga maritima

<400> SEQUENCE: 87

```
Met Asp Lys Lys Lys Arg Ile Ala Leu Ile Ala His Asp Arg Arg Lys
1                   5                   10                  15

Arg Asp Leu Leu Glu Trp Val Ser Phe Asn Leu Gly Thr Leu Ser Lys
                        20                  25                  30
```

```
His Glu Leu Tyr Ala Thr Gly Thr Thr Gly Ala Leu Leu Gln Glu Lys
            35                  40                  45

Leu Gly Leu Lys Val His Arg Leu Lys Ser Gly Pro Leu Gly Gly Asp
 50                  55                  60

Gln Gln Ile Gly Ala Met Ile Ala Glu Gly Lys Ile Asp Val Leu Ile
 65                  70                  75                  80

Phe Phe Trp Asp Pro Leu Glu Pro Gln Ala His Asp Val Asp Val Lys
            85                  90                  95

Ala Leu Ile Arg Ile Ala Thr Val Tyr Asn Ile Pro Val Ala Ile Thr
            100                 105                 110

Arg Ser Thr Ala Asp Phe Leu Ile Ser Ser Pro Leu Met Asn Asp Val
            115                 120                 125

Tyr Glu Lys Ile Gln Ile Asp Tyr Glu Glu Leu Glu Arg Arg Ile
            130                 135                 140

Arg Lys Val Val Glu Gly Glu Glu Glu Thr
145                 150                 155

<210> SEQ ID NO 88
<211> LENGTH: 148
<212> TYPE: PRT
<213> ORGANISM: Leptospira interrogans

<400> SEQUENCE: 88

Met Lys Glu Val Ser Val Pro Ala Ile Lys Arg Ile Val Leu Ile Ala
 1               5                  10                  15

His Asp Asn Arg Lys Glu Asp Leu Val Asn Trp Val Lys Thr His Arg
            20                  25                  30

Glu Ile Leu Ser Lys His Gln Leu Tyr Gly Thr Gly Thr Thr Gly Lys
            35                  40                  45

Leu Ile Ser Glu Glu Thr Glu Leu Pro Val Tyr Arg Phe Leu Ser Gly
 50                  55                  60

Pro Leu Gly Gly Asp Gln Gln Ile Gly Ala Lys Ile Ala Glu Gly Asp
 65                  70                  75                  80

Leu Asp Ile Val Ile Phe Phe Trp Asp Pro Leu Thr Ala Gln Pro His
            85                  90                  95

Asp Pro Asp Val Lys Ala Leu Leu Arg Ile Ala Val Leu Tyr Asn Val
            100                 105                 110

Pro Met Ala Cys Asn Arg Ser Thr Ala Asp Tyr Met Ile Ser Ser Pro
            115                 120                 125

Gln Phe Thr Lys Thr Tyr Lys Lys Ile Leu Leu Ser Tyr Asn Thr Lys
            130                 135                 140

Val Lys Lys Asp
145
```